US011434538B2

(12) United States Patent
Babic et al.

(10) Patent No.: US 11,434,538 B2
(45) Date of Patent: *Sep. 6, 2022

(54) METHOD OF NUCLEIC ACID SEQUENCE DETECTION

(71) Applicant: BioSpyder Technologies, Inc., Carlsbad, CA (US)

(72) Inventors: Milos Babic, Vista, CA (US); Christy Lee Trejo, San Diego, CA (US); Peter J. Shepard, Carlsbad, CA (US); Joanne M. Yeakley, Encinitas, CA (US); Bruce Seligmann, Tucson, AZ (US)

(73) Assignee: BioSpyder Technologies, Inc., Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/865,246

(22) Filed: May 1, 2020

(65) Prior Publication Data
US 2020/0385816 A1 Dec. 10, 2020

Related U.S. Application Data

(60) Continuation-in-part of application No. 15/954,546, filed on Apr. 16, 2018, now Pat. No. 11,091,810, which is a continuation-in-part of application No. 15/387,650, filed on Dec. 22, 2016, now Pat. No. 10,683,534, which is a continuation-in-part of application No. PCT/US2016/014999, filed on Jan. 26, 2016, which is a continuation-in-part of application No. 14/788,670, filed on Jun. 30, 2015, now Pat. No. 9,856,521, said application No. 15/387,650 is a continuation-in-part of application No. 14/788,670, filed on Jun. 30, 2015, now Pat. No. 9,856,521, application No. 16/865,246, which is a continuation-in-part of application No. 15/387,650, filed on Dec. 22, 2016, now Pat. No. 10,683,534, and a continuation-in-part of application No. 15/920,381, filed on Mar. 13, 2018, now Pat. No. 10,934,576, which is a division of application No. 14/595,069, filed on Jan. 12, 2015, now Pat. No. 9,938,566, which is a continuation-in-part of application No. 14/480,525, filed on Sep. 8, 2014, now Pat. No. 9,957,550.

(60) Provisional application No. 62/108,161, filed on Jan. 27, 2015.

(51) Int. Cl.
*C12Q 1/6886* (2018.01)
*C12Q 1/6806* (2018.01)

(52) U.S. Cl.
CPC ......... *C12Q 1/6886* (2013.01); *C12Q 1/6806* (2013.01); *C12Q 2600/112* (2013.01); *C12Q 2600/156* (2013.01)

(58) Field of Classification Search
CPC .................................. C12Q 1/68; C07H 21/00
See application file for complete search history.

(56) References Cited

U.S. PATENT DOCUMENTS

| | | | | |
|---|---|---|---|---|
| 4,988,617 A * | 1/1991 | Landegren | ........... | C12Q 1/6827 536/78 |
| 5,225,324 A * | 7/1993 | McFadden | ............. | C12Q 1/689 435/29 |
| 5,424,413 A * | 6/1995 | Hogan | ................. | C12Q 1/6823 536/24.31 |
| 5,691,146 A * | 11/1997 | Mayrand | ................ | C07H 21/04 435/5 |
| 5,871,921 A * | 2/1999 | Landegren | ........... | C12Q 1/6813 435/6.1 |
| 6,027,889 A | 2/2000 | Barany et al. | | |
| 6,180,778 B1 * | 1/2001 | Bastian | ................ | C12N 15/101 536/25.31 |
| 6,368,801 B1 * | 4/2002 | Faruqi | .................. | C12Q 1/6844 435/6.1 |
| 7,312,039 B2 | 12/2007 | Barany et al. | | |
| 7,320,865 B2 | 1/2008 | Barany et al. | | |
| 7,429,453 B2 | 9/2008 | Barany et al. | | |
| 8,597,891 B2 | 12/2013 | Barany et al. | | |
| 8,741,564 B2 | 6/2014 | Seligmann | | |
| 9,856,521 B2 * | 1/2018 | Stevens | ................ | C12Q 1/6827 |
| 10,683,534 B2 * | 6/2020 | Stevens | ................ | C12Q 1/6827 |
| 2003/0083273 A1 * | 5/2003 | Woolf | ................... | C12N 15/113 514/44 A |
| 2003/0104378 A1 * | 6/2003 | Allawi | ................. | C12N 9/1252 435/6.18 |
| 2003/0108913 A1 * | 6/2003 | Schouten | ............... | C12Q 1/686 435/6.1 |
| 2004/0101835 A1 * | 5/2004 | Willis | ................... | C12Q 1/6827 435/6.12 |
| 2004/0137484 A1 * | 7/2004 | Zhang | .................... | C12Q 1/682 435/6.11 |
| 2005/0026166 A1 | 2/2005 | Bi | | |
| 2006/0014189 A1 * | 1/2006 | Wenz | ................... | C12Q 1/6813 435/6.12 |
| 2006/0121452 A1 * | 6/2006 | Dhallan | ............... | C12Q 1/6827 435/5 |
| 2006/0246475 A1 | 11/2006 | Peterson et al. | | |
| 2007/0065816 A1 * | 3/2007 | Dong | ................... | C12Q 1/6809 435/6.11 |
| 2007/0275375 A1 * | 11/2007 | Van Eijk | ............... | C12Q 1/6844 435/6.11 |
| 2008/0125324 A1 * | 5/2008 | Petersdorf | ............ | C12Q 1/6813 506/1 |
| 2008/0182239 A1 * | 7/2008 | Mullinax | ............. | C12Q 1/6811 435/6.14 |

(Continued)

FOREIGN PATENT DOCUMENTS

CA 2914367 A1 12/2014

OTHER PUBLICATIONS

Ahern, H. The Scientist 9(15) : 20 (Year: 1995).*

(Continued)

*Primary Examiner* — Ethan C Whisenant

(57) ABSTRACT

Barcoded ligation assay products from individual samples.

9 Claims, 27 Drawing Sheets

Specification includes a Sequence Listing.

(56) References Cited

U.S. PATENT DOCUMENTS

| | | | |
|---|---|---|---|
| 2008/0227104 A1* | 9/2008 | Hayashizaki | C12Q 1/6853 435/6.11 |
| 2009/0203085 A1* | 8/2009 | Kurn | C12Q 1/686 435/91.2 |
| 2012/0003644 A1* | 1/2012 | Skorecki | C12Q 1/703 435/7.1 |
| 2013/0005594 A1* | 1/2013 | Terbrueggen | C12Q 1/6834 506/9 |
| 2013/0197056 A1* | 8/2013 | Huntsman | C12N 15/1079 506/10 |
| 2014/0141418 A1* | 5/2014 | Park | C12Q 1/6844 435/6.11 |
| 2014/0170653 A1* | 6/2014 | Ying | G01N 33/542 435/6.11 |
| 2014/0227683 A1* | 8/2014 | Cobb | C12Q 1/6818 435/5 |
| 2014/0227691 A1* | 8/2014 | May | C12Q 1/6806 435/6.11 |
| 2014/0287468 A1* | 9/2014 | Richard | C12Q 1/6806 435/91.53 |
| 2015/0038336 A1* | 2/2015 | Barany | C12Q 1/6806 506/2 |
| 2016/0068886 A1 | 3/2016 | Yeakley et al. | |
| 2016/0068907 A1 | 3/2016 | Shepard et al. | |
| 2017/0101671 A1 | 4/2017 | Stevens et al. | |

OTHER PUBLICATIONS

Larsson et al., Nature Methods 7(5) :395 (Year: 2010).*
Li et al., Unit 4.13 Current Protocols in Molecular Biology 4.13. 1-4.13.9 (Year: 2012).*
Meyer et al., Nucleic Acids Research 35(15) : e97 (Year: 2007).*
PECetus GeneAmp DNA Amplification Reagent kit (Year: 1988).*
Black et al., Heated Oligonucleotide Ligation Assay (HOLA): An Affordable Single Nucleotide Polymorphism Assay. J. of Medical Entomology 43(2) :238-247 (Year: 2006).*
Nickerson et al., Automated DNA diagnostics using an ELISA-based oligonucleotide ligation assay.. PNAS 87 : 8923-8927 (Year: 1990).*
Schouten et al., Relative quantification of 40 nucleic acid sequences by multiplex ligation-dependent probe amplification. Nucleic Acid Research 30(12) : e57 (Year: 2002).*
Parameswaran et al., Nucleic Acis Research 35(19) : e130 (Year: 2007).*
Duncavage et al., Hybrid Capture and Next-Generation Sequencing Identify Viral Integration Sites from Formalin-Fixed, Paraffin-Embedded Tissue. The Journal of Molecular Diagnostics 13(3): 325 (Year: 2011).*
Weibrecht et al., Nature Protocols 8(2) : 355 (Year: 2013).*
Hamady et al. Error-correcting barcoded primers allow hundreds of samples to be pyrosequenced in multiplex. Nature Methods 5(3) : 235-237 (Year: 2008).*
Ahern, H. The Scientist 9 (15) : 20 (1995).*
Barany, F. The ligase chain reaction in a PCR world. PCR Methods and Applications 1 : 5-16 (1991).*
Cai et al., Human microRNAs are processed from capped, polyadenylated transcripts that can also function as mRNAs.RNA 10 : 1957 (2004).*
Hsuih et al., Novel, Ligation-Dependent PCR Assay for Detection of Hepatitis C Virus in Serum. J. of Clinical Microbiology 34 (3): 501 (1996).*
Pritchard et al., MicroRNA profiling : approaches and considerations. Nature Reviews Genetics 13 :358 (2012).*
Schouten et al., Relative quantification of 40 nucleic acid sequences by multiplex ligation-dependent probe amplification. Nucleic Acids Research 30 (12) : e57 (2002).*
Shevelev et al., The 3'-5' Exonucleases. Nature Reviews Molecular Cell Biology 3 :1 (2002).*
Shi et al., Facile means for quantifying microRNA expression by real-time PCR. BioTechniques 39 (4) : 519 (2005).*
Vallone et al., qPCR Workshop hald Jul. 26-27, 2006.at NFSTC—Presentation slides.*
Vrettou et al., Real-Time PCR for Single-Cell Genotyping in Sickle Cell and Thalassemia Syndromes as a Rapid, Accurate, Reliable, and Widely Applicable Protocol for Preimplantation Genetic Diagnosis. Human Mutation 23 : 513 (2004).*
Wiedmann et al., Ligase chain reaction (LCR)—overview and applications. PCR Methods and Applications 1 : 5-16 (1991).*
Chun et al., Dual priming oligonucleotide system for the multiplex detection of respiratory viruses and SNP genotyping of CYP2C19 gene. Nucleic Acids Research 35(6) : e40 (2007).*
Hwang et al., Biotechniques 35(6) : 1180 (2003).Sanger et al.PNAS 74(12) : 5463 (1977).*
Sanger et al. 74 (12) : 5463 (1977).*
International Search Report and Written Opinion mailed by ISA/US dated Apr. 14, 2016 for related application PCT/US16/14999.
Response to second Examination Report in UK sister application, with 3rd set of replacement claims, dated May 3, 2017.
Intention to Grant UK patent, dated May 23, 2017.
Replacement claims for foreign counterpart GB 1 614 871.0, filed in UK IPO, Aug. 31, 2016.
First Examination Report, dated Oct. 14, 2016.
Response to first Examination Report, dated Dec. 13, 2016, with 2nd set of replacement claims.
Second Examination Report, dated Feb. 27, 2017.

* cited by examiner

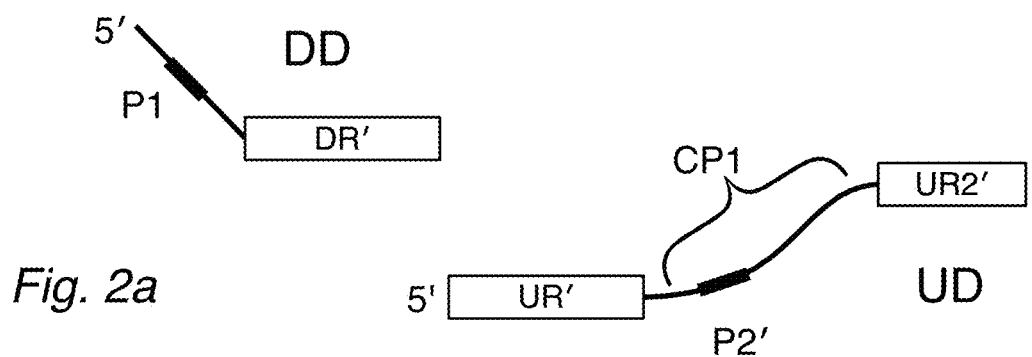
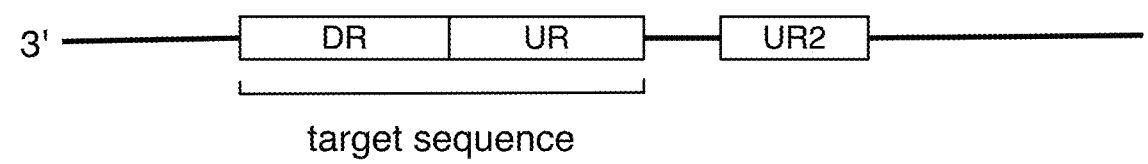
Fig. 2a
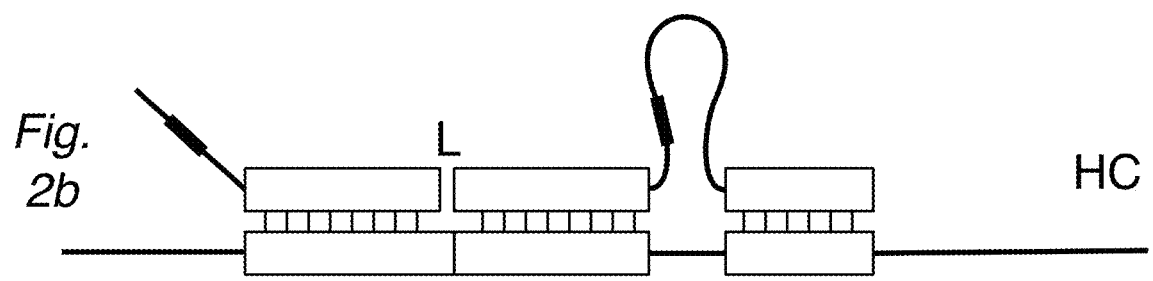
Fig. 2b
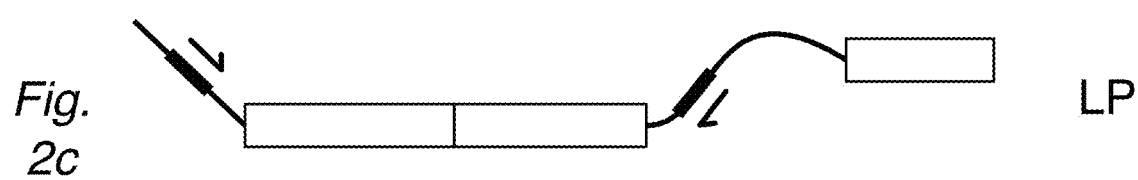
Fig. 2c
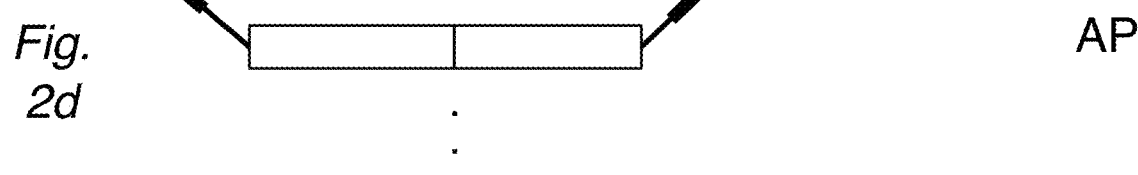
Fig. 2d

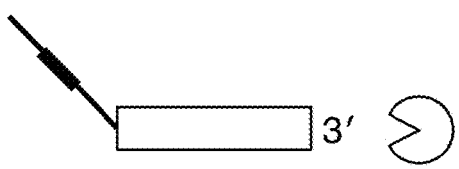
*Fig. 2e*
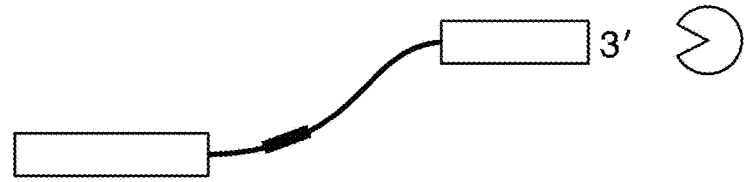
*Fig. 2f*
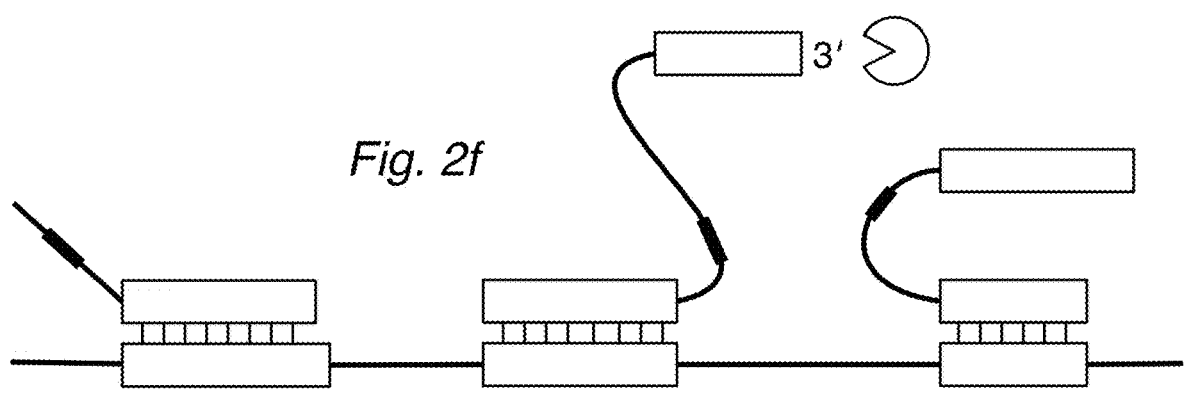
*Fig. 2g*
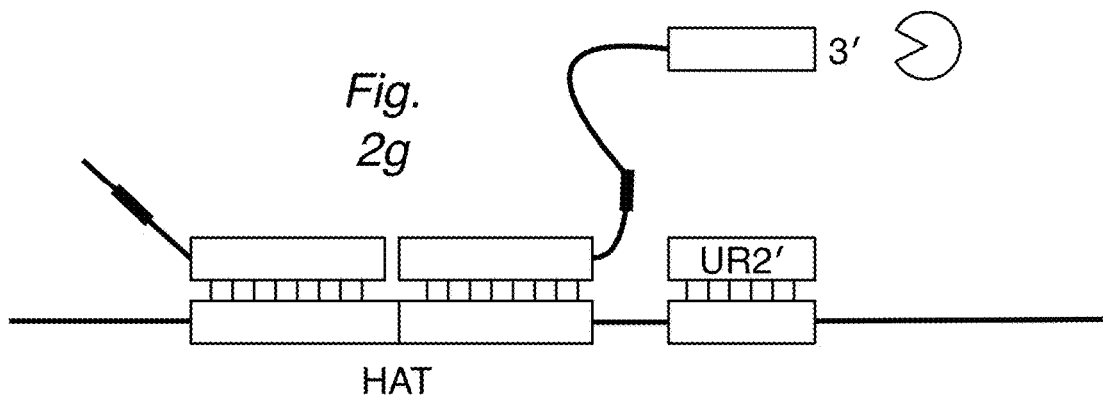

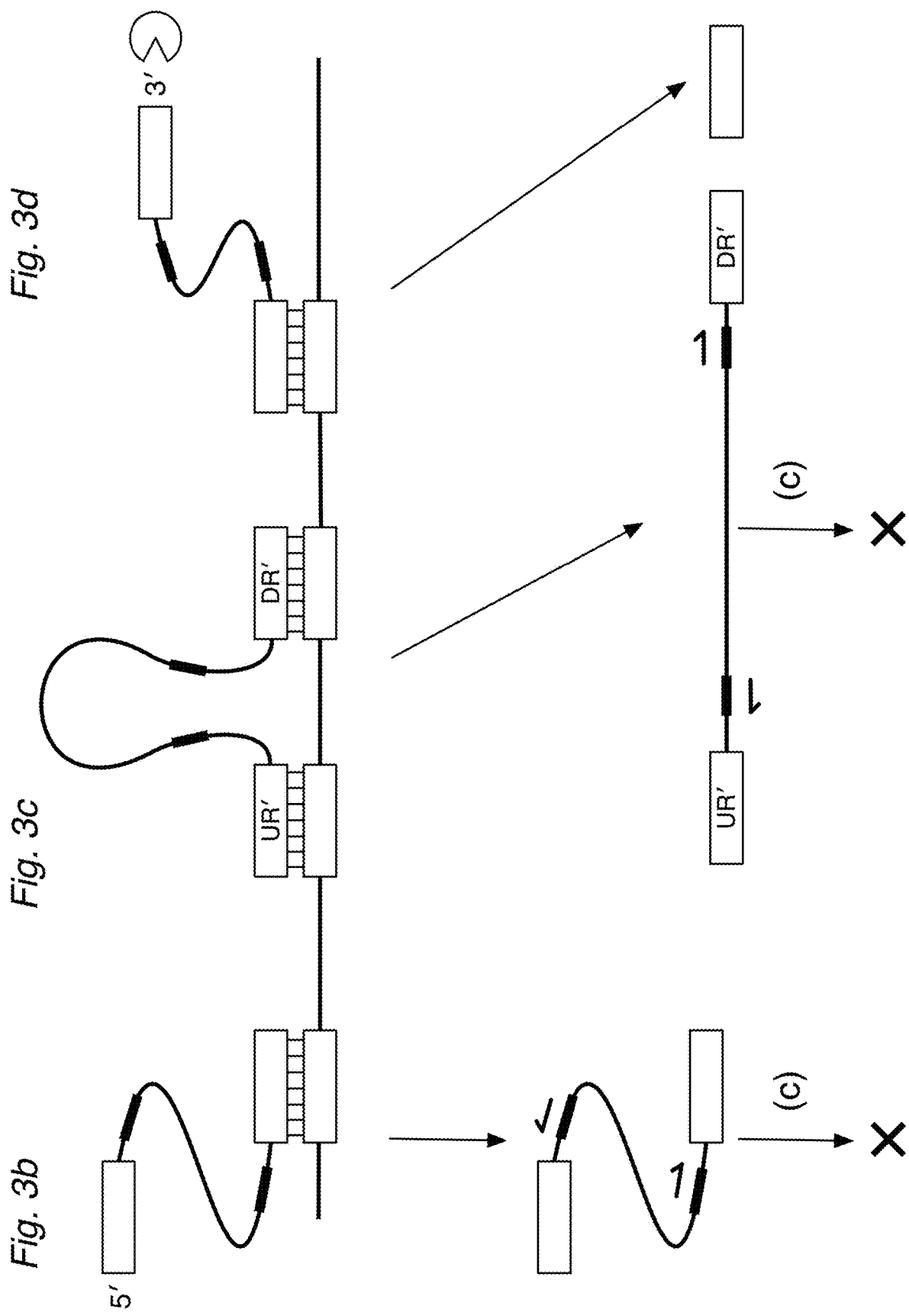

Figure 6a

| gene | DR' and UR' of detectors | |
|---|---|---|
| ACTB_1 | AGGTGTGCACTTTTATTCAACTGGTCTCAAGTCAGTGTACAGGTAAGCCC | SEQ ID NO:33 |
| BAD_3 | CGAGGAAGTCCCTTCTTAAAGGAGTCCACAAACTCGTCACTCATCCTCCG | SEQ ID NO:34 |
| BCAT2_3 | CTTGTCATTCCATTCCACCATCAGCATGTGGTCGGTAAATGTCTTCCCAA | SEQ ID NO:35 |
| BMP4_1 | GTGTATATCTGTCTATCCTCAAGGACTGCCTGATCTCAGCGGCACCCACA | SEQ ID NO:36 |
| BRCA1_2 | TGCCCAAGGACTATTCTGACTTTAAGTCACATAATCGATCCCAAGCACTC | SEQ ID NO:37 |
| BRCA2_1 | TTCTTCCGTACTGGCCTGGGAACTCTCCTGTTCTTTGATCAGAGATGTAG | SEQ ID NO:38 |
| CDH1_1 | TATTCTCGGTTTTCTGTGCACACCTGGAATTGGGCAAATGTGTTCAGCTC | SEQ ID NO:39 |
| EGF_3 | TTTTCCATCCCCAGCAAATCCTTTCAAACACTGACATGTGGCATCCTCTC | SEQ ID NO:40 |
| EGFR_1 | AGCAAAAGGAACATTTTGTATGTGTGTGTGACTGAACATAACTGTAGGCT | SEQ ID NO:41 |
| ESR1_1 | GCGACAAAACCGAGTCACATCAGTAATAGTATGCATCGGCAAAAGGGCAT | SEQ ID NO:42 |
| GAPDH_3 | CCATTGATGACAAGCTTCCCGTTCTCAGCCTTGACGGTGCCATGGAATTT | SEQ ID NO:43 |
| GATA3_3 | CTCTCTGAAACCCTCAACGGCAACTGGTGAACGGTAACACTGATTGCCCA | SEQ ID NO:44 |
| ICAM1_2 | CTGGCATCCGTCAGGAAGTGTGGGCCTTTGTGTTTTGATGCTACACATGT | SEQ ID NO:45 |
| IGF2_3 | CCCTGCCCCAGCCTGATGGAACCCTCTGTTTACACACCTGCTAGCCCCTT | SEQ ID NO:46 |
| KIT_3 | TGAGCCTATTCTCACAGATCTCCTTTTGTCGGCCTTGGTTGGGACAACAT | SEQ ID NO:47 |
| KRT19_2 | TCCGTTTCTGCCAGTGTGTCTTCCAAGGCAGCTTTCATGCTCAGCTGTGA | SEQ ID NO:48 |
| LAMP1_2 | CTTTGAATATATTGACTGAAAACGUCTTCGTGACACGGACGTGCTCCTCC | SEQ ID NO:49 |
| MUC1_3 | ATCGAGAGGCTGCTTCCGTTTTATACTGATTGAACTGTGTCTCCACGTCG | SEQ ID NO:50 |
| NFKBIA_1 | TACATTATGTACACCATTTACAGGAGGGTAACACAAACCTTGACAGGTAG | SEQ ID NO:51 |
| PTEN_1 | TGCATAGCATTTACACACAGAGCCACTGCTGCACAGCACAAGAGTATCTG | SEQ ID NO:52 |
| TFF1_1 | AAGCGTGTCTGAGGTGTCCGGTGGAGGTGGCAGCCGAGCTCTGGGACTAA | SEQ ID NO:53 |
| TIMP1_2 | GCATCCCCTAAGGCTTGGAACCCTUTATACATCTTGGTCATCTTGATCTC | SEQ ID NO:54 |
| VEGFA_3 | GATGGTGTGGTGGCGGCAGCGTGGTTTCTGTATCGATCGTTCTGTATCAG | SEQ ID NO:55 |
| WNT1_1 | AGGAGCCGCTAATAGCTACAGTGGAAGGAAATACTGATTCCAGGAGGCAA | SEQ ID NO:56 |

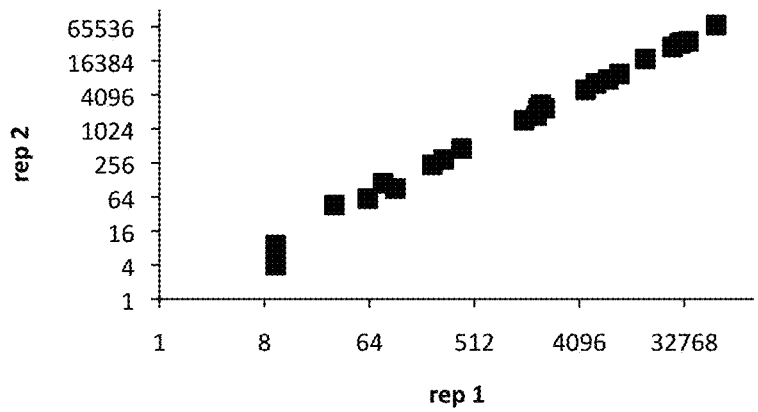
Fig. 6b: Anchored probes, 10 ng input
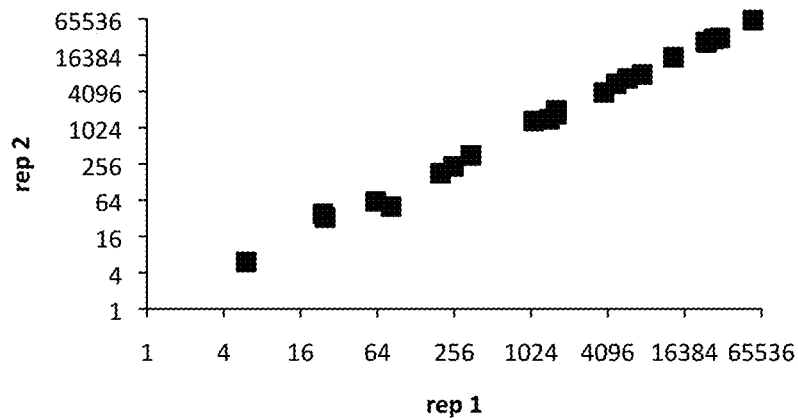
Fig. 6c: Anchored probes, 1 ng input
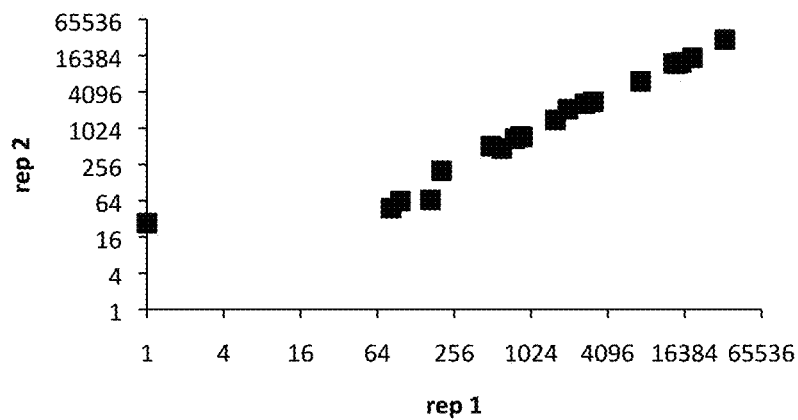
Fig. 6d: Anchored probes, 0.1 ng input

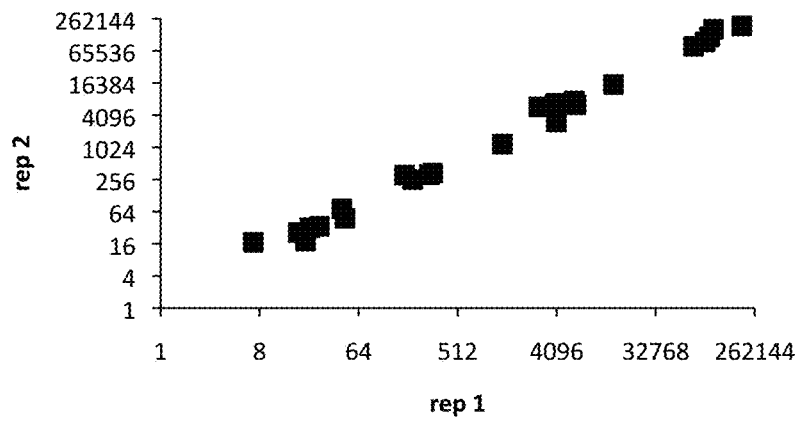
Fig. 6e: Circular probe, 10 ng input
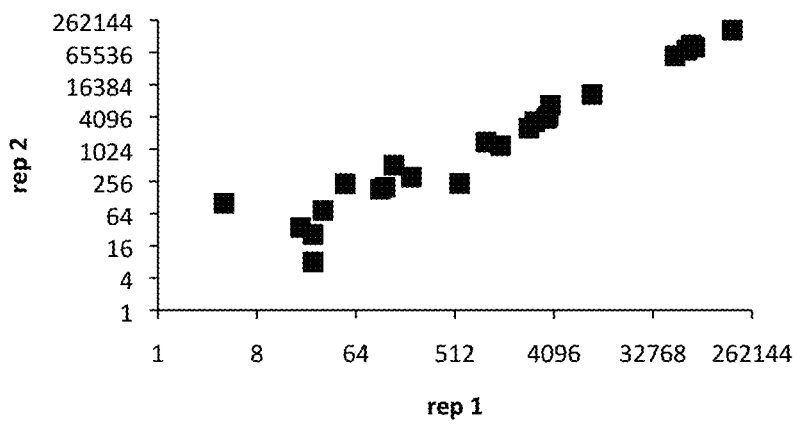
Fig. 6f: Circular probe, 1 ng input
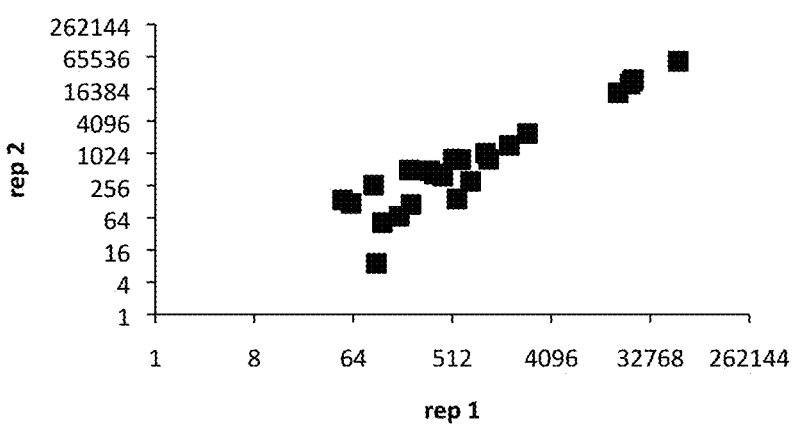
Fig. 6g: Circular probe, 0.1 ng input

*Fig. 12*
H&E stained, processed *in situ*
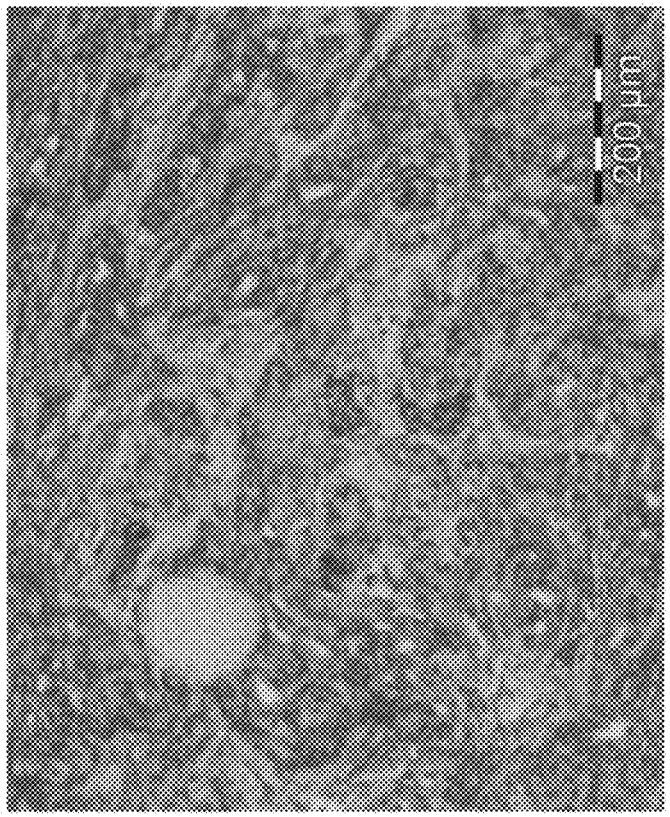
Post-Elution
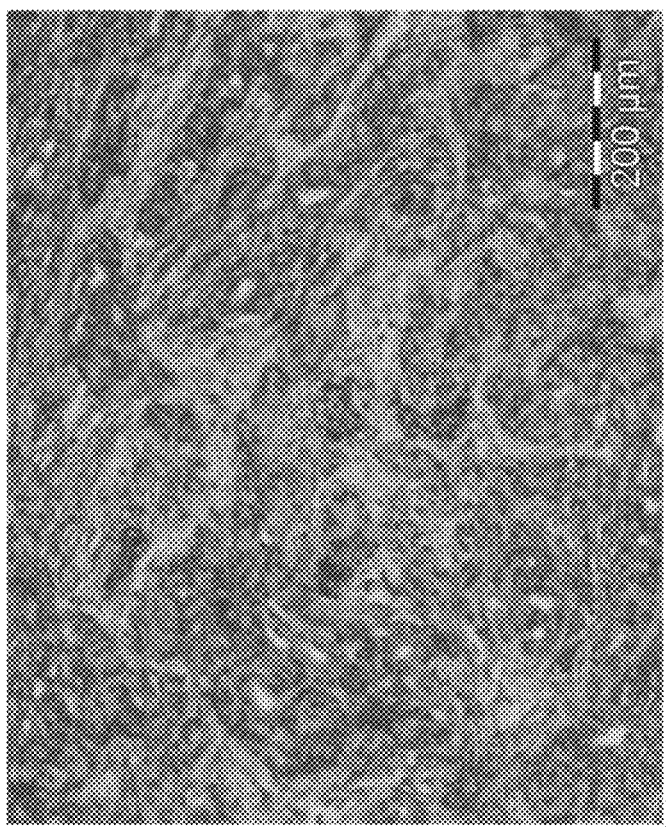
Pre-Elution

*Fig. 13*
CellSensus profiling of 130 μm diameter areas
Post-Elution
Pre-Elution

SEQUENCE LISTING

```
<160> NUMBER OF SEQ ID NOS: 56

<210> SEQ ID NO 1
<211> LENGTH: 22
<212> TYPE: DNA
<213> ORGANISM: Artificial Sequence
```

```
<220> FEATURE:
<223> OTHER INFORMATION: synthetic downstream amplification sequence
      (P1)

<400> SEQUENCE: 1
caagcagaag acggcatacg ag                                              22

<210> SEQ ID NO 2
<211> LENGTH: 23
<212> TYPE: DNA
<213> ORGANISM: Artificial Sequence
<220> FEATURE:
<223> OTHER INFORMATION: synthetic upstream amplification sequence (P2')

<400> SEQUENCE: 2
atctcggtgg tcgccgtatc att                                             23

<210> SEQ ID NO 3
<211> LENGTH: 23
<212> TYPE: DNA
<213> ORGANISM: Artificial Sequence
<220> FEATURE:
<223> OTHER INFORMATION: synthetic amplification primer (P2)

<400> SEQUENCE: 3
aatgatacgg cgaccaccga gat                                             23

<210> SEQ ID NO 4
<211> LENGTH: 50
<212> TYPE: RNA
<213> ORGANISM: Homo sapiens

<400> SEQUENCE: 4
cgaccacuuu gucaagcuca uuccugguya ugacaacgaa uuuggcuaca                50

<210> SEQ ID NO 5
<211> LENGTH: 50
<212> TYPE: RNA
<213> ORGANISM: Homo sapiens

<400> SEQUENCE: 5
cgaccacuuu gucaagcuca uuccugguya ugacaacgaa uuuggcuaca                50

<210> SEQ ID NO 6
<211> LENGTH: 25
<212> TYPE: RNA
<213> ORGANISM: Homo sapiens

<400> SEQUENCE: 6
ugguaugaca acgaauuugg cuaca                                           25

<210> SEQ ID NO 7
<211> LENGTH: 25
<212> TYPE: DNA
<213> ORGANISM: Homo sapiens

<400> SEQUENCE: 7
tgtagccaaa ttcgttgtca tacca                                           25

<210> SEQ ID NO 8
<211> LENGTH: 25
<212> TYPE: RNA
<213> ORGANISM: Homo sapiens
```

```
<400> SEQUENCE: 8
cgaccacuuu gucaagcuca uuucc                                              25

<210> SEQ ID NO 9
<211> LENGTH: 25
<212> TYPE: DNA
<213> ORGANISM: Homo sapiens

<400> SEQUENCE: 9
ggaaatgagc ttgacaaagt ggtcg                                              25

<210> SEQ ID NO 10
<211> LENGTH: 22
<212> TYPE: RNA
<213> ORGANISM: Homo sapiens

<400> SEQUENCE: 10
ugagguagua gguuguauag uu                                                 22

<210> SEQ ID NO 11
<211> LENGTH: 22
<212> TYPE: RNA
<213> ORGANISM: Homo sapiens

<400> SEQUENCE: 11
ugagguagua gguugugugg uu                                                 22

<210> SEQ ID NO 12
<211> LENGTH: 22
<212> TYPE: RNA
<213> ORGANISM: Homo sapiens

<400> SEQUENCE: 12
ugagguagua gguuguaugg uu                                                 22

<210> SEQ ID NO 13
<211> LENGTH: 22
<212> TYPE: RNA
<213> ORGANISM: Homo sapiens

<400> SEQUENCE: 13
agagguagua gguugcauag uu                                                 22

<210> SEQ ID NO 14
<211> LENGTH: 22
<212> TYPE: RNA
<213> ORGANISM: Homo sapiens

<400> SEQUENCE: 14
ugagguagga gguuguauag uu                                                 22

<210> SEQ ID NO 15
<211> LENGTH: 22
<212> TYPE: RNA
<213> ORGANISM: Homo sapiens

<400> SEQUENCE: 15
ugagguagua gauuguauag uu                                                 22

<210> SEQ ID NO 16
<211> LENGTH: 22
<212> TYPE: RNA
<213> ORGANISM: Homo sapiens
```

```
<400> SEQUENCE: 16
ugagguagua guuuguacag uu                                              22

<210> SEQ ID NO 17
<211> LENGTH: 22
<212> TYPE: RNA
<213> ORGANISM: Homo sapiens

<400> SEQUENCE: 17
ugagguagua guuugugcug uu                                              22

<210> SEQ ID NO 18
<211> LENGTH: 11
<212> TYPE: DNA
<213> ORGANISM: Homo sapiens

<400> SEQUENCE: 18
aactatacaa c                                                          11

<210> SEQ ID NO 19
<211> LENGTH: 11
<212> TYPE: DNA
<213> ORGANISM: Homo sapiens

<400> SEQUENCE: 19
ctactacctc a                                                          11

<210> SEQ ID NO 20
<211> LENGTH: 34
<212> TYPE: DNA
<213> ORGANISM: Artificial Sequence
<220> FEATURE:
<223> OTHER INFORMATION: DNA reverse complement for human let-7a
      flanked by synthetic 2S sequences, as hybridized

<400> SEQUENCE: 20
taagagaact atacaaccta ctacctcacg gaac                                 34

<210> SEQ ID NO 21
<211> LENGTH: 34
<212> TYPE: DNA
<213> ORGANISM: Artificial Sequence
<220> FEATURE:
<223> OTHER INFORMATION: human let-7a microRNA flanked by synthetic 2S
      DNA sequences, as hybridized

<400> SEQUENCE: 21
gttccgugag guaguagguu guauaguuct ctta                                 34

<210> SEQ ID NO 22
<211> LENGTH: 34
<212> TYPE: DNA
<213> ORGANISM: Artificial Sequence
<220> FEATURE:
<223> OTHER INFORMATION: DNA reverse complement for human let-7a flanked
      by synthetic 2S sequences, as ligated detector oligo (DO)

<400> SEQUENCE: 22
taagagaact atacaaccta ctacctcacg gaac                                 34

<210> SEQ ID NO 23
<211> LENGTH: 34
<212> TYPE: DNA
<213> ORGANISM: Artificial Sequence
```

```
<220> FEATURE:
<223> OTHER INFORMATION: human let-7a microRNA flanked by synthetic 2S
      DNA sequences, as ligated

<400> SEQUENCE: 23
gttccgugag guaguagguu guauaguuct ctta                              34

<210> SEQ ID NO 24
<211> LENGTH: 34
<212> TYPE: DNA
<213> ORGANISM: Artificial Sequence
<220> FEATURE:
<223> OTHER INFORMATION: DNA reverse complement of human let-7a flanked
      by synthetic 2S sequences, as ligated detector oligo (DO)

<400> SEQUENCE: 24
taagagaact atacaaccta ctacctcacg gaac                              34

<210> SEQ ID NO 25
<211> LENGTH: 34
<212> TYPE: DNA
<213> ORGANISM: Artificial Sequence
<220> FEATURE:
<223> OTHER INFORMATION: human let-7c microRNA flanked by synthetic DNA
      2S sequences, as ligated

<400> SEQUENCE: 25
gttccgugag guaguagguu guaugguuct ctta                              34

<210> SEQ ID NO 26
<211> LENGTH: 16
<212> TYPE: DNA
<213> ORGANISM: Artificial Sequence
<220> FEATURE:
<223> OTHER INFORMATION: DNA complement of downstream region (DR') for
      human let-7a, extended with synthetic poly-dT region

<400> SEQUENCE: 26 tttttttaa ctatac                                                   16

<210> SEQ ID NO 27
<211> LENGTH: 14
<212> TYPE: DNA
<213> ORGANISM: Homo sapiens

<400> SEQUENCE: 27
aacctactac ctca                                                    14

<210> SEQ ID NO 28
<211> LENGTH: 27
<212> TYPE: RNA
<213> ORGANISM: Artificial Sequence
<220> FEATURE:
<223> OTHER INFORMATION: human let-7a microRNA supplemented by synthetic
      poly-A tail

<400> SEQUENCE: 28
ugagguagua gguuguauag uuaaaaa                                      27

<210> SEQ ID NO 29
<211> LENGTH: 16
<212> TYPE: DNA
<213> ORGANISM: Artificial Sequence
<220> FEATURE:
<223> OTHER INFORMATION: DNA complement of downstream region (DR') for
      human let-7b, extended with synthetic poly-dT region
```

<400> SEQUENCE: 29 tttttttttaa ccacac                                                    16

<210> SEQ ID NO 30
<211> LENGTH: 27
<212> TYPE: RNA
<213> ORGANISM: Artificial Sequence
<220> FEATURE:
<223> OTHER INFORMATION: human let-7b microRNA supplemented by synthetic
      poly-A tail

<400> SEQUENCE: 30
ugagguagua gguugugugg uuaaaaa                                         27

<210> SEQ ID NO 31
<211> LENGTH: 22
<212> TYPE: DNA
<213> ORGANISM: Artificial Sequence
<220> FEATURE:
<223> OTHER INFORMATION: partial upstream portion of synthetic DNA
      detector (DO) with poly-A region (CP5)

<400> SEQUENCE: 31
aaaaactact acctcacgga ac                                              22

<210> SEQ ID NO 32
<211> LENGTH: 18
<212> TYPE: DNA
<213> ORGANISM: Artificial Sequence
<220> FEATURE:
<223> OTHER INFORMATION: partial downstream portion of synthetic DNA
      detector (DO) with noncomplementary region (CP3)

<400> SEQUENCE: 32
taagagaact atacaacc                                                   18

<210> SEQ ID NO 33
<211> LENGTH: 50
<212> TYPE: DNA
<213> ORGANISM: Homo sapiens

<400> SEQUENCE: 33
aggtgtgcac ttttattcaa ctggtctcaa gtcagtgtac aggtaagccc                50

<210> SEQ ID NO 34
<211> LENGTH: 50
<212> TYPE: DNA
<213> ORGANISM: Homo sapiens

<400> SEQUENCE: 34
cgaggaagtc ccttcttaaa ggagtccaca aactcgtcac tcatcctccg                50

<210> SEQ ID NO 35
<211> LENGTH: 50
<212> TYPE: DNA
<213> ORGANISM: Homo sapiens

<400> SEQUENCE: 35
cttgtcattc cattccacca tcagcatgtg gtcggtaaat gtcttcccaa                50

<210> SEQ ID NO 36
<211> LENGTH: 50
<212> TYPE: DNA
<213> ORGANISM: Homo sapiens

<400> SEQUENCE: 36
gtgtatatct gtctatcctc aaggactgcc tgatctcagc ggcacccaca           50

<210> SEQ ID NO 37
<211> LENGTH: 50
<212> TYPE: DNA
<213> ORGANISM: Homo sapiens

<400> SEQUENCE: 37
tgcccaagga ctattctgac tttaagtcac ataatcgatc ccaagcactc           50

<210> SEQ ID NO 38
<211> LENGTH: 50
<212> TYPE: DNA
<213> ORGANISM: Homo sapiens

<400> SEQUENCE: 38
ttcttccgta ctggcctggg aactctcctg ttctttgatc agagatgtag           50

<210> SEQ ID NO 39
<211> LENGTH: 50
<212> TYPE: DNA
<213> ORGANISM: Homo sapiens

<400> SEQUENCE: 39
tattctcggt tttctgtgca cacctggaat tgggcaaatg tgttcagctc           50

<210> SEQ ID NO 40
<211> LENGTH: 50
<212> TYPE: DNA
<213> ORGANISM: Homo sapiens

<400> SEQUENCE: 40
ttttccatcc ccagcaaatc ctttcaaaca ctgacatgtg gcatcctctc           50

<210> SEQ ID NO 41
<211> LENGTH: 50
<212> TYPE: DNA
<213> ORGANISM: Homo sapiens

<400> SEQUENCE: 41
agcaaaagga acattttgta tgtgtgtgtg actgaacata actgtaggct           50

<210> SEQ ID NO 42
<211> LENGTH: 50
<212> TYPE: DNA
<213> ORGANISM: Homo sapiens

<400> SEQUENCE: 42
gcgacaaaac cgagtcacat cagtaatagt atgcatcggc aaaagggcat           50

<210> SEQ ID NO 43
<211> LENGTH: 50
<212> TYPE: DNA
<213> ORGANISM: Homo sapiens

<400> SEQUENCE: 43
ccattgatga caagcttccc gttctcagcc ttgacggtgc catggaattt           50

<210> SEQ ID NO 44
<211> LENGTH: 50
<212> TYPE: DNA
<213> ORGANISM: Homo sapiens

<400> SEQUENCE: 44
ctctctgaaa ccctcaacgg caactggtga acggtaacac tgattgccca        50

<210> SEQ ID NO 45
<211> LENGTH: 50
<212> TYPE: DNA
<213> ORGANISM: Homo sapiens

<400> SEQUENCE: 45
ctggcatccg tcaggaagtg tgggcctttg tgttttgatg ctacacatgt        50

<210> SEQ ID NO 46
<211> LENGTH: 50
<212> TYPE: DNA
<213> ORGANISM: Homo sapiens

<400> SEQUENCE: 46
ccctgcccca gcctgatgga accctctgtt tacacacctg ctagcccctt        50

<210> SEQ ID NO 47
<211> LENGTH: 50
<212> TYPE: DNA
<213> ORGANISM: Homo sapiens

<400> SEQUENCE: 47
tgagcctatt ctcacagatc tccttttgtc ggccttggtt gggacaacat        50

<210> SEQ ID NO 48
<211> LENGTH: 50
<212> TYPE: DNA
<213> ORGANISM: Homo sapiens

<400> SEQUENCE: 48
tccgtttctg ccagtgtgtc ttccaaggca gctttcatgc tcagctgtga        50

<210> SEQ ID NO 49
<211> LENGTH: 50
<212> TYPE: DNA
<213> ORGANISM: Homo sapiens

<400> SEQUENCE: 49
ctttgaatat attgactgaa aacgtcttcg tgacacggac gtgctcctcc        50

<210> SEQ ID NO 50
<211> LENGTH: 50
<212> TYPE: DNA
<213> ORGANISM: Homo sapiens

<400> SEQUENCE: 50
atcgagaggc tgcttccgtt ttatactgat tgaactgtgt ctccacgtcg        50

<210> SEQ ID NO 51
<211> LENGTH: 50
<212> TYPE: DNA
<213> ORGANISM: Homo sapiens

<400> SEQUENCE: 51
tacattatgt acaccattta caggagggta acacaaacct tgacaggtag        50

<210> SEQ ID NO 52
<211> LENGTH: 50
<212> TYPE: DNA
<213> ORGANISM: Homo sapiens

```
<400> SEQUENCE: 52
tgcatagcat ttacacacag agccactgct gcacagcaca agagtatctg            50

<210> SEQ ID NO 53
<211> LENGTH: 50
<212> TYPE: DNA
<213> ORGANISM: Homo sapiens

<400> SEQUENCE: 53
aagcgtgtct gaggtgtccg gtggaggtgg cagccgagct ctgggactaa            50

<210> SEQ ID NO 54
<211> LENGTH: 50
<212> TYPE: DNA
<213> ORGANISM: Homo sapiens

<400> SEQUENCE: 54 gcatcccta aggcttggaa ccctttatac atcttggtca tcttgatctc             50

<210> SEQ ID NO 55
<211> LENGTH: 50
<212> TYPE: DNA
<213> ORGANISM: Homo sapiens

<400> SEQUENCE: 55
gatggtgtgg tggcggcagc gtggtttctg tatcgatcgt tctgtatcag            50

<210> SEQ ID NO 56
<211> LENGTH: 50
<212> TYPE: DNA
<213> ORGANISM: Homo sapiens

<400> SEQUENCE: 56
aggagccgct aatagctaca gtggaaggaa atactgattc caggaggcaa            50
```

METHOD OF NUCLEIC ACID SEQUENCE DETECTION

CROSS-REFERENCE TO RELATED APPLICATIONS

This application is a continuation-in-part of Ser. No. 15/954,546, entitled Focal Gene Expression Profiling of Stained FFPE Tissues with Spatial Correlation to Morphology, filed Apr. 16, 2018, which is a continuation-in-part of Ser. No. 15/387,650 entitled Ligation Assays in Liquid Phase, filed Dec. 22, 2016 and published as US 2017/0101671, which is a continuation-in-part of international application PCT/US16/14999, filed Jan. 26, 2016 and published as WO 2016/123154, which was a continuation-in-part of Ser. No. 14/788,670, filed Jun. 30, 2015, and issued as U.S. Pat. No. 9,856,521 on Jan. 2, 2018, which claimed the benefit of priority of U.S. provisional application Ser. 62/108,161, filed Jan. 27, 2015.

This application is also a continuation-in-part of the aforementioned application Ser. No. 15/387,650, which is also a continuation-in-part of Ser. No. 14/788,670, filed Jun. 30, 2015, and issued as U.S. Pat. No. 9,856,521 on Jan. 2, 2018, which claimed the benefit of priority of U.S. provisional application Ser. 62/108,161, filed Jan. 27, 2015.

This application is also a continuation-in-part of Ser. No. 15/920,381, entitled Profiling Expression at Transcriptome Scale, filed Mar. 13, 2018, which is a divisional of Ser. No. 14/595,069, filed Jan. 12, 2015, and issued as U.S. Pat. No. 9,938,566, which was a continuation-in-part of Ser. No. 14/480,525, entitled Attenuators, filed Sep. 8, 2014, and issued as U.S. Pat. No. 9,957,550.

The contents of the aforementioned applications are incorporated herein in their entirety.

STATEMENT OF GOVERNMENT SUPPORT

This invention was made with government support under grants R43 & R44 ES024107, R43 & R44 HG007339, R43 & R44 HG008917, R43 & R44 HG007815, R33CA183699, awarded by the National Institutes of Health (NIH). The government has certain rights in the invention.

TECHNICAL FIELD

This invention relates to molecular biology, and more particularly to assays for detecting nucleic acid sequences in samples.

SUMMARY OF THE INVENTION

The invention provides methods and kits for detecting target nucleic acid sequences in samples. A target sequence can have a downstream region (DR) and an upstream region (UR). The samples are contacted with detector oligos to hybridize specifically to the target sequences. A downstream detector oligo (DDO or DD) can have a complementary downstream region (DR'). An upstream detector oligo (UDO or UD) can have a complementary upstream region (UR'). If both the DDO and UDO are specifically hybridized to the DR and UR of a target sequence, they can be ligated. For some samples, the ligated detectors are labeled with a barcode sequence. The labeled detectors can be further labeled with additional barcodes for combinations of samples. The barcoded ligation product indicates the presence of the target sequence and identifies the sample.

In various embodiments, the barcodes can be added by enzymatic or chemical methods, such as ligases or "click" chemistry addition. Certain barcodes can be added to different sets of samples, or combinations of samples in various splitting and mixing schemes to uniquely identify samples. The barcodes can be added directly or indirectly to the upstream or downstream portion of ligated detectors, or in any order. Ligation template linkers (LTLs) can facilitate addition of successive barcode sequences. In other embodiments, bridge oligos or horseshoe (HS) oligos can be provided to promote amplification of the barcodes for detection. The components of the assay can be configured to resist selected nucleases.

Treatment with an exonuclease, such as an exonuclease with single-stranded 3'-to-5' activity, can be used at various stages of the method to remove undesired components, such as nonbound or excess DD and UD detectors as in FIG. 2e. Detectors that are nonspecifically or incompletely hybridized to target sequences can be degraded by the exonuclease or will not result in ligation or amplification product, as in FIG. 2f.

As shown in FIG. 2g, it may be desirable to provide predetermined quantities of attenuator oligonucleotides such as UR2' (or alternatively UR2) to lessen the formation of product resulting from certain high-abundance target sequences (HATs).

Figure 2H:
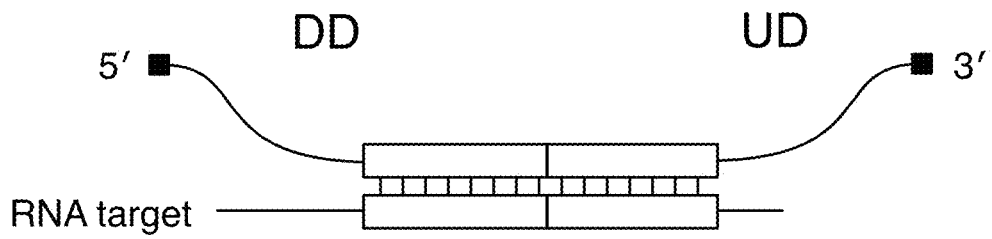
FIG. 2a shows an "anchored" version of the assay where the UD is configured with a second complementary region (UR2' or "anchor") separated by a noncomplementary region (CP1). The DD and UD can hybridize to a target sequence as in FIG. 2b, forming a hybridization complex (HC) providing a substrate for ligation at the junction (L) between DR' and UR'. In some methods, an optional nuclease, such as a 3'- or 5'-single-stranded exonuclease, is provided at various stages to remove undesired or leftover reactants. After ligation.
FIG. 2c shows the ligation product (LP) can be amplified by primers to yield amplification products (AP) in FIG. 2d.

FIG. 2h shows a pair of detectors that are configured to have a modification at one end to resist exonucleases that degrade single-stranded (ss) DNA. The UD has a modification at the 3' end that resists degradation of the detector by an exonuclease having 3' activity on DNA single strands. Alternatively, the DD can have a 5' modification to resist degradation by a 5'-ss-exonuclease.

Figure 2I:
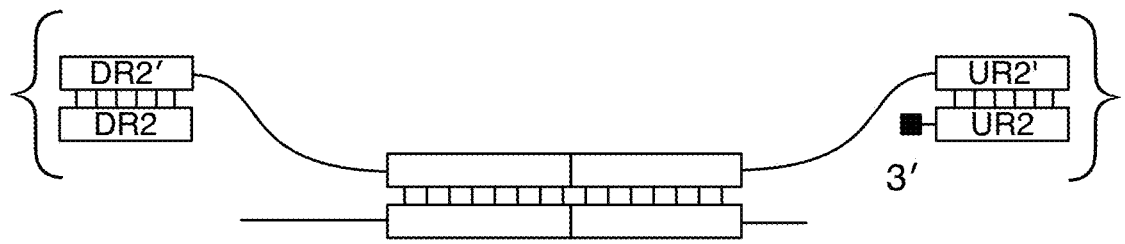
Figure 2J:
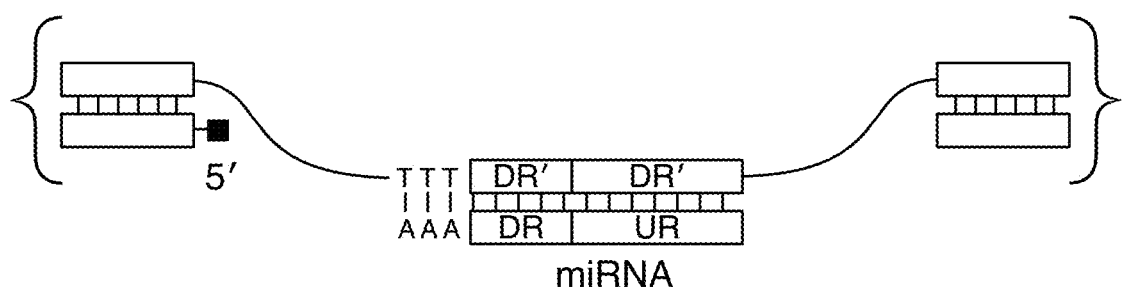

FIGS. 2i and 2j illustrate detectors that are configured to resist exonucleases by being hybridized to a protector oligo, such as ones having sequence DR2 or UR2 that bind to corresponding DR2' and UR2' sequences of the detectors, presenting double-stranded structures at either end. The protectors can themselves be 5'- or 3'-modified to resist exonucleases, as shown. FIG. 2j also illustrates a target sequence (3'-DR-UR-5') that is relatively short, such as a microRNA, where the target has been polyadenylated at its 3' end. The DD features a complementary poly-T portion adjacent to the DR'.

Figure 3A:
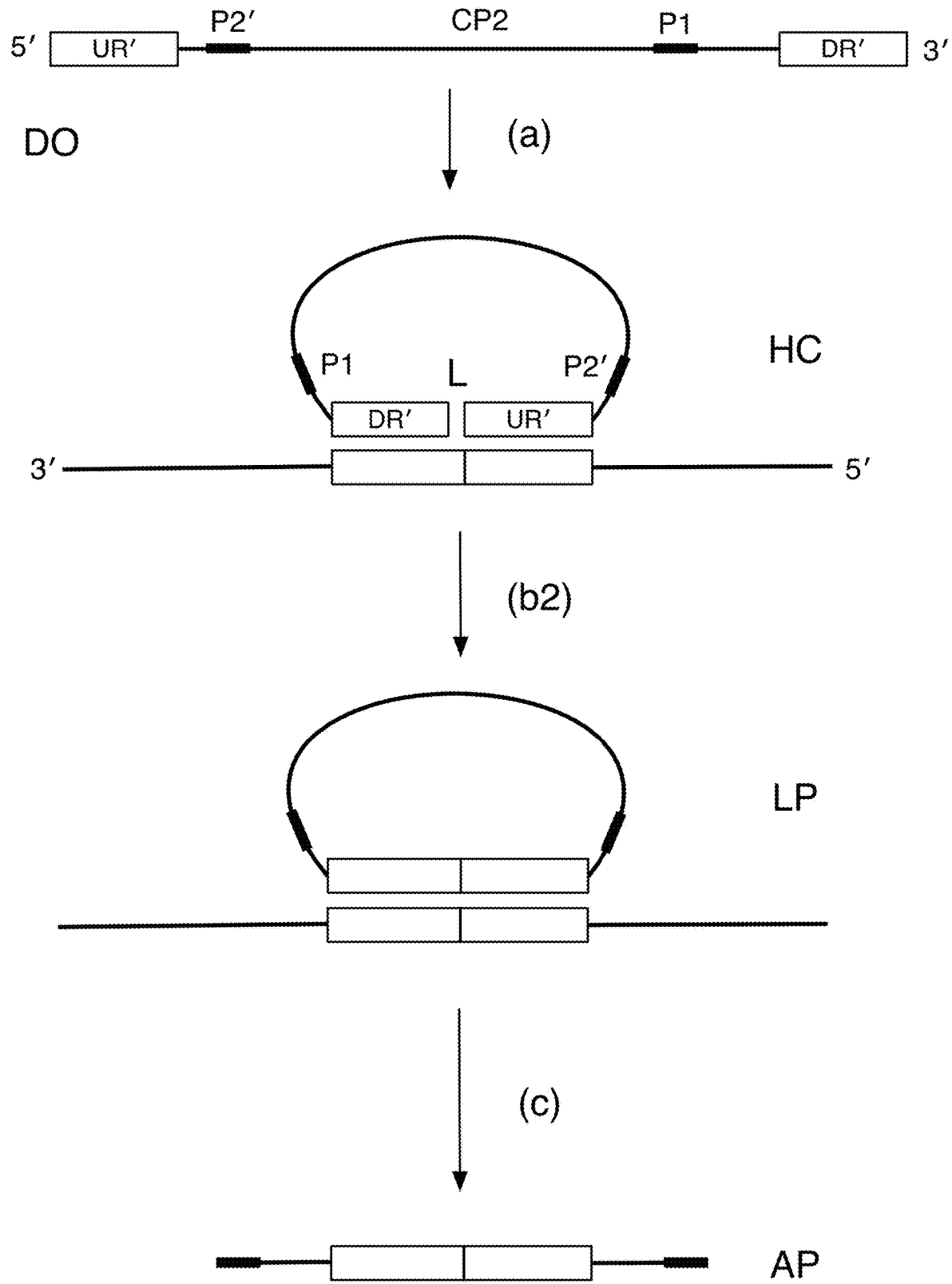

FIG. 3a depicts a circularizable assay design of the invention using a detector oligo probe (DO) that can (a) hybridize via DR' and UR' regions to a target sequence, forming a (noncovalently) circularized structure. After treatment with a nuclease and ligase, a circularized ligation product can then be (c) amplified. FIGS. 3b, 3c, and 3d illustrate partially hybridized DO detectors, detectors hybridized to non-target sequences, or nonspecifically hybridized detectors, which can be digested by nucleases or be unsuitable for exponential amplification.

Figure 4:
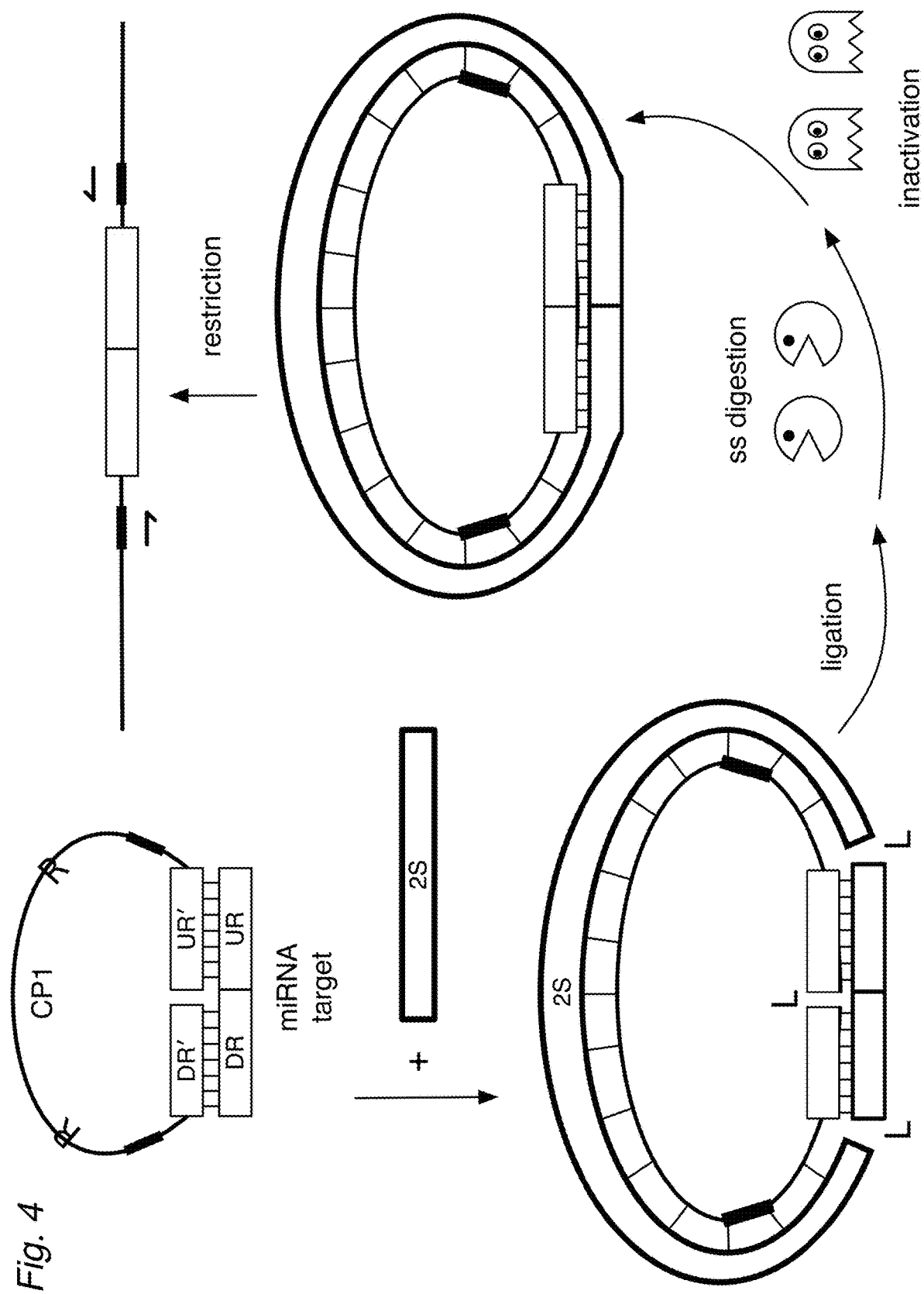

FIG. 4 shows an assay of the invention where a (universal) second strand (2S) is provided during hybridization so that the target (DR-UR), DO, and the 2S form a circularized, double-stranded structure. Treatment with ligase results in a covalently circularized ligation product. Optionally, ss-nucleases can be used to degrade excess detectors and hybridization complexes that are not specific for the target. The nucleases can be inactivated. If desired, the circularized structure can be linearized, for example by a restriction endonuclease.

Figure 5A:
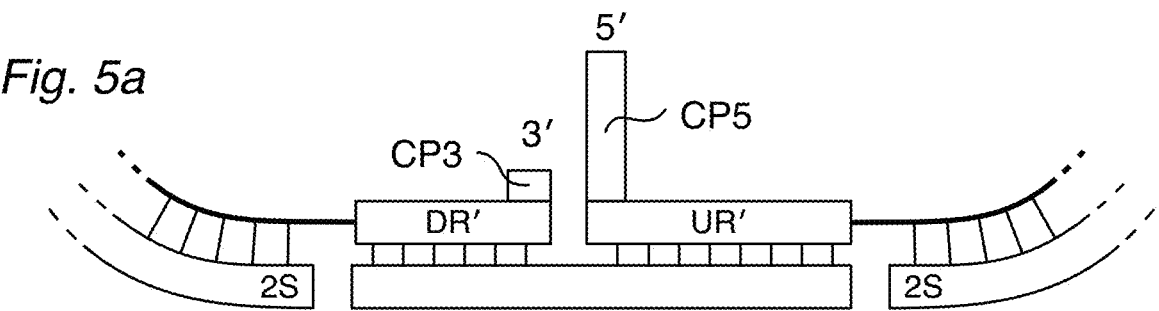
Figure 5B:
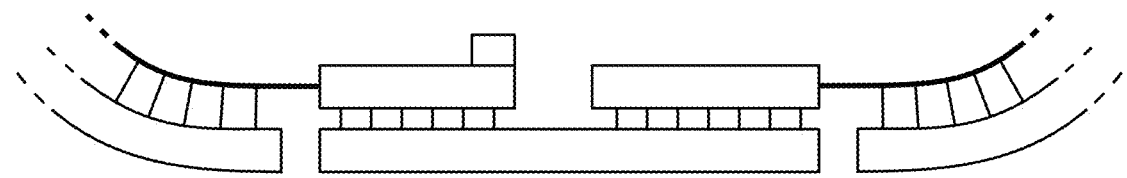
Figure 5C:
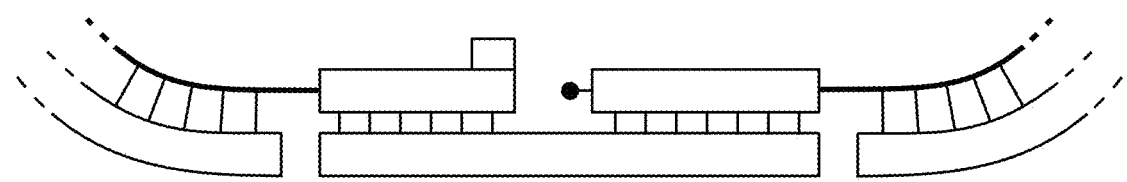
Figure 5D:
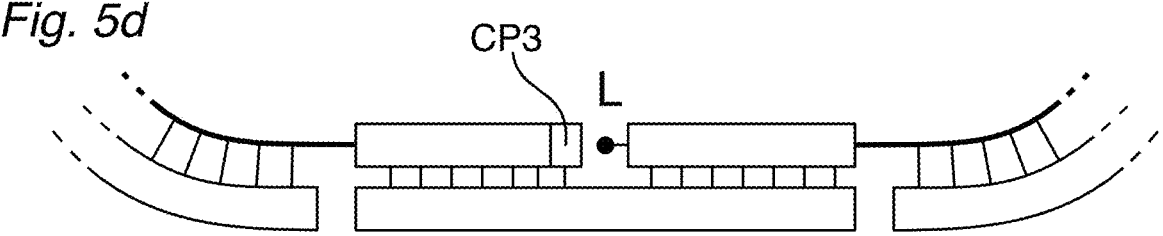

FIG. 5a shows a detailed view of a hybridization complex using a variant circularizable DO having a short noncomplementary flap (CP5) on its 5' end, and optionally a short noncomplementary sequence (CP3) on the 3' end. FIG. 5b shows the hybridization complex after the CP5 is removed by a flap nuclease, such as Fen-1. If desired, the 5' end can be phosphorylated, as in FIG. 5c. FIG. 5d illustrates how CP3 can fill in the gap left by Fen-1, so that the DO can be ligated into circularized form as in FIG. 5e. The noncomplementary CP5 and/or CP3 flaps can be incorporated in any of the DD and UD designs.

FIG. 6a provides target sequences (SEQ ID NOs: 33-56) used to design detectors for mRNA expression products for 24 human genes of interest. The genes were selected to demonstrate detection over an expected range of 6 orders of magnitude in abundance, with 10, 1, and 0.1 ng sample RNA input. The number of amplified ligation products, confirmed by sequencing, are shown for anchored detector designs (FIGS. 6b, 6c, and 6d) and circularizable designs (FIGS. 6e, 6f, and 6g). The x-axis is for the first technical replicate; the y-axis is for the second replicate.

Figure 7:
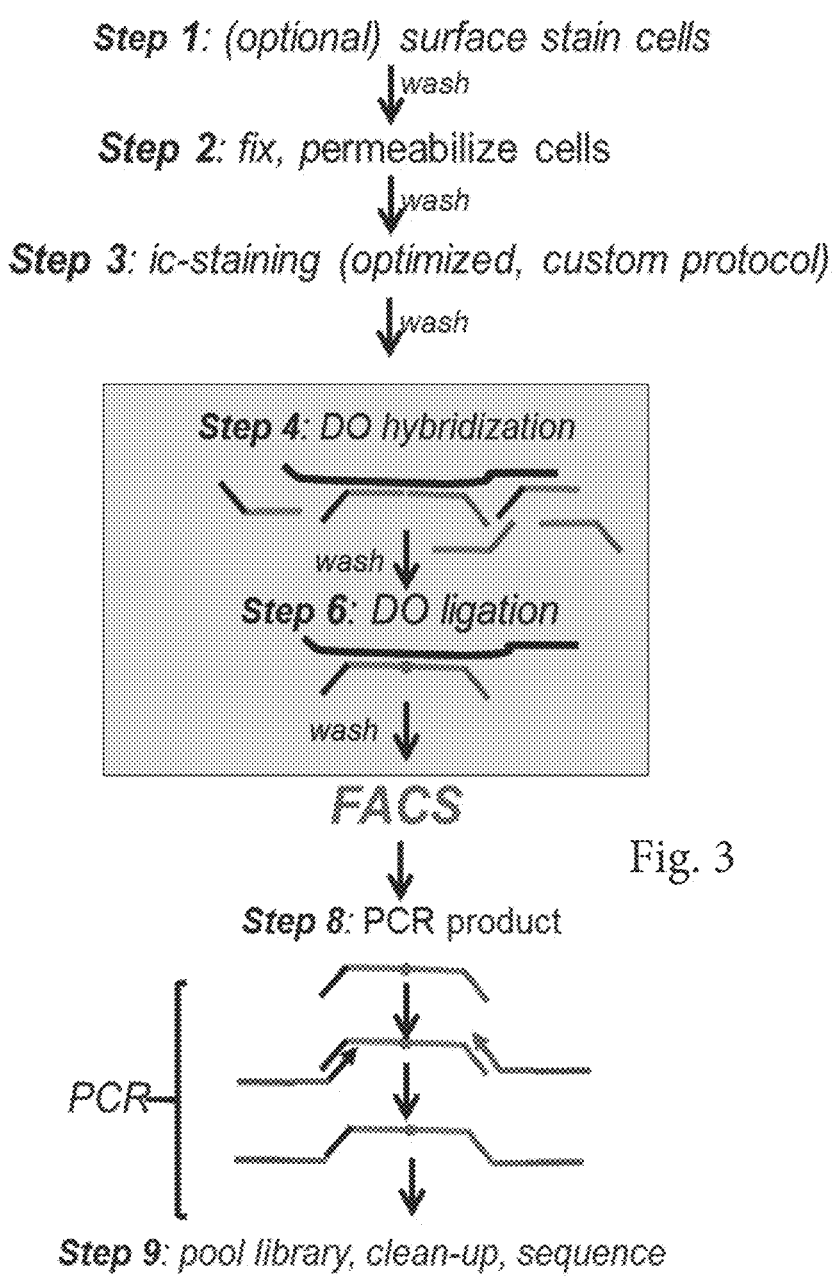

FIG. 7 shows a modified version of the TempO-Seq™ assay that can be performed after antibody-staining, before flow cytometry sorting (FACS) and PCR.

Figure 8:
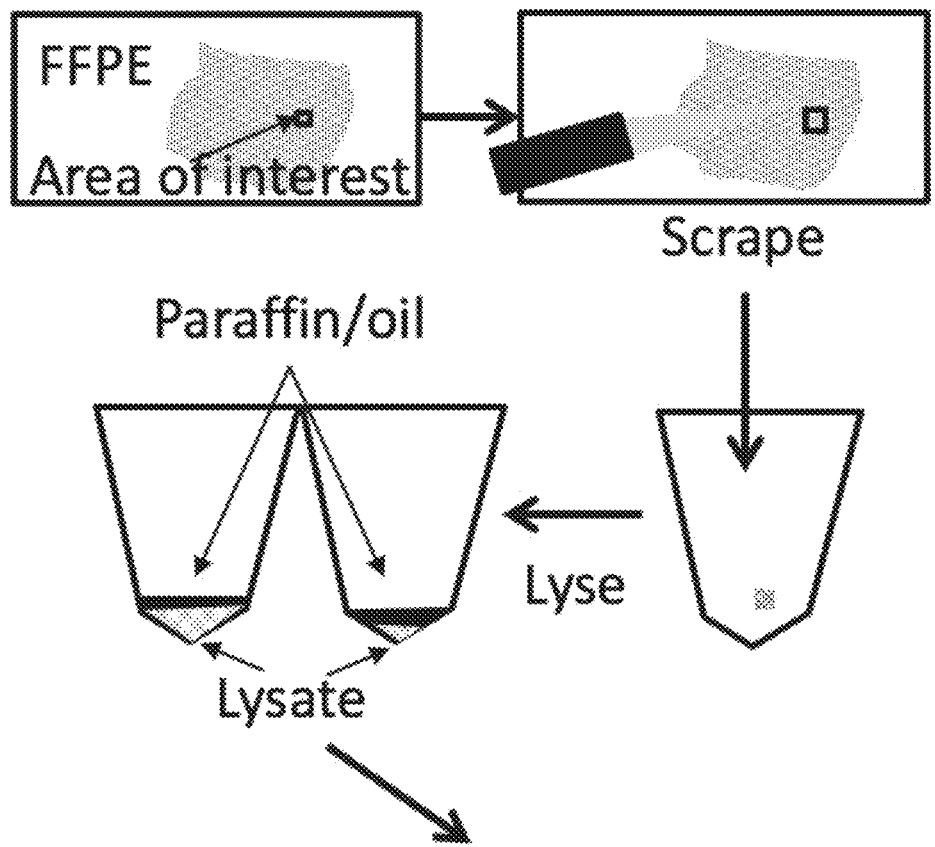

FIG. 8 depicts steps for processing FFPE samples in the "standard" TempO-Seq™ FFPE protocol.

Figure 9:
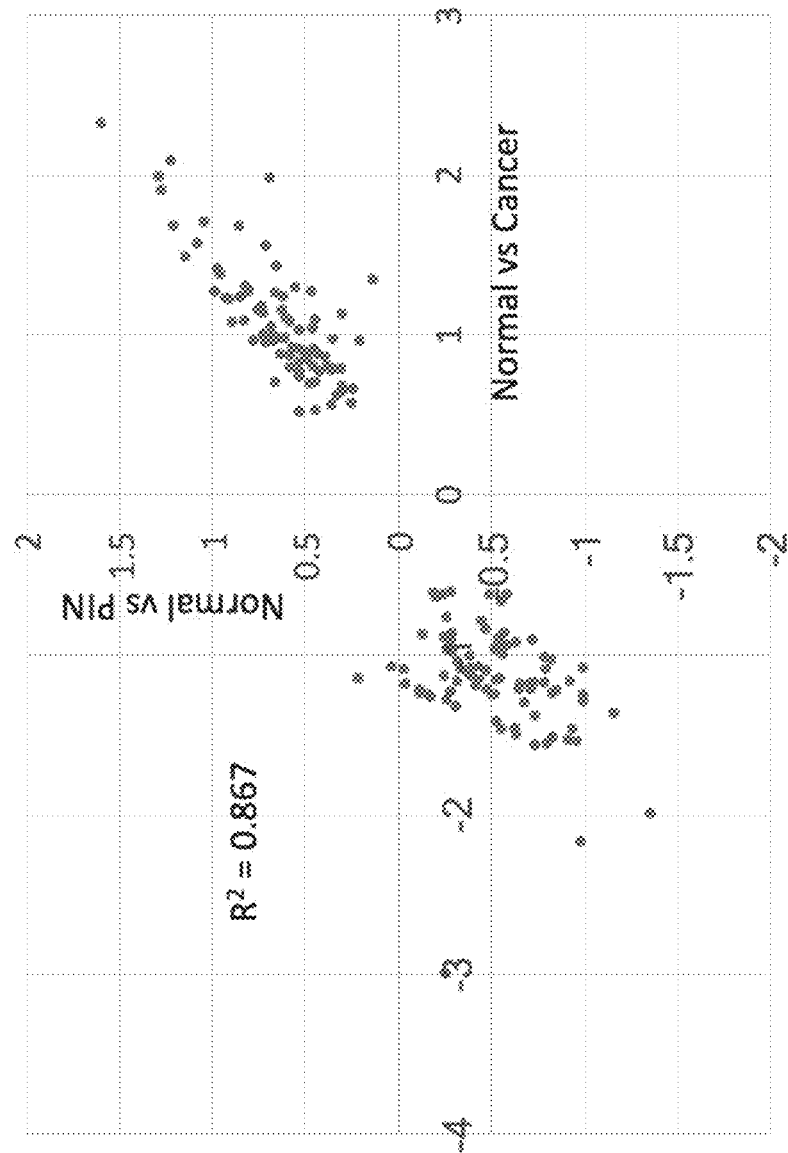

FIG. 9 compares expression between normal and PIN (prostatic intraepithelial neoplasia) versus normal and cancer, plotting for statistically significant genes, as discussed in Example 5.

Figure 10:
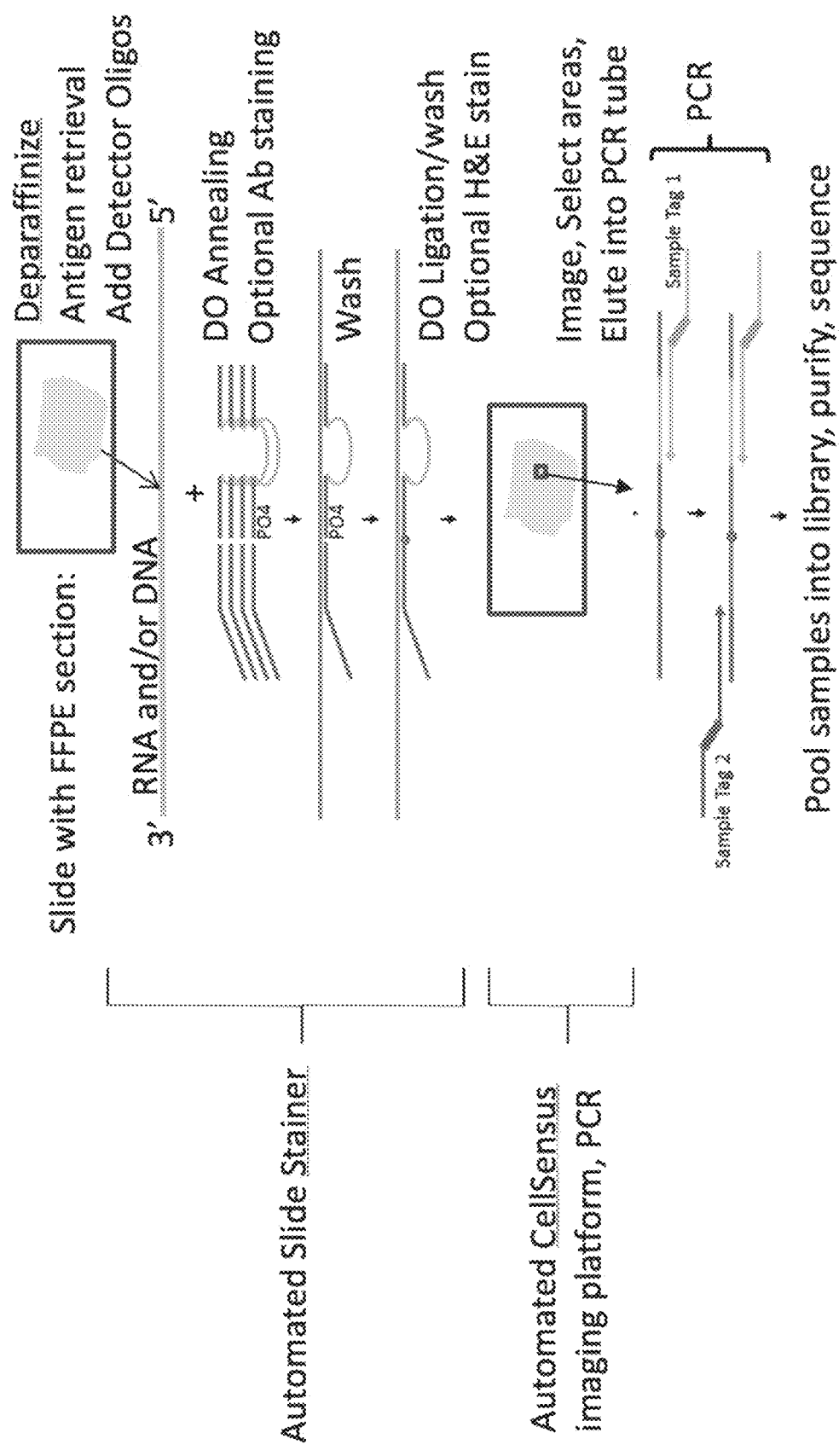

FIG. 10 illustrates an automated in situ assay process.

Figure 11:
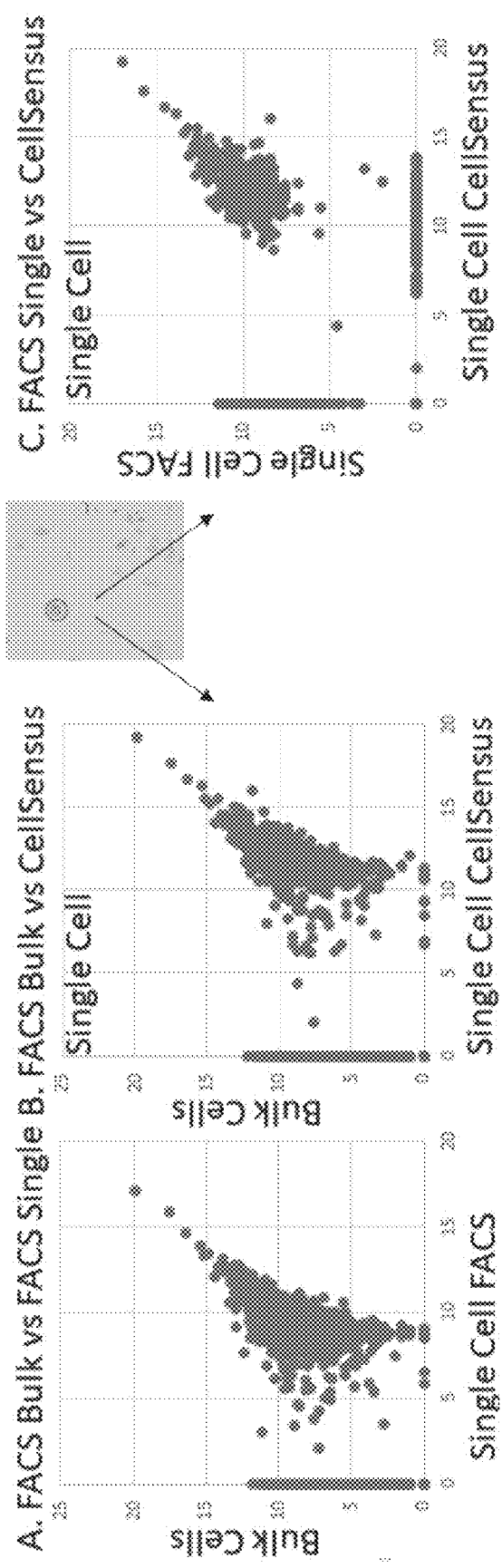

In FIG. 11, panel (A) shows the correlation of an assay of bulk 200 cells versus a single FACS-sorted cell. Panel (B) shows the correlation of the same 200-cell bulk and a single cell profiled using the CellSensus™ instrument. Panel (C) shows correlation of one single cell isolated by FACS versus a single cell isolated by the CellSensus™ instrument.

FIG. 12 shows images of a breast FFPE before and after automated elution by the CellSensus™ instrument, showing that a reagent in the eluent destains the exposed area, providing a positive record of the profiled area.

FIG. 13 shows stained prostate FFPE tissue (left) and the same tissue after focal elution of a 130 µm diameter area by the CellSensus™ instrument (right). The destained area in the center demonstrated exquisite elution and collection from minute spatial areas. The precision of the collection areas is demonstrated in Example 9 and Table 3, where the individual areas of cancer tissue, normal epithelia tissue, and stroma, were distinguished by sharply different gene expression profiles.

Figure 14:
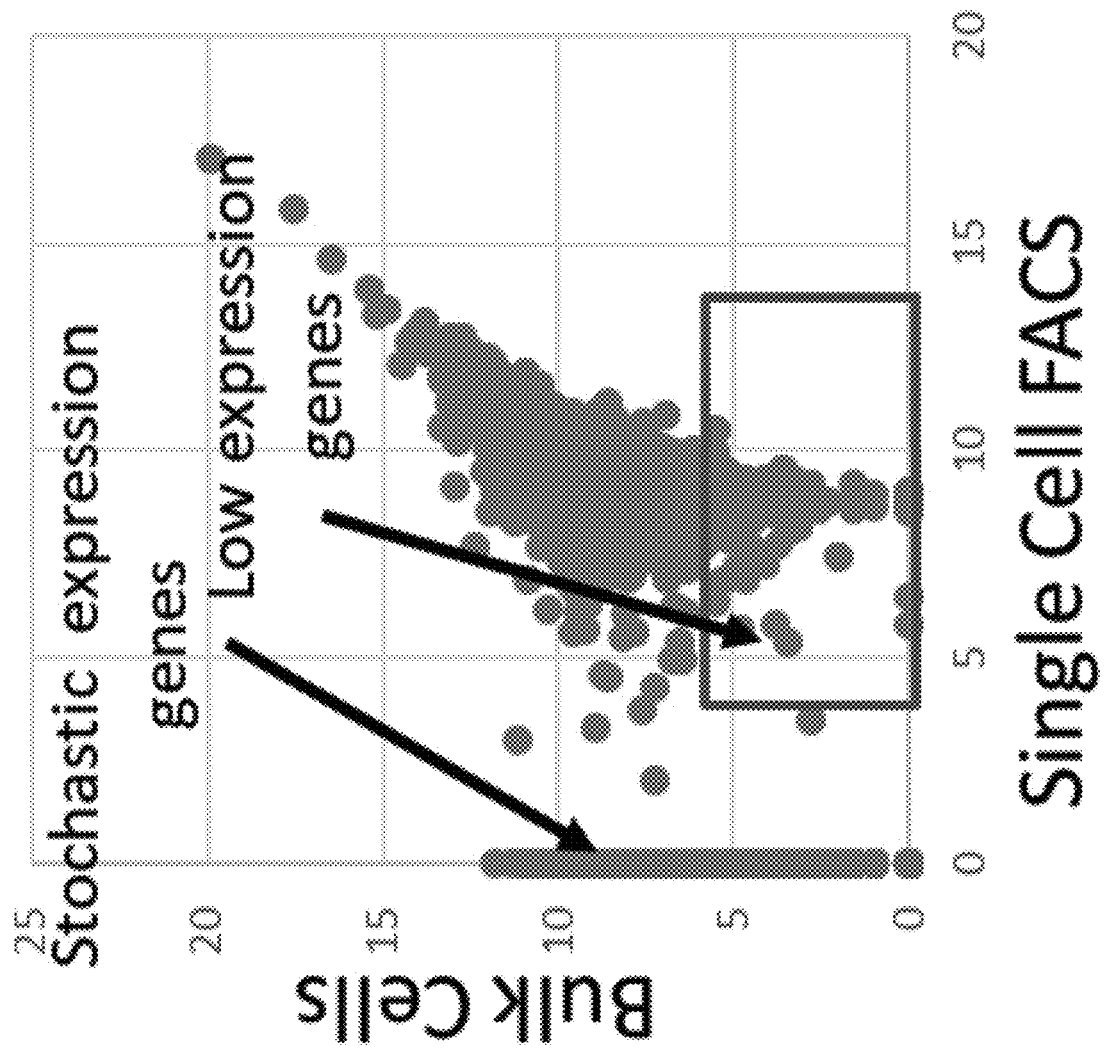

FIG. 14 shows the number of reads of detected expression sequences obtained by using a TempO-Seq™ whole transcriptome assay for bulk cells compared with a single-cell FACS. MCF-7 cells were processed through an in situ TempO-Seq™ assay and then either assayed in bulk (1000 sorted cells) or sorted as single cells. The correlation is shown as $\log_2$ scaled read counts. As shown, low-abundance RNAs are measurable from single cells. At the instant cells are fixed, some genes are not expressed, due to the biological stochastic nature of expression.

Figures 15A, 15B:
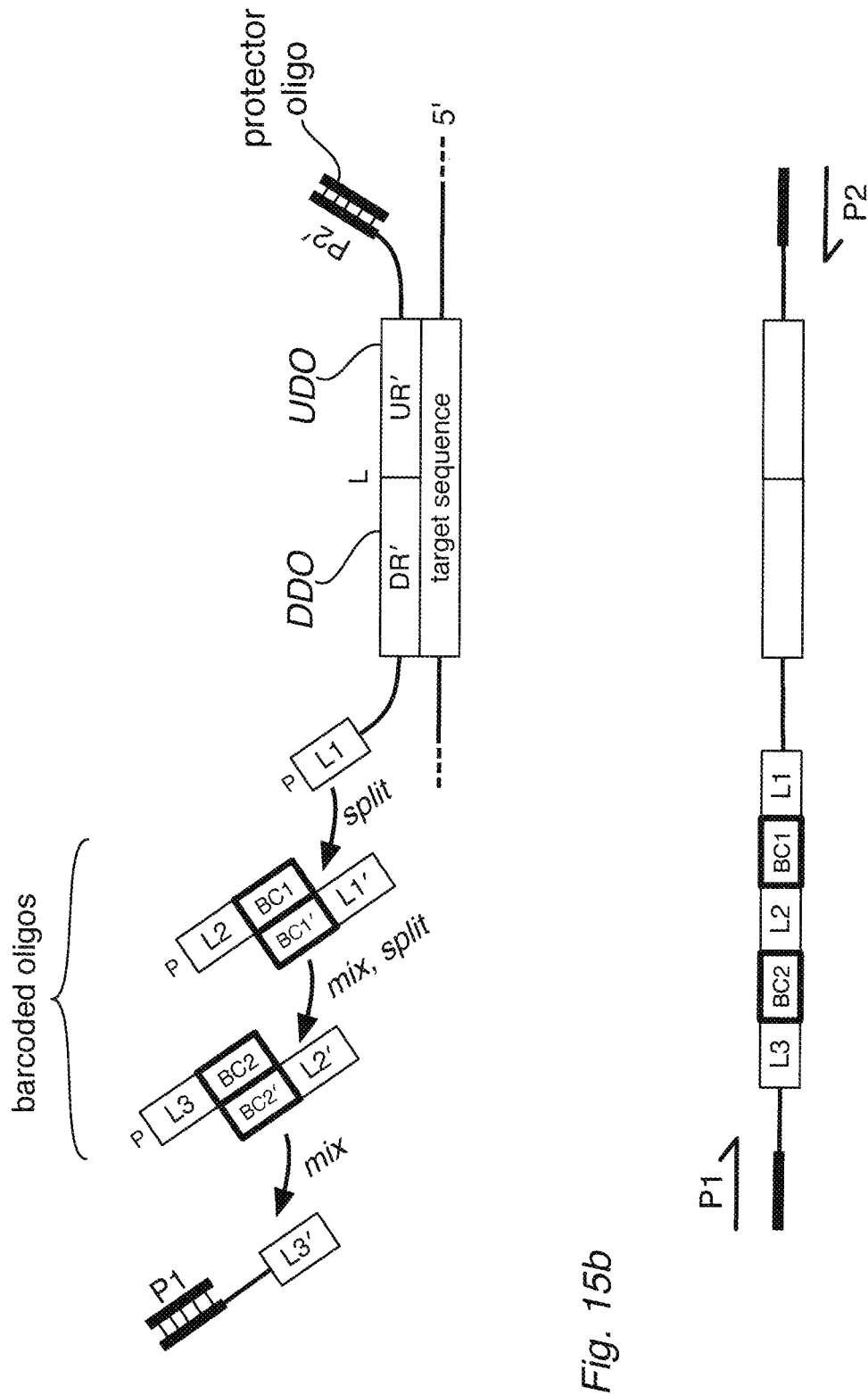

FIG. 15a schematically shows simple templated ligation of barcoded oligos. A target sequence is shown to represent one sample among a large population of samples. A downstream detector oligo (DDO), having a L1 portion and a DR' region, and an upstream detector oligo (UDO), having a UR' region and a P2' amplification region, are hybridized to the target sequence to form a hybridization complex, where the ligation junction is indicated by L. (A ligation step is not shown.) The DDO is optionally phosphorylated at the 5' end. An optional protector oligo may be hybridized to the P2' portion to resist single-stranded exonucleases. The population of samples is split into subpopulations and a first barcoded oligo (exemplified by 5'-P-L2-BC1-3': 3'-BC1'-L1'-5') is provided where BC1 represents a unique barcode sequence for each subpopulation. The first barcoded oligos are ligated to the DDOs in the subpopulations via the L1 linker sequence. The subpopulations are thoroughly mixed and subdivided into a second series of subpopulations. A second series of barcoded oligos is provided, each having a unique barcode sequence (indicated by BC2) for each subpopulation in the second series of subpopulations. Alternatively, BC2 and BC1 can be regarded as a single identification barcode in two discontinuous sequences. The second barcoded oligo is then ligated to the first barcoded oligo, via an L2 linker sequence. The subpopulations in the second series are mixed, and an oligo, having a P1 amplification sequence, is ligated via an L3 sequence. The final ligation product serves to indicate the detection of the DR-UR target sequence in samples, each of which can be individually barcoded in orthogonal sets of subpopulations. The barcoded ligation product may be amplified using primers P1 and P2 as shown in FIG. 15b.

Figure 16:
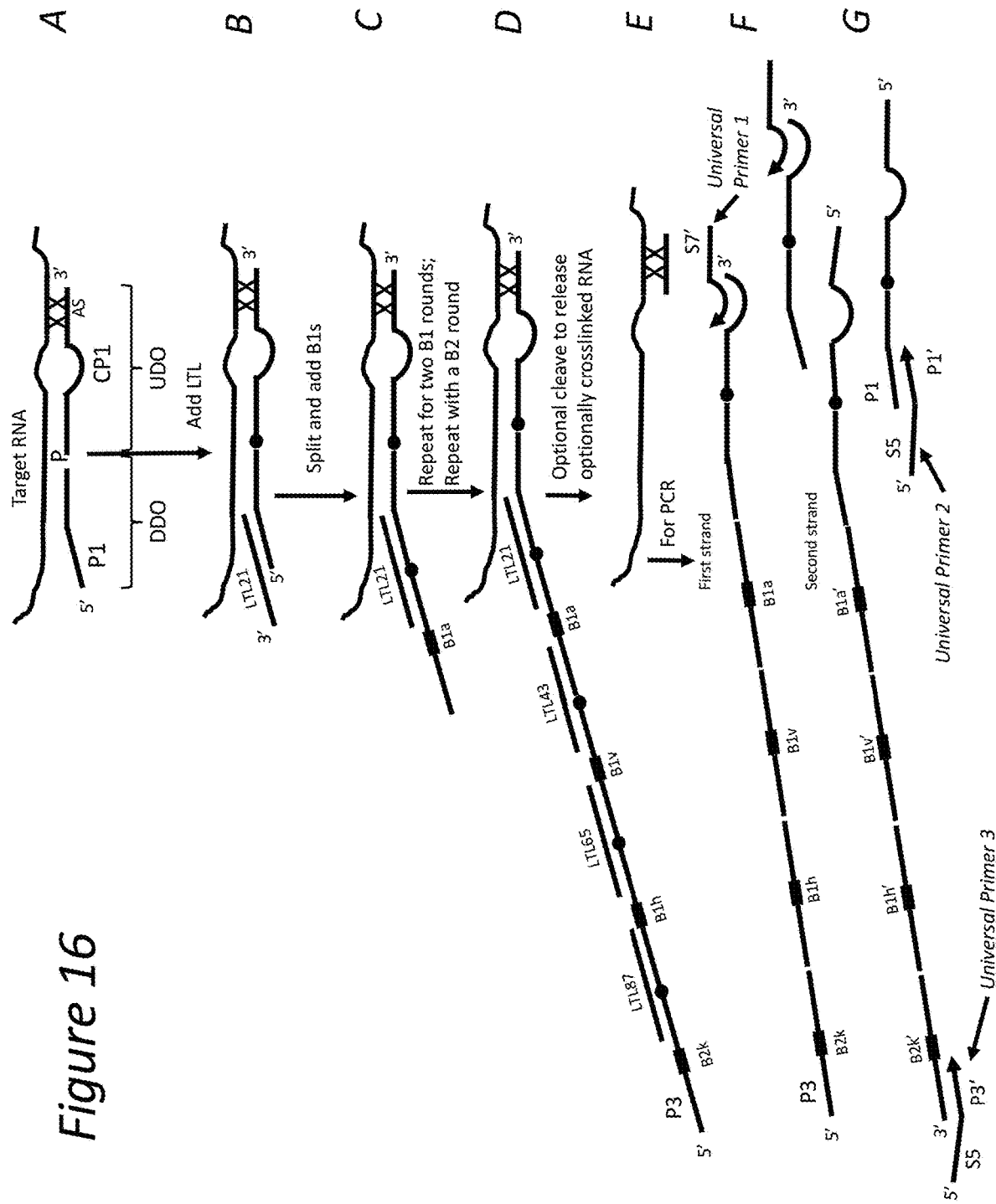

FIG. 16 illustrates a similar workflow for adding barcodes to a ligation product using templated ligation. Optional nuclease and wash steps are not shown. In part A, a population of cells is fixed, and a target RNA sequence from one cell of the population is shown, hybridized to a downstream detector (DD) and an upstream detector (UD). The DD contains a P1 amplification sequence and a hybridization region (such as DR'). The UD is phosphorylated (P) and can have two hybridization regions: a UR' and an optional UR2' (marked "AS"), as well as an optional noncomplementary region CP1, which may contain a P2' sequence. A detector may be crosslinked to the RNA target, shown by XX. The hybridization complex is then treated with a ligation reagent, such as a ligase, to ligate the DD to the UD, as shown in part B. A ligation template linker (LTL) is added and allowed to hybridize to a detector.

The cells in the population are then split into subpopulations for round 1 of barcoding. For example, a sample of cells is split into 96 wells of a microplate. One of a set of different Barcode 1 (B1) oligos (described further below) are added to the well for each subpopulation, so that each subpopulation receives a unique B1 oligo. The B1 oligo can hybridize to a portion of the LTL, as shown in part C. As an example, a B1 oligo can have unique barcode sequence B1a to be added to one subpopulation of cells in a well; B1 barcoded oligos having other barcodes B1b, B1c, B1d etc. can be added to other subpopulations of cells in other wells. Excess and nonhybridized B1 oligos are removed, and the B1 is ligated to the detectors (DD and UD). The subpopulations are mixed together and independently split into a second round of subpopulations. A second set of B1 oligos (e.g. having B1a, B1b, B2c, etc.) are added to each subpopulation and ligated as before. The second round of subpopulations are mixed and independently split into a third round of subpopulations. A third set of B1 oligos are added and ligated. The second round of subpopulations are mixed and independently split into a third round of subpopulations. Finally, a set of B2 oligos (described further below) are added, where the B2 set has a primer hybridization sequence (P3) at the 5' end. For example, a B2 oligo can have a barcode sequence B2a, B2b, B2c, etc. After ligating the B2 oligos, a diverse population of barcoded products is obtained, one of which is shown in part D. If desired, any crosslinked RNA can be released by cleaving the linkage, as in part E. After this last barcoding step, the well contents can be pooled, and then amplified, for example by PCR. Examples of amplification primers are shown as Universal Primers 1, 2, and 3, as in parts F and G. If desired, regions used in commercial sequencing platforms (shown as S5 and S7) can be incorporated into the primers to prepare a library for further processing and analysis.

Figure 17:
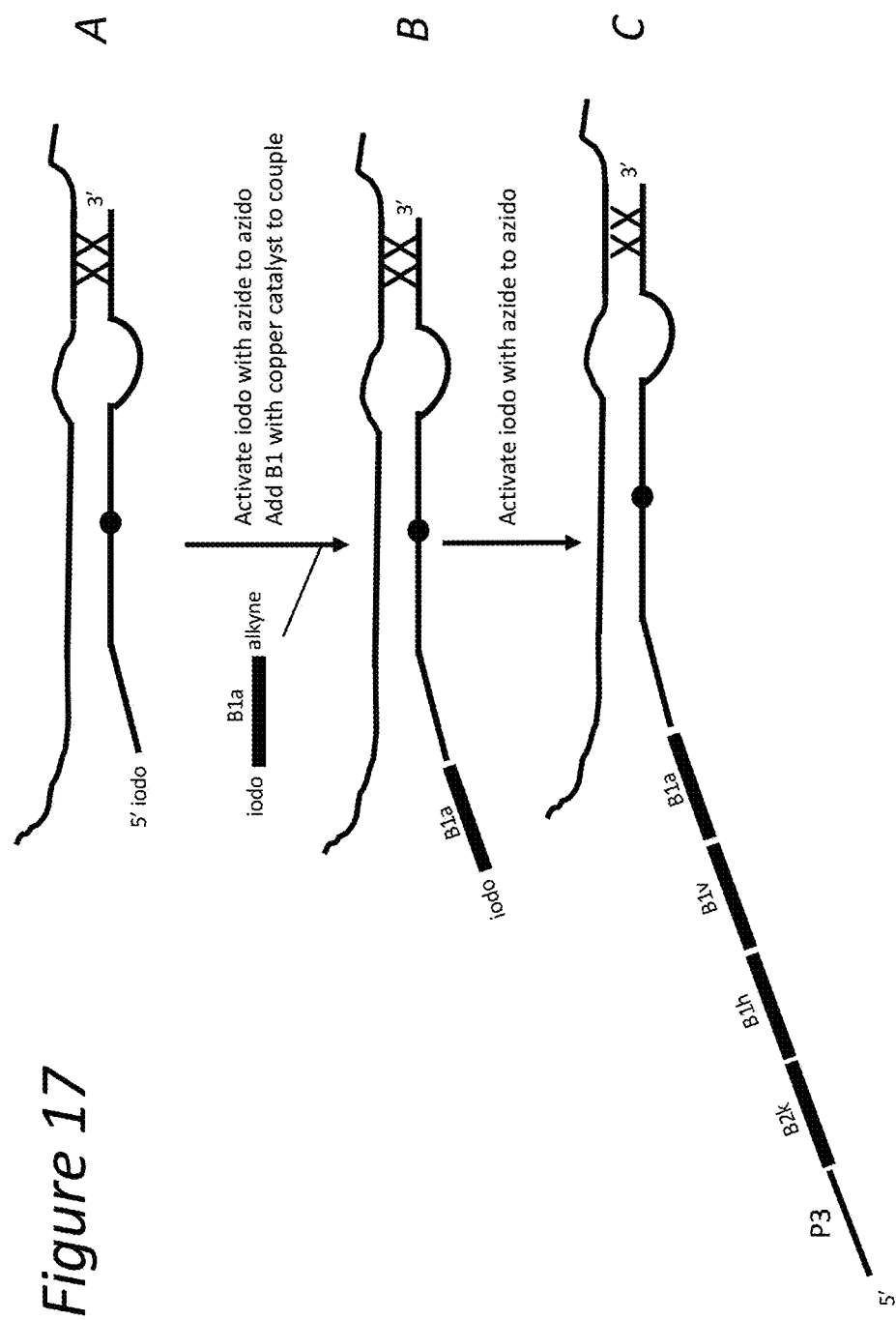

FIG. 17 illustrates an alternate embodiment for adding barcodes using click chemistry techniques, described in greater detail below. Similar to FIG. 16, part A shows UD and DD detectors are hybridized to a target RNA sequence, except the DD is modified with an iodo at the 5' end. The 5' function is activated with azide, for example, converting the iodo to an azido. The sample is split, such as transferring into 96 wells of a microplate. Each well contains a different barcode with a 3'-alkyne and 5'-iodo function, plus a copper (Cu) catalyst to promote cycloaddition of the B1 barcode to the detectors. Additional Click barcodes (such as B1v, B1h) can be added to each orthogonally split subpopulation using the Click chemistry, including a final B2 barcode oligo (shown here as barcode B2k).

Figure 18A:
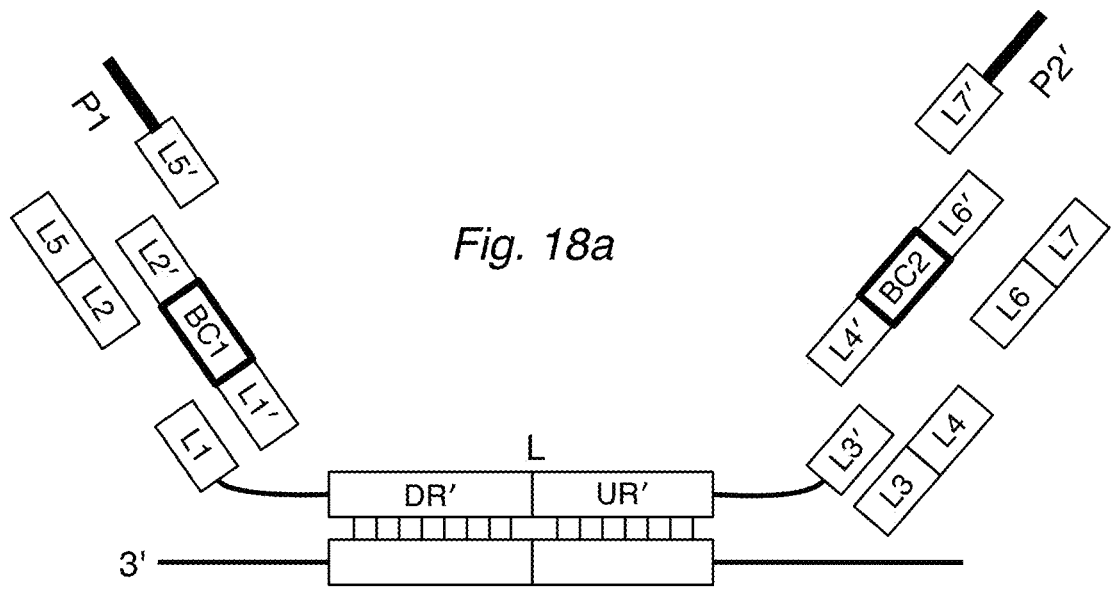

FIG. 18a illustrates an embodiment that permits addition of barcoded oligos to the downstream and upstream portions of the ligation product, in any order. The result is a strand that contains barcode sequences flanking the complement of the target sequence, optionally with amplification sequences. The barcodes can be added to anchored detector configurations as well, as in FIG. 18b. FIG. 18c shows a configuration where a detector has a BC1 sequence that can serve as a fluorophore-quencher hydrolysis probe target for an independent readout.

Figure 19A:
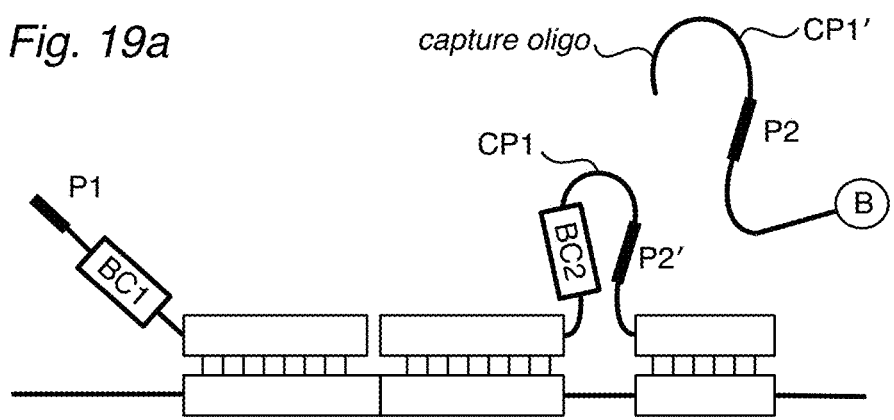
Figure 19B:
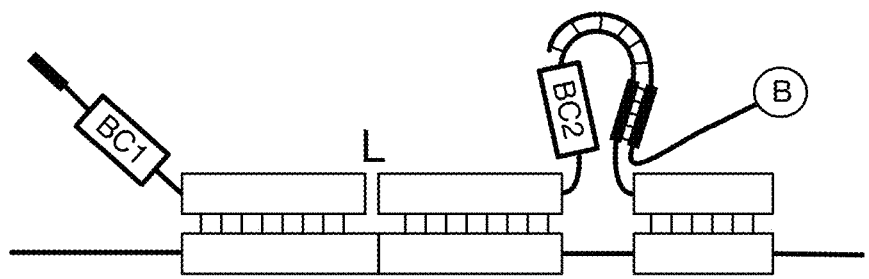
Figure 19C:
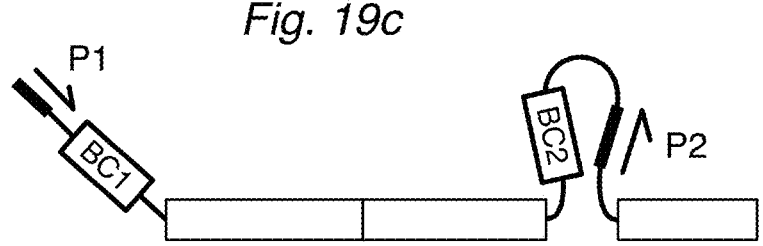

FIG. 19a illustrates an embodiment similar to FIG. 2b, where a DDO is labeled with a barcode sequence BC1 and a UDO is labeled with a barcode sequence BC2. An optional capture oligo is provided, shown with a member of a binding pair, such as biotin label B. In FIG. 19b, the capture oligo can hybridize to the P2' and/or the CP1 of the UDO loop to facilitate capture, concentration, and wash steps. The ligation product can be amplified with P1 and P2 primers, as illustrated in FIG. 19c.

Figure 20A:
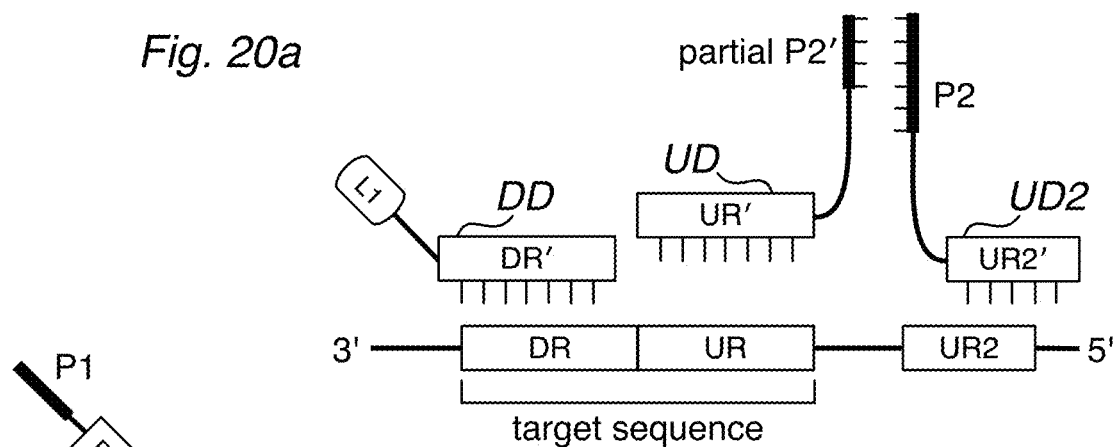
Figure 20B:
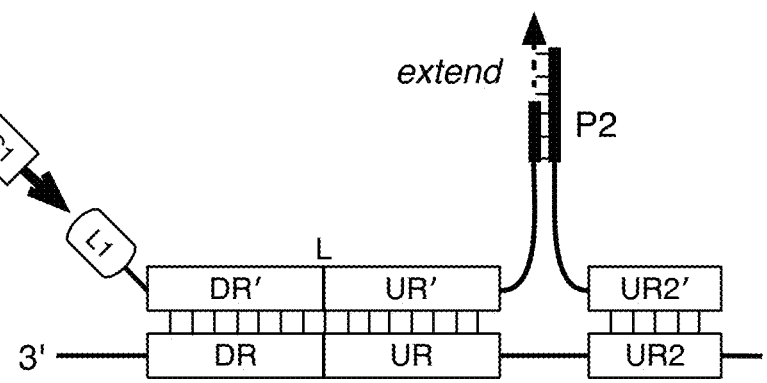
Figure 20C:
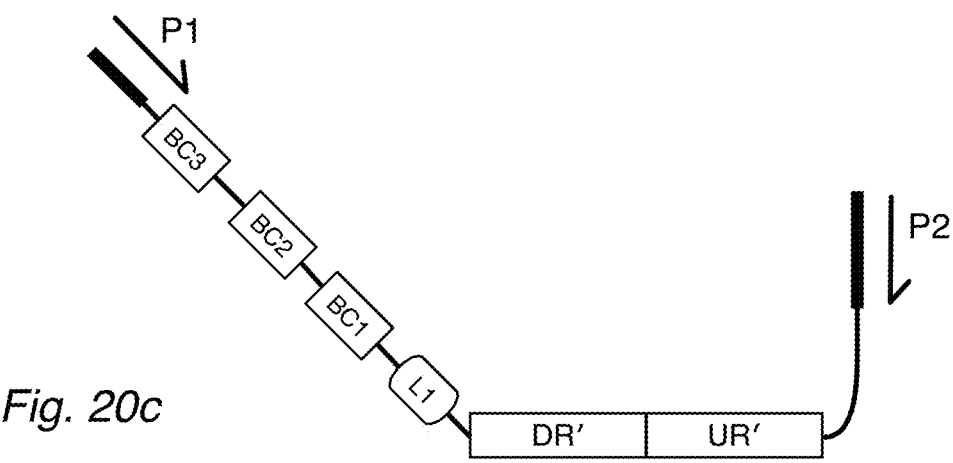

FIG. 20a depicts a barcoding scheme with downstream detector DD and an upstream detector UD, where the UD has a partial P2' amplification sequence. Also provided is a second upstream detector UD2, which has a P2 amplification region and a UR2' region that is capable of hybridizing to a UR2 sequence on the sample. FIG. 20b illustrates the serial addition of barcode sequences as disclosed herein. When the partial P2' sequence of the UD is hybridized to the complete P2 sequence of the UD2, the UD can be extended (using the P2 as a template strand) to obtain a complete P2' sequence suitable for amplification with a P2 primer, as shown in FIG. 20c.

Figure 21A:
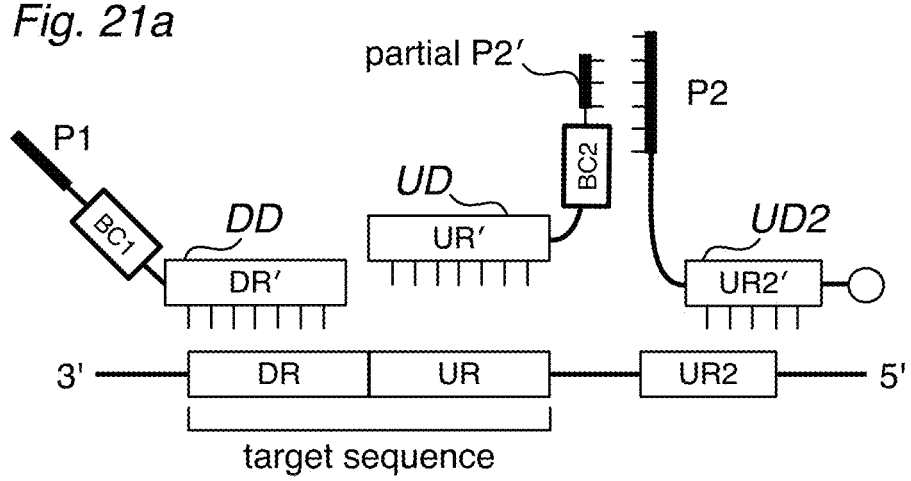
Figure 21B:
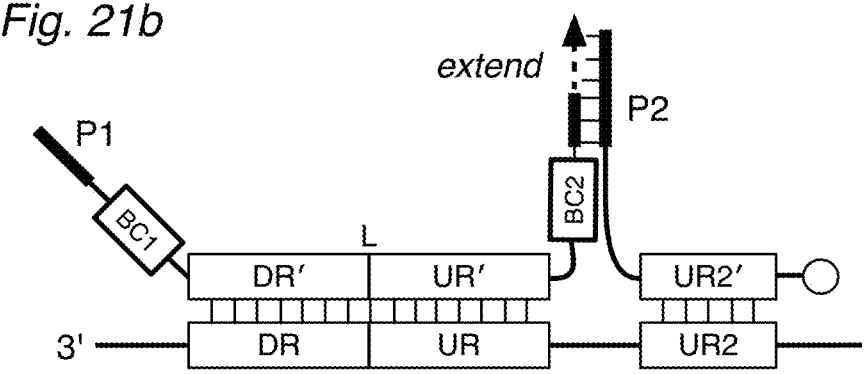
Figure 21C:
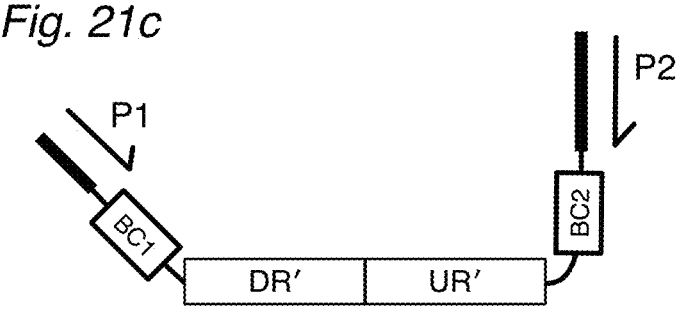

FIGS. 21a and 21b depict a barcoding scheme similar to the scheme in FIG. 20a, where the DD and UD are labeled with barcode sequences BC1 and BC2 respectively. The result is a barcoded ligation product in FIG. 21c that confirms specific detection of the target sequence DR-UR.

Figures 22A, 22B:
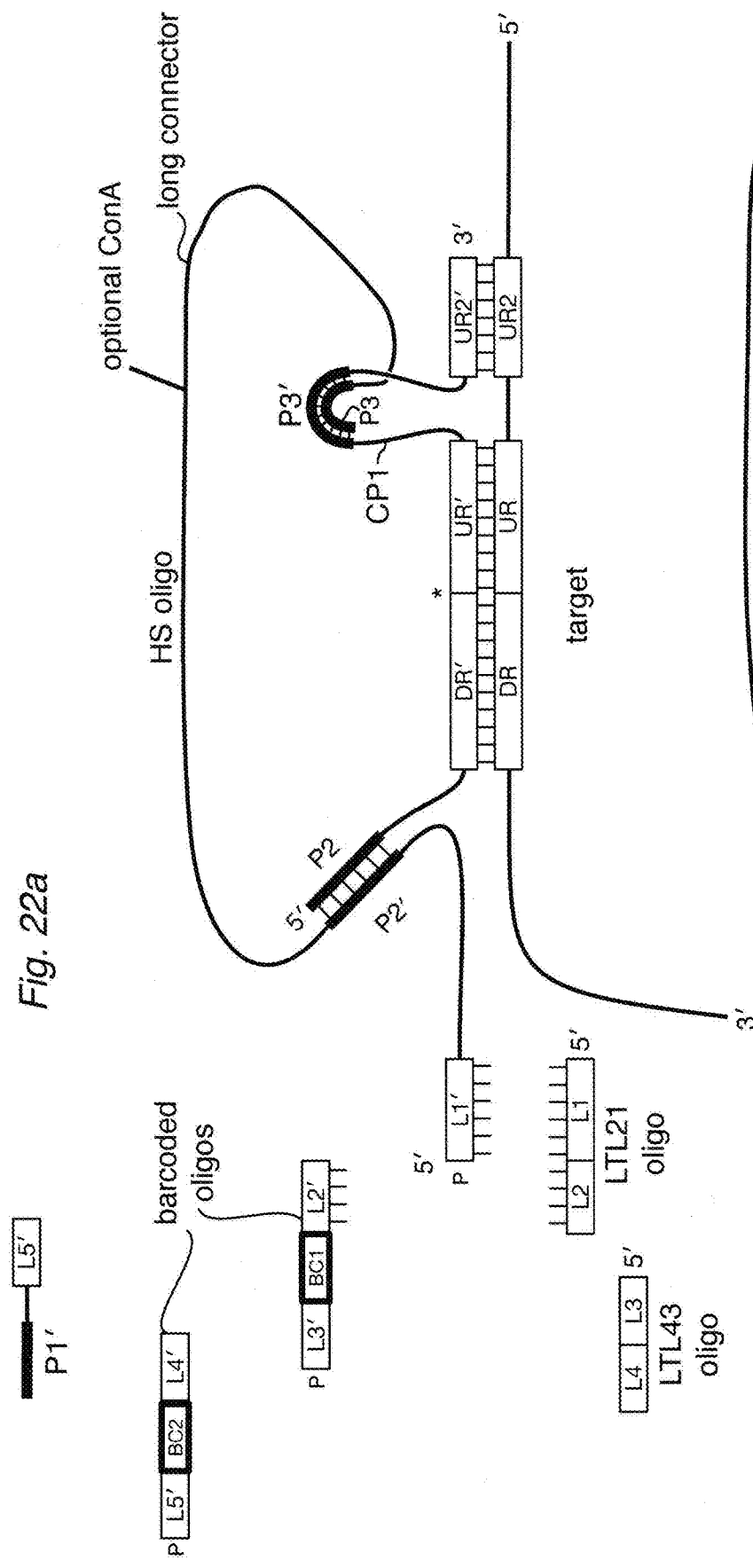

FIG. 22a illustrates an embodiment using a horseshoe oligo (HS) that enables attachment of barcode sequences to generate a complex extension product, shown in FIG. 22b. The extension product confirms detection of the target sequence and is barcoded for individual samples. The extension product may then be amplified with P1 and P2 primers and sequenced.

DETAILED DESCRIPTION OF THE INVENTION

This invention provides methods for detecting target sequences of nucleic acid sequences of interest in a sample, and also provides kits for performing the method.

In a typical ligation assay, the sample is contacted with a pool of detector oligos, where a downstream detector (DD or DDO) and an upstream detector (UD or UDO) are provided for each target sequence. A portion (DR') of the DD is complementary to a region of the target sequence designated as a downstream region (DR). The upstream detector has a portion (UR') complementary to an upstream region (UR) of the target sequence.

The downstream and upstream detectors are contacted with the sample and allowed to hybridize to the corresponding regions of target sequence present in the sample. When the detectors are specifically hybridized to a target sequence, they can be ligated at the junction between adjacent detectors, whether directly or after an optional extension step. Formation of a ligation product thus serves as evidence that the target sequence was present in the sample, and the ligation product can be detected by various methods such as detectable labels, microarrays, qPCR, flow-through counters, and sequencing.

The invention provides assays where one or more nucleases can be provided during steps in the method to selectively degrade unused or excess detectors, or detectors that are not specifically hybridized to target sequences. Accordingly, the detectors and other components of the assay can be configured in a number of embodiments to resist the nucleases while detecting target sequences. The configurations enable sensitive detection of nucleic acids, such as mRNAs and miRNAs, at whole-transcriptome or -miR-Nome multiplexing and at the level of single cells. Moreover, the steps can be performed in a single well or container without the need for transfers, separation, or solid-phase immobilization, and are therefore ideal for microfluidic platforms.

The present invention also provides methods, kits, instruments, and software for profiling nucleic acid sequences of interest in a sample, and also provides kits for performing the method. The method can be performed in minute focal areas of histological samples, such as formalin-fixed, paraffin-embedded tissue specimens (FFPEs).

The detection assays disclosed herein (in different versions, but collectively "TempO-Seq™ assays") enable gene expression to be profiled from areas 1 mm² and smaller focal areas of, for example, of 5 µm thick FFPE sections of normal and cancerous tissue to identify disease biomarkers and mechanistic pathways. The invention can also be performed in situ on slides by an automated slide stainer, followed by antibody staining and/or H&E (hematoxylin and eosin) staining. Then, using a digital imaging platform such as the automated CellSensus™ digital imaging platform of the invention, areas as small as 130 µm down to 30 µm in diameter within the FFPE section can be profiled, permitting the gene expression data to be correlated directly to the specific morphology of that focal area. Smaller and irregular areas of FFPE can also be profiled. Any preparation on slides can be profiled, such as cells fixed to a surface, and the number of cells or amount of tissue can be as little as a single cell or portion of a cell, such as a portion of a neuron.

Pathologists can use the instrument and software of the invention to select areas to be profiled for marker expression during the course of their histologic examination of the section. Detection assay products (such as ligated detector oligonucleotides) can be recovered automatically by the instrument from the selected regions of interest. After transferring the products into PCR tubes, any remaining steps in the detection assay can be completed, such as PCR amplification or preparation for sequencing. Analysis of the sequencing data can be carried out automatically by the software to report results. In the present invention, laser capture and destruction of the tissue become unnecessary. The slides processed by the invention can be dried, treated to stabilize or preserve the sample, or otherwise archived, and additional areas can be sampled at a later date.

Replicate areas of matched normal versus cancerous tissue can be sampled, measuring gene biomarkers of clinical utility. Gene expression profiles are presented for scraped areas of normal, high grade PIN (prostatic intraepithelial neoplasia), and cancer epithelium from prostate cancer patients to perform the TempO-Seq' assay on H&E-stained FFPE samples. The single-cell sensitivity of the in situ protocol is demonstrated by comparing profiles of single MCF-7 cells from a processed Cytospin slide to single cells collected by flow cytometry. The reproducibility of the assay is demonstrated for H&E-stained FFPE samples, as well as the specificity of biomarker expression obtained from profiling areas of stroma, normal and cancer epithelium. These data demonstrate that the automated CellSensus™ platform and assays enable complex molecular tests to be carried out by pathologists in their own labs, and render moot the issues of "% cancer" and the amount of patient tissue required for testing. They demonstrate that spatial resolution and specificity result in greater biomarker specificity. The present invention brings extraction-free complex molecular testing of FFPEs into the pathology lab and provides simplicity, focal spatial precision and correlation to morphology to the field of molecular pathology. While the results presented use fixed tissue or cells on a slide, any surface-adherent sample can be tested as long as it survives the wash steps and the intracellular nucleic acid to be measured is accessible to the reagents.

H&E- or antibody-stained FFPEs can be assayed, providing whole-transcriptome or focused panels of data using as little as 1 mm² area of a 5 mm section. Molecular profiling of high grade PIN adjacent to cancer versus cancer is consistent with adjacent high grade PIN being cancer in situ. Slides can be processed though the in situ assay using an automated stainer, and antibody or H&E staining can be performed on the processed slides. Immunohistochemistry (IHC) assessment can be carried out and areas for automated profiling selected using the CellSensus™ digital molecular pathology platform. The sample can be any surface-adherent sample, such as FFPE or cells. The in situ assay has single-cell sensitivity, even for measuring low-expressed genes. The area profiled is marked so that profiling data can be positively correlated to the tissue microenvironment morphology. Accordingly, the spatial resolution results in biomarker specificity.

Accordingly, the present invention provides a method for detecting a nucleic acid sequence from a selected area of a sample in situ, comprising in any order: imaging the sample for the presence or absence of an analyte; selecting an area of the sample less than 2 mm² based on the imaging; detecting a target nucleic acid sequence having a downstream region (DR) and an upstream region (UR). The detection step is performed by contacting at least the selected area of the sample with a downstream detector oligo (DDO) comprising a DR' portion that is complementary to the DR, and an upstream detector oligo (UDO) comprising a UR' portion that is complementary to the UR, ligating the DR' and UR' if both are specifically hybridized to the DR and UR of a target sequence, and collecting the ligation products from the selected area. As a result, the ligation product indicates the presence of the target sequence in the selected area.

The invention also provides a method for detecting a neoplastic state of a cell by performing the method of the invention where a first cancer marker sequence is detected in the cell. The invention also provides a method for generating a gene expression profile for the selected area, for a plurality of target sequences. A disease state can be diagnosed by performing the method, wherein the target sequence is detected in the area of a morphological feature. The invention also provides kits of detector oligos and stains. The invention further provides an instrument having an imaging component, a component for collecting ligation products from the selected area, and a component for transferring the products to an external container.

Ligation Assays, Generally

Figure 1:
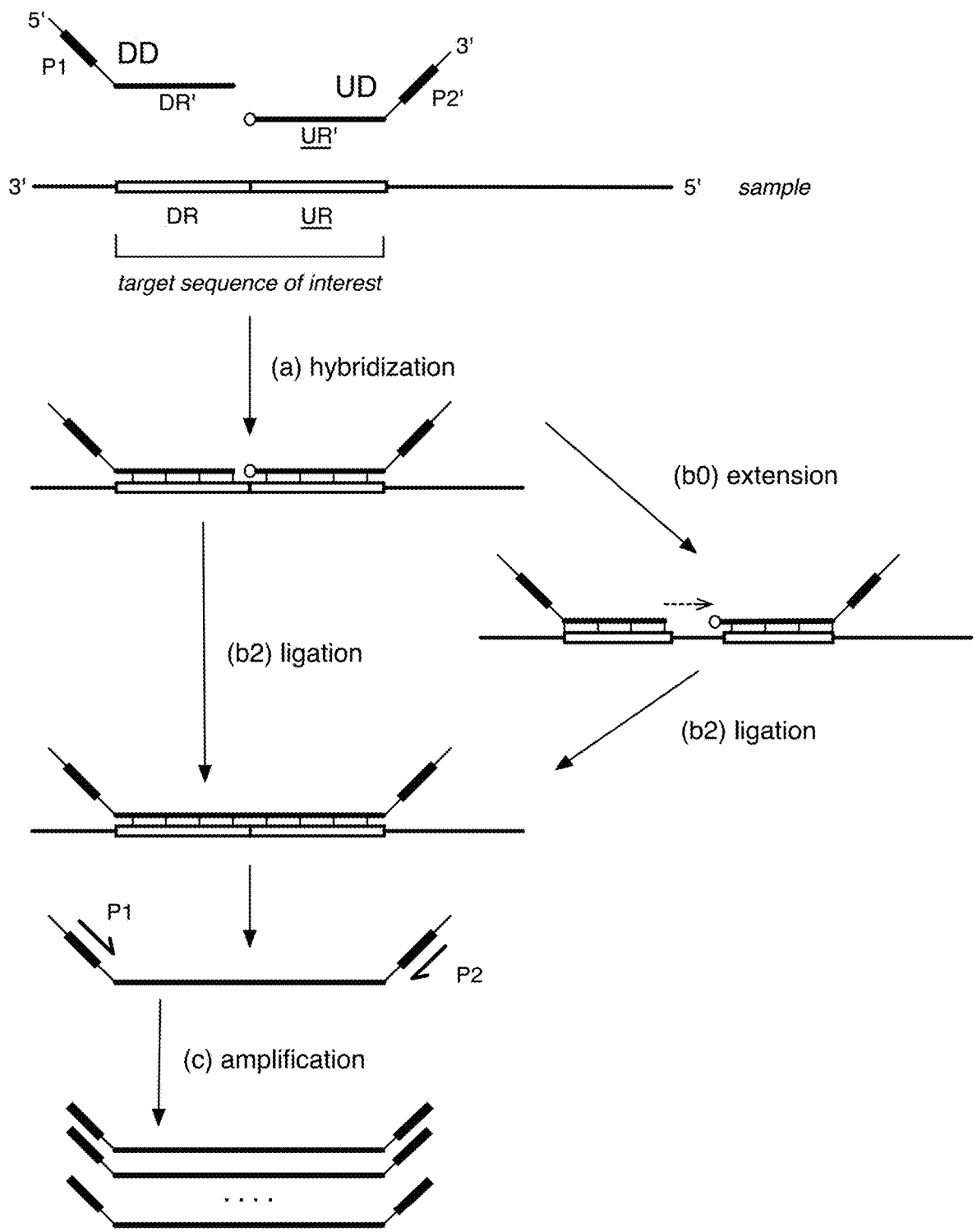
FIG. 1 illustrates a representative ligation assay for detecting target nucleic acid sequences. Briefly, downstream detector (DD or DDO) and upstream detector (UD or UDO) probe oligonucleotides are allowed to (a) hybridize to a target sequence, having DR and UR regions, in a sample. For convenience of identification, upstream regions are often underlined herein. While hybridized to the DR and UR of the target sequence, the DD is (b2) ligated selectively to the UR. Optionally, the DD is (b0) extended prior to (b2) ligation. The ligation product is optionally (c) amplified via amplification regions P1 and P2' by one or more primers, such as P1 and P2.

A typical ligation assay is illustrated schematically in FIG. 1, which is discussed in more detail in Example 1. A sample that may contain target sequences is contacted with a pool of detector oligonucleotide probes ("probes" or "detectors"). For each target sequence, a pair of detectors is provided: a downstream detector (DD) and an upstream detector (UD). A downstream detector can have a portion (DR') that is complementary to a region of the target sequence designated as a downstream region (DR). An upstream detector can have a portion (UR') that is complementary to a region of the target sequence designated as the upstream region (UR). Here, the terms "downstream" and "upstream" are used relative to the 5'-to-3' direction of transcription when the target sequence is a portion of an mRNA, and for convenience the regions designated as upstream are often shown underlined.

As shown in FIG. 1, the DR' of the DD and the UR' of the UD for each target sequence are allowed to hybridize to the corresponding DR and UR of the target sequence, if present in the sample. When the DR and UR of a target sequence are adjacent and the DR' and UR' of the pair of detector oligos are specifically hybridized to the target sequence to form a hybridization complex, the adjacent detectors DD and UD can be ligated. Thus, formation of a DD-UD ligation product serves as evidence that the target sequence (DR-UR) was present in the sample. In cases where the DR and UR of a target sequence are separated by at least one nucleotide, the ligation step can be preceded or followed by (b0) extending the DR' using the sample as a template so the extended DR' and UR' become adjacent and can be ligated. The ligation product can then be detected by a variety of means; if desired, the products can be amplified prior to detection. Various detection methods are disclosed herein.

The present invention also provides methods where hybridization complexes can be exposed at one or more steps to at least one nuclease that can degrade single strands of nucleic acid. As discussed in more detail below, the invention provides detectors and other components of the assay that can be configured to selectively resist the nucleases when detecting target sequences. The nucleases can degrade excess or unused detectors, or detectors that are nonspecifically or nonproductively bound to components in the sample that are not of interest. The strategic use of nucleases enables the ligation assay to be performed by adding one reagent after another in a single reaction container, starting with the sample.

Samples

The samples used in the method can be any substance where it is desired to detect whether a target sequence of a nucleic acid of interest is present. Such substances are typically biological in origin, but can be from artificially created or environmental samples. Biological samples can be from living or dead animals, plants, yeast and other microorganisms, prokaryotes, or cell lines thereof. The sample can contain viral nucleic acids, viruses, or viral cultures. Particular examples of animals include human, primates, dog, rat, mouse, zebrafish, fruit flies (such as *Drosophila melanogaster*), various worms (such as *Caenorhabditis elegans*) and any other animals studied in laboratories or as animal models of disease. The samples can be in the form of whole organisms or systems, tissue samples, cell samples, mixtures, sets or pooled sets of cells, individual cells, subcellular organelles or processes, or samples that are cell-free, including but not limited to solids, fluids, exosomes and other particles. Particular examples are cancer cells, induced pluripotent stem cells (iPSCs), primary hepatocytes, and lymphocytes and subpopulations thereof. The method of the invention can be applied to individual or multiple samples, such as 1, 2, 5, 10, 20, 50, 100, 200, 500, 1000, 2000, 5000, 10,000, 20,000, 50,000, 100,000, 200, 000, 500,000, or 1, 2, 5, 10, or 20 million, or more samples.

The samples can be provided in liquid phase, such as cell-free homogenates or liquid media from tissue cultures, or nonadherent or dissociated cells in suspension, tissue fragments or homogenates, or in solid phase, such as when the sample is mounted on a slide or in the form of formalin-fixed paraffin-embedded (FFPE) tissue or cells, as a fixed sample of any type, or when cells are grown on or in a surface, as long as detectors can be put into contact for potential hybridization with the sample nucleic acids. An optional step in the methods of the invention is deparaffinization, especially for FFPE samples.

Nucleic Acids

The nucleic acids of interest to be detected in samples include the genome, transcriptome, and other functional sets of nucleic acids, and subsets and fractions thereof. The nucleic acids of interest can be DNA, such as nuclear or mitochondrial DNA, or cDNA that is reverse transcribed from RNA. The sequence of interest can also be from RNA, such as mRNA, rRNA, tRNA, snRNAs (small nuclear RNAs), siRNAs (e.g., small interfering RNAs, small inhibitory RNAs, and synthetic inhibitory RNAs), antisense RNAs, circular RNAs, or long noncoding RNAs, circular RNA, or modified RNA. The nucleic acid of interest can be a viral nucleic acid, and the virus of interest can have a DNA or RNA genome that can be single- double- or partially double-stranded. Viral strands and mRNA copies of strands can be distinguished as positive-sense, negative-sense, sometimes ambisense. In certain uses, information from plus-strands and minus-strands can be regarded as different alleles or contrasted with a background of host sequences that are normally present in a cell or due to viral infection or replication.

A particular advantage of the invention is lack of 3' bias. Many previous assays can suffer from 3'-bias because they capture RNA via a poly-A tail and require that the 3' end of RNA be intact. These prior methods may be unable to measure exons/splice variants or expressed SNPs, snRNAs, long noncoding RNAs, gene fusions, or even histone genes. Accordingly, the present invention can be applied to nucleic acid samples that are splice variants, fusion genes, expressed single-base variants, and epitranscriptomic variants of RNA.

The nucleic acids can include unnatural or nonnaturally occurring bases, or modified bases, such as by methylation, and the assay is designed to detect such modifications.

The nucleic acid of interest can be a microRNA (miRNA) at any stage of processing, such as a primary microRNA (pri-miRNA), precursor microRNA (pre-miRNA), a hairpin-forming microRNA variant (miRNA*), or a mature miRNA. Detection of microRNAs is discussed in Example 3a.

Relatively short nucleic acids of interest, such as mature miRNAs, can be lengthened to enhance hybridization to the detectors. For example, many microRNAs are phosphorylated at one end, and can be lengthened by chemical or enzymatic ligation with a supplementary oligo. The supplemental oligo can be single-stranded, double-stranded, or partially double-stranded, depending on the ligation method to be used. If desired, the supplemental oligo can be unique to each target sequence, or can be generic to some or all of the target sequences being ligated. The detectors can then be designed with extended DR' and/or UR' regions that include a portion that hybridizes to the supplemental sequence. A target sequence can also be supplemented by adding nucleotides, such as by polyadenylation, where the extended detectors include at least a portion to hybridize to the supplemental polyA tail. Detection of a family of mature miRNA sequences using extended detectors is discussed in Example 3b and illustrated in FIG. 2*j*.

The amount of nucleic acid in the sample will vary on the type of sample, the complexity, and relative purity of the sample. Because of the sensitivity of the assay, the sample can be taken from a small number of cells, for example from fewer than 100,000, 10,000, 1000, 100, 50, 20, 10, 5, or even from a single cell or a subcellular portion of a cell. The total amount of nucleic acid in the sample can also be quite small: less than 100, 50, 20, 10, 5, 2, 1 micrograms, 500, 200, 100, 50, 20, 10, 5, 2, 1, 0.5, 0.2, 0.1 nanogram, 50, 20, 10, 5, 2, 1 picogram or less of nucleic acid (see FIG. 6*d*), or less than 10, 1, 0.1, 0.01, 0.001 picograms of nucleic acid, or amount of a lysate containing equivalent amounts of nucleic acid. The copy number of a particular target sequence can be less than 100,000, 10,000, 1000, 100, 50, 20, 10, 5, or even a single copy that is present in the sample, particularly when coupled with representative amplification of the ligation product for detection. The amount of input nucleic acid will also vary, of course, depending on the complexity of the sample and the number of target sequences to be detected.

Cross-Linking

It can be useful to retain or reduce the loss of meaningful nucleic acids (such as target, detectors, ligation products, amplicons, their complements, and barcoded versions thereof) at any step of the invention. A crosslinking step can be useful to promote retention of target sequences to cell components or surrounding tissue, particularly when the sample is to undergo one or more wash steps. For example, detectors can be crosslinked to neighboring molecules, such as the target, without making them inaccessible to measurement or interfering with the assay. Thus, the invention provides methods that include a step of crosslinking a molecule in the assay configuration.

These crosslinking methods include 3'-disulfide-modified detectors, to be reduced to a reactive thiol after hybridization using either dithiothreitol or tris(2-carboxyethyl)phosphine (TCEP) as a reducing agent. The detectors can be cross-linked to neighboring protein amines using a heterobifunctional crosslinking agent such as succinimidyl 4-(N-maleimidomethyl) cyclohexane-1-carboxylate (SMCC) which converts protein amines to thiol-reactive maleimides.

Alternatively, the anchor region or a noncomplementary sequence can be modified with a functional group that can be crosslinked to bases in the RNA target sequence. The modification involves nucleoside analog 3-cyanovinyl-carbazole ($^{CNV}K$), which can base-pair to cytosine in the RNA. When photoactivated at 366 nm, the $^{CNV}K$ crosslinks the DDO to the base-paired cytosine RNA residue. If desired, the crosslink can be photo-reversed at 312 nm to release the ligated detectors.

Nucleic acids such as RNA can be cross-linked to cells using the intramolecular epoxide crosslinking SHIELD reagent (LifeCanvas Products, Cambridge, Mass.) with paraformaldehyde. Fixation using SHIELD is compared to formaldehyde, or with formaldehyde followed by SHIELD. The reagent 1-ethyl-3-(3-dimethylaminopropyl)carbodiimide (EDC) can also be used, as well as SHIELD in combination with EDC.

Nucleic acids can also be cross-linked to cell molecules using RtcB ligase and a thiol-derivatized 5'-hydroxyl oligo. RtcB ligates 3'-phosphorylated RNA molecules to oligos with a 5'-hydroxyl. The 5'-hydroxyl-thio-oligos are provided and RtcB catalyzes ligation of fragmented ends of RNA; the thiol group forms a crosslink with amines. If disulfides are used, the thiol can be reduced, for example using dithiothreitol. SMCC, discussed above, can also be used to convert amines to maleimide, which is highly reactive with thiols, and used for forming thiol/amine crosslinks.

Selection of Target Sequences for Design of Detectors

The target sequences can be selected from any combination of sequences or subsequences in the genome or transcriptome of a species or an environment, or modified nucleic acids or nucleic acid mimics to which the detector oligos can bind or hybridize. The set can be specific for a sample type, such as a cell or tissue type. For some sample types, the number of target sequences can range in any combination of upper and lower limits of 1, 2, 5, 10, 20, 50, 100, 200, 500, 1000, 2000, 5000, 10,000, 20,000, 23,000, 30,000, 38,000, 40,000, 50,000, or more. The number of target sequences can also be expressed as a percentage of the total number of a defined set of sequences, such as the RNAs in the human transcriptome or genes in the human genome, ranging in any combination of upper and lower limits of 0.1%, 0.2%, 0.5%, 1%, 2%, 5%, 10%, 20%, 25%, 30%, 35%, 40%, 45%, 50%, 65%, 60%, 70%, 75%, 80%, 85%, 90%, 95%, and 100%. Where large sets of detector oligos are used, it can be useful to check the full sequence of each oligo for potential cross-hybridization to other oligos in the set, where, for example, one oligo may inadvertently serve as an template to other detectors. While such non-specific artifacts can be identified by sequence, and are typically discarded from detection results, they may represent noninformative hybridization events that compete for reaction resources.

The target sequence of interest can be a cancer-associated marker, such as any of genes listed in Tables 1, 2, and 3.

Detector Oligonucleotides

Based on the particular target sequences, the invention provides pools of detector oligos where a target sequence has a pair of upstream and downstream detectors (UDOs and DDOs) that correspond to DR and UR, which are typically subsequences of the entire nucleic acid sequence of interest. Detector oligos can be designed to hybridize to the target sequence so a single-stranded sequence portion of the target sequence remains between the detectors, which can then be filled in, such as by reverse transcriptase or polymerase, thereby extending a detector to bring it effectively together with the other detector so they can be ligated.

Detectors can be provided to detect targets that contain mutations including individual single-nucleotide polymorphisms (SNPs), gene fusions, and exon-splicing variants, or modifications such as pseudouridylation and methylation. For example, DNA samples of interest can have bases that are methylated, such as $N^6$-methyladenine ($m^6A$). DNA from mammals and other species can have one or more 5-methylcytosine ($m^5C$) modified bases, often appearing in GC, CHH and CpG dinucleotides, which sometimes form CpG-rich islands. For RNA samples, modifications to be detected by the invention include methylated ribonucleotides having $m^6A$ (often playing a role in mRNA regulation), $m^5C$, and $N^1$-methyladenosine (m'A), which can be dynamically modified in mRNAs and is sometimes correlated with protein translation.

Detectors can contain blocking groups, modified linkages between bases, unnatural or nonnaturally occurring bases or other unnatural or nonnaturally occurring components. An individual target sequence can have more than one set of DRs and URs, which can be selected by the user to optimize the performance of the assay. Multiple sets of DRs and URs can provide multiple measurements of the same target sequence or of different portions of the target sequence, such as different exons or exon junctions, or provide measurement of a portion of sequence that is not mutated versus a portion of sequence that may harbor a mutation.

The detector oligos themselves can be DNA, RNA, or a mixture or hybrid of both. If desired, they can have a modified nucleotide such as dideoxy nucleotides, deoxyUridine (dU), 5-methylCytosine (5mC), 5-hydroxymethylCytosine (5hmC), 5-formylCytosine (5fC), 5-carboxylCytosine (5caC), and Inosine. Yet other modifications to detector oligos include modified bases such as 2,6-diaminopurine, 2-aminopurine, 2-fluro bases, 5-bromoUracil, or 5-nitroindole. Other detector oligos can have a modified sugar-phosphate backbone at one or more positions. Such modifications include a 3'-3' or 5'-5' linkage inversion, a locked nucleic acid (LNA), or a peptide nucleic acid (PNA) backbone. LNAs can be useful for their stronger hybridization properties to complementary bases, enhancing the selectivity or the overall binding affinity for the detector oligo as a whole. The modified bases or bonds can also be used at positions 1, 2, or 3 away from the point of ligation.

As shown schematically in FIG. 1, a downstream detector (DD or DDO) has a complementary downstream region (DR'), which can be at least 4, 6, 8, 10, 12, 14, 16, 18, 20, 22, 24, 26, 28, 30, 35, 40, 45, or 50 nucleotides in length. Similarly, an upstream detector (UD or UDO) has a complementary upstream region (UR'), which can be at least 4, 6, 8, 10, 12, 14, 16, 18, 20, 22, 24, 26, 28, 30, 35, 40, 45, or 50 nucleotides in length. In a given pair of DD and UD for a target sequence, the DR' and UR' need not be exactly the same length, but will typically be similar so they can hybridize to the target under similar conditions and stringency.

As discussed in more detail below, the detectors, LTLs, and barcoded oligos can be optimized for ligation, such as by providing a 5'-phosphate, although this is not necessary, depending on the selection of ligase or other ligation methods. Ribonucleotides can also be substituted at the ligatable ends of the DD and UD to increase the specificity and efficiency of ligation, as when an RNA ligase is used.

Anchored Detectors

In one configuration of the TempO-Seq™ assay, the upstream detector has a second region (UR2') that is complementary to a second region of the target sequence (UR2), as illustrated in FIG. 2a. Because the tail of the UD can hybridize to a separate portion of the target, this configuration can be described as an "anchored" detector, as in FIG. 2b. The anchor at the 3' end of the UD hybridizes with the target to form a double-strand and is thus configured to resist digestion to nucleases that degrade single strands, such as 3' exonucleases like exo I.

As a separate target-binding region, the anchor UR2' can be used to provide additional discrimination between similar sequences, such as isoforms of a family of genes where sequence differences between isoforms are found beyond the range of the DR and UR target sequence.

The UR2' can be at least 4, 6, 8, 10, 12, 14, 16, 18, 20, 22, 24, 26, 28, 30, 35, 40, 45, or 50 nucleotides in length. The UR2' can be separated from the UR' by a noncomplementary region (CP1), which can be at least 8, 10, 12, 14, 16, 18, 20, 22, 24, 26, 28, 30, 35, 40, 45, 50, 60, 70, 80, 90, or 100 nucleotides in length. In general, the UR2' will be upstream relative to the UR'. If an amplification region (such as P2') is present, it can be upstream of the UR', such as within the CP1 or part of UR2' to allow amplification of the UR' portion as shown in FIG. 2c to generate the amplification products (AP) in FIG. 2d.

In a mirror-image configuration, it is the downstream detector that has the anchor region (DR2') complementary to a second region of the target sequence. The DR2' anchor hybridizes to a DR2 on the target so that the configuration resists the action of 5' ss-exonucleases. The UR2' of the DD will generally be downstream relative to the UR'. If an amplification region (such as P1) is present, it can be downstream of the DR' to allow amplification of the DR' after ligation. Anchored DDs and UDs can be used separately or in combination to resist a cocktail of nucleases.

Because the separate anchor region of the detector can affect the hybridization characteristics of the detector via monomolecular kinetics, the compositions and relative lengths of the DR2', CP1(s), DR', UR' and UR2' can be tuned to optimize target selectivity between the detector pair and among the pairs of the detector pool.

Detectors that are not used in the ligation reaction can be degraded as shown in FIG. 2e. Moreover, incompletely bound detectors, such as those in FIG. 2f, can also be degraded, for example when the UR' of a UD binds to the UR of a target, but the UR2' does not bind, whether because the UR' is bound to a non-target sequence or to a target that was related to the intended target UR but lacked a UR2. Similarly, an anchored DD that binds a DR2 but not the DR of a target will be susceptible to a 3' ss-exonuclease (or will not generate a valid ligation product with a corresponding UD). Other detectors will fail to be amplified, for example detectors in excess of target sequence in the sample or detectors that are bound nonspecifically to nontarget sequences. The use of anchored detectors can therefore increase the specificity of the ligation assay for target sequences while allowing nucleases to degrade excess or unused detectors.

Blocked Detectors

Another configuration has detectors, LTLs, bridge oligos, horseshoe oligos, barcoded oligos, or other assay oligos that are nuclease-resistant by having a nuclease-blocking group at or adjacent to one end. FIG. 2h shows a DD, having a 5'-blocking group, that can be used in combination with a 5' exonuclease. Also shown is a UD having a 3'-blocking group for use with a 3' exonuclease. Preferably when a 5' or 3' exonuclease is used where there are multiple targets and pairs of detectors, all of the downstream or upstream detectors have a 5' or 3' block, respectively.

Useful configurations for resisting nucleases include termination with an inverted nucleotide such as deoxythymidine (idT), a dideoxynucleotide such as dideoxythymidine (ddT or iddT), or 2'/3'-O-acetyation of the terminal nucleotide. Depending on the substrate preferences of the nuclease selected, one or more of the other modified nucleotides described earlier can be used as a blocking group. Alternatively, one or more of the terminal nucleotides are attached to the rest of the oligo via one or more phosphorothioate bonds instead of naturally occurring phosphodiester bonds. Other modifications that may resist a nuclease include the LNA or PNA backbones discussed earlier. In some configurations, a hairpin loop or other secondary structure on the detector can serve as the nuclease-blocking group for a detector. One end of the hairpin can have a blocking group. In other configurations, prior to hybridization, a protein or other component can be bound the 5' end of a DD or the 3' end of a UD, such as a sequence-specific single-strand-binding protein like a far upstream element (FUSE) binding protein (FUBP) via a ssFUSE sequence incorporated into a detector. If the 5' end of a DD or the 3' end of a UD detector is configured to be immobilized, whether permanently or reversibly, to a solid phase, the solid phase itself can serve as a block against nuclease activity on the detector. It can be useful to combine any of the preceding features in a single detector or both detectors to resist the action of the nuclease selected and to provide other advantages, such as stability and hybridization properties.

Protectors

Yet another configuration provides one or more oligos that protect the assay oligos, such as detectors by hybridizing to the DD or UD at a region that will not interfere with hybridization of the DR' or UR' regions complementary to the target sequence. For example, in FIG. 2i, a DR2 protector oligo is provided to hybridize to a DR2' region at the 5' end of the DD, forming a double-stranded configuration (indicated by a brace) that is resistant to 5' exonucleases. If a 3' exonuclease is to be used, then a UR2 protector can be provided to form a double-strand at the 3' end of the UD. The protector oligos can themselves be protected from exonuclease activity by a blocking group or bond as described above. For example, a 3'-blocked UR2 protector is shown in FIG. 2i, and a 5'-blocked DR2 protector is shown in FIG. 2j. If a cocktail of 5' and 3' exonucleases is to be used, then both DR2 and UR2 protectors can be provided, optionally with 5'- or 3'-blocking groups, respectively.

Detector Labels

Where the ligation assay proceeds directly to a detection step, either or both detectors can be designed to be labeled appropriately for detection. For example, the detector can be conjugated to any number of molecular or physical entities, labeled with a crosslinker, activatable crosslinker, activatable cleavage group or enzymatically cleavable group, optical, color or fluorescent dye, latex or other beads, quantum dots, or nanodots, or nanoparticles. Any of these entities can also be further modified or conjugated to other entities. For example, one component of the assay can be a donor chromophore and another component can be an acceptor chromophore of a fluorescence resonance energy transfer (FRET) detection system. Another assay component can have a quencher reversibly attached to a fluorophore that can be separated under conditions that indicate specific detection of a sequence. Multiple fluorophores can be used in an assay to indicate the presence of different target sequences, different alleles, different organisms, or different samples. Similarly, single fluorophores can be used to indicate selected sets of target sequences, alleles, organisms or samples for a simplified, combined readout.

The label can also take the form of an additional nucleotide sequence that serves to enable detection and identification, such as a barcode sequence. The DD or UD, or both, can contain a barcode sequence. For example, a useful barcode sequence can uniquely identify the specific gene or target sequence, or a group of select genes or target sequences within the sample that are being measured. Such sequences can be positioned between the UR' and P2' sequence, and/or between the DR' and P1 sequence, so they are amplified when using flanking primers. This sequence can also be a random sequence, useful for identifying the number of copies of the target gene in the sample, independent of the particular efficiency of any amplification step. More commonly, barcodes are understood to be predefined unique sequences that do not or are unlikely to occur in nature or in the sample of interest, in either complement or orientation. Barcodes can incorporate redundant and/or error-correction features.

Cleavable Detectors

It can be desirable for a detector oligo or other assay oligos to contain one or other modifications that can be selectively cleaved by treatment after the ligation or optional amplification step. For example, a detector oligo can have a dU located so that it will not interfere with hybridization or ligation steps. After ligation, however, products incorporating the dU oligo can then be cleaved by dU-specific enzymes, such as uracil-DNA glycosylase followed by endonuclease VIII. Another selectively cleavable site can be a restriction enzyme cleavage site that is not present in the target sequences to be detected. Yet another cleavage site is a photocleavable site. It may also be useful to incorporate a moiety that can be crosslinked before or after ligation, such as a photoactivatable or chemically activatable crosslinker.

Multiple Detectors for a Gene

Multiple detector oligo (DO) sets targeting different sequences within a gene can be designed and synthesized for use to detect that gene. Each DO set hybridizes to its targeted sequence independently of the hybridization of other DO sets to each of their respective targeted sequences. Thus, the statistical reliability, statistical power, of measurement of the gene itself can be increased by use of multiple DO set targeting that gene. Measurement CVs can be reduced. Furthermore, if secondary structure, protein binding, or other factor modulates the hybridization of one DO set, and thus affects resulting measure of gene abundance by that DO set, then the counts from other DOs unaffected by such factors can be used to provide more accurate measure of gene abundance. Outlier analysis can be used to identify such deviations of DO set measurements. In the case that the expression of a gene is low abundant, or that the amount of sample is small, such as from a single cell, and thus the number of gene molecules is low, hybridization of a specific DO set to that low amount of gene may not be sufficient to provide an amplifiable ligated product every time across repeat samples, and hence, not produce sequencing counts from some samples. The use of additional DO sets targeting other sequences within the same gene increases the probability that some of those DO sets will produce counts if the gene is actually expressed, and thus use of multiple DO sets can be used to increase the sensitivity of measurement of low expressed, or low numbers of gene molecules in a sample. The no sample background counts can be used to validate that DO counts result from the presence of the gene even though not all DO sets produce counts. The concurrence of more than one DO set reporting the presence of the gene can be used as a measure to validate that the DO counts result from the presence of the gene even though not all DO sets produce counts. Because the DO sets have a defined sequence, each DO set measurement represents independent measurements of defined target sequences, permitting statistical methods to be applied to determine that a gene is expressed or present in the sample or not.

Detecting Modified Nucleotides

In a particular embodiment, multiple detectors can be used to detect the presence or absence of modifications to a nucleic acid. For example, a first pair of detectors can be directed to a first target sequence of a full-length nucleic acid of interest, such as an mRNA, where the first target sequence is suspected of having a modification, such as methylation, at a particular position for interrogation. The first pair of detectors may yield one detection result (e.g. generation of an analytical ligation product or amplicon) when the modification is present at the position, and yield a different detection result (e.g. no analytical product) when the modification is absent from the same position. Detectors, which are directed to one or more different target sequences or positions of the full-length nucleic acid, can be used as a positive control for the presence of the full-length nucleic acid.

Hybridization

Returning to the steps of the assay, the detectors are provided so that they contact the sample to allow the detectors to hybridize specifically to the target nucleic acids. Hybridization conditions can be selected by the skilled artisan to allow and optimize for hybridization between the polynucleotides with the desired degree of specificity or mismatches, and such conditions will vary with the lengths and compositions of sequences present in the hybridization reaction, the nature of any modifications, as well as conditions such as the concentrations of the polynucleotides and ionic strength. Particular hybridization temperatures include 30°, 32.5°, 35°, 37.5°, 40°, 42.5°, 45°, 47.5°, 50°, 52.5°, 55°, 57.5°, 60°, 62.5°, 65°, 67.5°, 70°, 72.5°, 75°, 77.5°, 80°, 82.5°, 85°, 87.5°, and/or 90°. Particular hybridization temperatures can be achieved by ramping the temperature up or down at various rates and profiles, such as timed temperature plateaus, one or more incremental increases or decreases of 5 C°, 10 C°, or 15 C°, and repeated cycling between two or more temperatures. Ions such as $Li^+$, $Na^+$, $K^+$, $Ca^{2+}$, $Mg^{2+}$ and/or $Mn^{2+}$ can also be present from 0, 1, 2, 5, 10, 20, 50, 100, 200, and 500 mM, and such ions can affect the selection of the other hybridization conditions. Hybridization is also affected by steric crowding components such as branched polysaccharides, glycerol, and polyethylene glycol. Further additives can be present in the hybridization (and subsequent) reactions, such as DMSO, non-ionic detergents, betaine, ethylene glycol, 1,2-propanediol, formamide, tetramethyl ammonium chloride (TMAC), and/or proteins such as bovine serum albumin (BSA), according to the desired specificity.

Optionally, the conditions for hybridization can be adjusted or fine-tuned to permit other steps to be performed in the same environment. For example, the same buffers used for hybridization can be used for lysing cells in a sample, promoting hybridization of certain cell types, facilitating removal or permeation of cell walls, cell membranes, or subcellular fractions, as desired. Depending on the ligation method used in the assay, hybridization conditions can be selected to be compatible with conditions for ligation as is, or with the addition of one or more components and preferably without requiring a change of the reaction container when transitioning from hybridization to ligation steps.

Ligation

The ligation reaction can occur by chemical ligation or by using a ligase enzyme or a ligation-facilitating co-factor. A variety of nick-repairing ligases are commercially available to catalyze the formation of a phosphodiester bond between adjacent single-stranded polynucleotides when hybridized to another single-stranded template, such as to join DNA to RNA when hybridized to template. An example is bacteriophage T4 DNA ligase, which is generally understood to use ATP as a co-factor. The ATP can be supplied during the ligase reaction. In other reactions, the ligase can be pre-adenylated. In yet other reactions, the UD must be pre-adenylated at the 5' end, as with a 5' App DNA/RNA ligase. The UD in a typical reaction will have a 5'-phosphate to facilitate ligation to the DD, although this is not necessary, depending on the selection of ligase and ligation conditions. (Where a 5'-phosphate on the DD is required for efficient ligation, using a comparable oligonucleotide without 5'-phosphorylation can be used to inhibit or reduce undesired ligation.) Preferred ligation conditions include 10, 25, 50, 100 mM Tris-HCl (pH 7.5, 8.0, or 8.5); at least 10 mM, 5 mM, 2 mM, 1 mM $MgCl_2$; at least or at most 2 mM, 1 mM, 0.7 mM, 0.5 mM, 0.2 mM, 0.1 mM, 0.05 mM, 0.02 mM, 0.01 mM, 0.005 mM, 0.002 mM, or 0.001 mM ATP; or at least 10 mM, 7 mM, 5 mM, 2 mM, 1 mM, 0.5 mM DTT or other antioxidant. T3 DNA ligase can also be used, which can ligate a broader range of substrates and has a wider tolerance for salt concentration. As with other steps, the temperature can be selected according to the characteristics of the reaction components and conditions such as ionic strength.

As discussed above, the ligation step can be preceded or followed by an optional extension step, as in FIG. 1, step (b0). Enzymes useful for extension include polymerases that can add nucleotides to a primer nucleic acid strand in a template-dependent fashion. A useful polymerase is the Klenow fragment of E. coli DNA polymerase I, although skilled artisans can select polymerases and extension reaction conditions for a particular configuration. Other uses for extension steps are illustrated in FIGS. 20b and 21b, where a polymerase can be used to extend a partial P2' sequence to complete a P2' amplification sequence for later use with a primer. The ligation step can also be preceded by an optional cleavage step, such as by a nuclease, to remove any overhangs. In other cases, a portion of the DD can overlap with the UR sequence to which the UD hybridizes, so that after hybridization of the UD and the DD, there is an overhang sequence of 1, 2, 3, or more bases. A useful enzyme for removing an overhang is a Flap endonuclease, such as Fen-1, which cleavage leaves a ligatable 5'-phosphate.

Amplification

If desired, the ligation product can be amplified (for example by PCR or qPCR) to facilitate detection. Amplification methods and instruments are commercially available, including PCR plate and droplet formats, and the amplification enzymes (such as Taq and its commercial variants) and reaction conditions can be selected and tailored to the particular platform. Optionally, the polymerase selected for amplification can have strand-displacing activity.

As illustrated in FIG. 1, the detectors can have additional sequences ("tails") including primer hybridization sequences (e.g. P1, P2') or complements thereof, that serve as amplification sequences, so that after ligation, the ligation product can be amplified with a pair of amplification primers (P1, P2). An exemplary downstream amplification sequence (P1) is (SEQ ID NO: 1)
5'-CAAGCAGAAGACGGCATACGAG-3', which can be used with a primer having the same sequence (P1). An exemplary upstream amplification sequence (P2') is (SEQ ID NO: 2)
5'-ATCTCGGTGGTCGCCGTATCATT-3', which can be used with primer P2 (shown in 3'-to-5' orientation):

(SEQ ID NO: 3)
3'-TAGAGCCACCAGCGGCATAGTAA-5'.

Amplification can also be linear, or achieved by any number of methods other than PCR. If desired, the amplification primer can incorporate a barcode sequence, for example a barcode sequence that uniquely identifies the sample in a multi-sample experiment, and optionally has redundant and/or error-correction features. In some experiments, for example, different sample barcodes can be used for at least 16, 32, 96, 384, 1536, or more, or more generally $2^n$ or $4^n$ different samples that are prepared with different barcodes separately for some steps, such as hybridization, ligation, and amplification, and combined for others, such as detection. The barcode sequence can be incorporated into the primer, such as 3' to the amplification sequence, so that the barcode becomes part of the amplified strand. In other instances, the amplification sequence of the primer can be extended by an additional sequence to provide a primer hybridization sequence that can be used for use in subsequent sequencing steps. The barcode may also be interposed between the amplification sequence, and if desired, the extended amplification sequence, and another sequence that can be used for capture, such as capture onto a surface as part of a sequencing process, and/or for yet another primer hybridization sequence that is used for sequencing. In each case the barcode will be amplified with the rest of the detector sequences, for instance forming a single amplified, elongated molecule that contains sequencing primer hybridization sequences, sample barcode, and a gene-specific sequence, which may include a gene-specific barcode or a target molecule-specific barcode as well as sequence or complement to the sequence of the target gene. In the case where the targeted oligo is a cDNA, a gene-specific sequence or a sample-specific sequence can be added as part of the primer used for reverse transcription, and be a part of the sequence targeted by the UD and DD.

In other instances, methods known in the art can be used to amplify the ligated DD and UD sequences, such as by repetitive cycles of (1) ligation, (2) heating to melt off the ligated product, (3) cooling to permit hybridization of DD and UD to the target, (4) ligation, then repeating the heating (2), cooling (3), and ligation (4) steps. These additional amplification steps can be performed before amplification step (c), during which the sample barcodes and other sequences are added to the ligated UD and DD sequence. The target of the UD and DD hybridization may also be amplified by whole transcriptome amplification of RNA or amplification of cDNA. Thus, amplification primers are provided having a barcode sequence or a portion complementary to a barcoded oligo. The primers can also have predetermined sequences to facilitate use with commercial sequencing workflows, as shown in FIG. 16.

The barcode can contain additional nucleotides than numerically necessary for unique correspondence between the physical sequence and the information it embodies. For example, the barcode can contain noninformative or redundant nucleotides, and can contain error-correcting features. The individual nucleotides do not need to be contiguous to provide information. Information from noncontiguous subsequences of a barcode may be combined to convey information to identify a sample, gene, or allele, for example. In one embodiment, barcode sequence can also serve as a sequence that is a target for a hybridization probe. In a particular embodiment, the hybridization probe is a fluorophore-quencher hydrolysis probe. This can provide an alternate and independent readout mechanism for the assay to rapidly distinguish alleles using a range of fluorophores.

TempO-Bar

The invention also provides methods for attaching barcode sequences to the detectors, ligation product, or amplification products at one or more stages of the method. A barcode can be attached to a detector prior to hybridization, during hybridization, prior to ligation, after ligation, or after amplification. The barcodes can be attached directly or indirectly via another molecule, such as a linking oligo. If desired, the same or different barcodes (or the same, overlapping, or exclusive sets of barcodes) can be used for attachment in various stages. The addition can be to the same molecule (serially), to different positions of the same molecule, or to different molecules in parallel. The barcode sequences can appear or be incorporated into an amplification product for detection.

In one embodiment, a detector oligo is labeled by attaching a barcode sequence during the methods of the invention, for example after detectors are ligated. The attachment can be to the 3' end, or to the 5' end of the ligated detectors as illustrated in FIG. 16, part B.

Barcoded Oligos

The barcodes to be attached or incorporated into other molecules of the method can take the form of an oligonucleotide having a sequence of nucleotides with different bases that serve to identify the barcode. The barcoded oligo can have additional nucleotides in the 5' or 3' direction to provide additional functionality. For example, a useful barcoded oligo has a general structure of 5'-L2'-barcode-L1'-3', where L2 and L1 are linker sequences or their complements (series B1, below). The linker sequences can be the same or different, or in any strand orientation. In other embodiments, a barcoded oligo has a general structure of 5'-P1'-barcode-L1'-3' (terminal series B2, below) to provide an amplification primer landing site for subsequent amplification of a serially barcoded construct. The series B2 oligos can be used with or without B1 oligos participating in other steps.

Linker oligos can be provided, such as ligation template linkers (LTLs), which can hybridize or be attached to other oligos. For example, an LTL oligo can have a general structure of two linker L sequences, such as 5'-L5-L2-3', 3'-L3-L4-5' or 3'-L6-L7-5' shown in FIG. 18a. L sequences in an LTL can be unique or the same, or complements or reverse complements of each other, which can be selected depending on the desired order and configuration of attachment. An LTL that serves as a splint to link L2 and L1 sequences can be described as an LTL21 oligo. Sets of ligation template linkers can be provided as illustrated in FIG. 16, where one LTL has the structure 3'-L2-L1-5', where L1 is selected to be a sequence complementary to a P1 amplification sequence (thus LTL12 or LTLP12). Other LTLs can be provided, such as 3'-L4-L3-5' or 3'-L6-L5-5' to serve as splints for ligating barcoded oligos, designated LTL43 and LTL65, respectively.

Any of the barcoded oligos, LTL oligos, bridge oligos, or horseshoe oligos disclosed herein can be single-stranded, double-stranded, contain overhangs or have partially single-stranded regions. Like the detectors disclosed herein, they can have modified bases, nucleotides, and linkages, as well as labels, conjugated groups or molecules. For example, LTLs can incorporate a locked nucleic acid (LNA), or a peptide nucleic acid (PNA) backbone, which can serve to reduce the necessary length of the LTL. The oligos can have groups that block one or more steps of the methods to prevent certain oligos from participating in a step. If desired, they can incorporate cleavage sites, which can be activatable or reversible.

Some oligos can be phosphorylated to promote enzymatic ligation, such as when using one of the ligases discussed herein. Other oligos can be functionalized with reactive groups to allow chemical ligation, particularly click chemistry reactions. An example of such a functionalization is shown in FIG. 17, where a detector has a 5'-iodo group. The 5'-iodo is activated by treatment with azide to form a reactive 5'-azido group. The coupling can then be carried out in the presence of a copper catalyst. Various click chemistries have been described for combinatorial synthesis, but not to assemble barcodes, especially for samples and reactions in situ.

Attachment of Barcoded Oligos

Barcoded oligos can be attached to assay components in various combinations and stages of the method to provide useful identification. For example, a barcode can be attached to a detector during hybridization to identify a particular allele. A barcode can be attached to a ligation product at one stage to signal that ligation has occurred. These barcodes can be incorporated into a product that is amplified and sequenced by itself or with other sequences to characterize the interactions of the molecules in the method of the invention.

In one embodiment, the barcodes are used to identify individual samples, groups of multiple samples, or subpopulations of a population of samples, or various combinations thereof. For example, a population of samples can be labeled with a first barcode, or multiple populations can each be labeled with a unique barcode forming a set of barcodes. In further embodiments, a different population of samples can be labeled with a second barcode, or with a second set of unique barcodes. Additional barcodes can be added in additional steps for different populations of samples.

Between barcoding steps, the populations of samples may be pooled, mixed, split, aliquoted, or divided in any combination. For example, a first set of samples can be barcoded with a first set of barcodes, and a second set of samples can be barcoded with a second set of barcodes. Where the two rounds of barcoding are separated by time, wash steps, or physical isolation, the first set of barcodes can be reused for the second round of barcoding. In other embodiments, different sets of barcodes can be used to informatically identify different rounds of barcoding and to detect contamination between different populations of samples, or incomplete washing between rounds.

Where the number of samples is large, it can be useful to use sets of large numbers of uniquely barcoded oligos. For example, if a set of 96 barcodes is added to 96 subpopulations of samples, and the barcoded samples are remixed and independently split in n successive rounds (orthogonally), the number of identifiable sets of samples is up to 96 g. Thus, in principle four rounds of barcoding can identify $96^4$ or nearly 85 million sets of samples. When the samples are single cells, this enables unique identification of individual cells synergistically coupled with specific detection of target molecules. The number of barcodes used can also vary according to the expected expression level of a particular gene. For example, a quantitative dynamic range of 1, 2, 5, 10, 20, 50, 100, 200, 500, or 1000 unique molecular barcodes (UMIs) can be used to detect low expressed genes, and up to 10,000, 20,000, 50,000, 100,000, 200,000, or 500,000 or more UMIs for highly expressed genes.

Serial Addition of Barcodes

In a series of embodiments, barcodes are attached to detectors that have been specifically hybridized to target sequences and ligated in a number of samples, where different samples receive different barcodes. To reuse the same set of barcodes, or a different set of barcodes, the samples are thoroughly mixed and split into separate pools of samples, which can each receive the barcodes in a separate round. By repeating these steps, the individual samples can be barcoded serially and combinatorially. Iteration of these steps enables unique barcoding of a large starting numbers of individual samples.

In one embodiment, illustrated in FIG. 16, part B, an LTL21 is provided that can hybridize to a P1 portion of the DDO. A first set of B1 barcoded oligos is provided, exemplified by the B1a oligo, 5'-L3-B1a-L2-3', where B1a represents a particular B1 barcode. The first set is then hybridized to LTL21 and ligated. Several iterations of mixing and dividing are performed, adding more B1 oligos, such as B1v and B1h. If desired, a terminal B2 oligo can be attached (exemplified as 5'-P3-B2k-L8-3'), which provides a primer sequence for later amplification. A mirror-image configuration of this embodiment can also be performed, where an LTL hybridizes initially to the UDO and the method adds barcodes in the 3' direction.

FIG. 17 illustrates a variation of this embodiment where barcoded oligos are chemically attached via click chemistry reactions, which does not require LTL oligos, and is further discussed in Example 13.

Dual Sided Barcoding

In an embodiment exemplified in FIG. 18a, a first set of barcoded oligos (shown as L2'-BC1-L1') is attached to one end of a ligation product (having a 5'-L1 linker sequence) for different sets of samples. After mixing and redividing into orthogonal subpopulations, a second set of barcodes is attached to the other end of the ligation product for each pool of samples. This is illustrated by adding L4'-BC2-L6' to the 3' end of the ligation product, which has a L3' linker sequence, and facilitated by an L3-L4 linker oligo. Additional barcodes can be added alternately (or in any order) to add barcodes to either side of the ligation product. Alternating between sides and ordered use of linker sequences (L1, L2, L3, L4 etc.) can reduce cross-contamination products between addition steps. Primer sequences P1 and P2' can also be added via LTL oligos (L5-L2) and (L6-L7) as shown. The resulting barcoded ligation product is 5'-P1-L5'-L2'-BC1-L1'-DR-UR-L3'-L4'-BC2-L6'-L7'-P2'-3'.

Figure 18B:
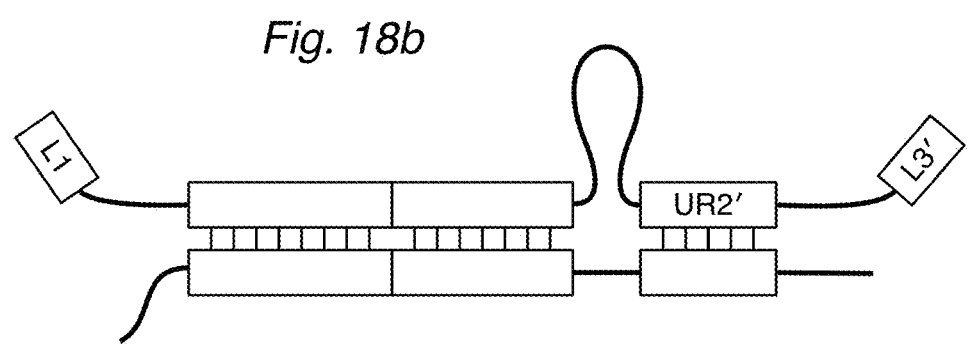
Figure 18C:
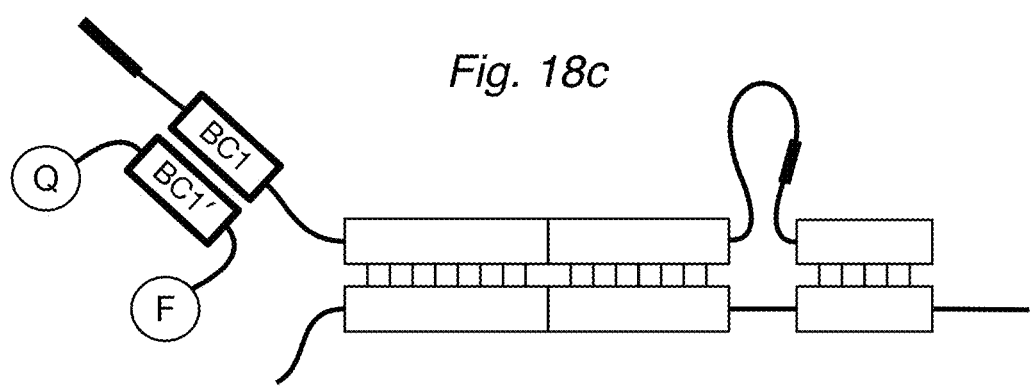

Dual addition can also be applied to anchored configurations as in FIG. 18b, where 5'-L1-UR' and UR2'-L3'-3' ends can be used to add barcoded oligos. Detection of ligation or amplification products with barcodes on both the 5' end and the 3' end serve to confirm that the specific hybridization and ligation steps occurred. The combinations of barcodes further serve to identify the population and subpopulation of samples labeled in each of the iterations.

Horseshoe Configuration

In a horseshoe-type embodiment, exemplified in FIG. 22a, a horseshoe (HS) oligo is provided having a portion complementary to a portion of one detector oligo and a portion complementary to a portion of the other detector oligo. In the particular embodiment in the figure, the horseshoe oligo has the structure 5'-L1'-P2-P3-3', where the sequences can be separated by an optional connector that is sufficiently long and flexible to permit the hybridizations shown. When both the DDO and UDO are specifically hybridized to the target sequence, the horseshoe oligo can join the two detectors in a structure that has a 5'-L1' sequence. The L1' sequence can be used to support the addition of barcoded oligos.

In FIG. 22a, two iterations of barcoded oligos are shown with supporting LTL21 and LTL43 oligos. Finally, a P1' primer sequence is attached via an L5' sequence. The resulting product can have the structure 5'-P1'-L5'-BC2-L4'-L3'-BC1-L2'-L1'-P2'-UR'-DR'-P2-3', which is suitable for amplification with primers having P1 and P2 as shown in FIG. 22b. Thus, the bridge configuration yields a product that identifies the sample and confirms specific detection of the target sequence.

Detection

The ligation product (or its amplicons) can optionally be detected by methods such as sequencing, qPCR, end point PCR, enzymatic, optical, or labeling for detection on an array or other molecule detection. Other detection methods include flow-through systems for counting labeled molecules. Depending on the detection method, the skilled user will be able to modify the design of the detectors and amplification primers to include functional features that are appropriate, such as for bridge amplification on a sequencing flow cell. Paired-end techniques can be used when the expected ligation or amplification product to be detected is greater than 80, 100, 120, 140, 150, 160, 170, 180, 190, 200, 220, 240, 260, 280, 300, 350, 400, or 500 nucleotides in length. The experimental resources used for amplification and detection can be limited and are often among the most expensive, and their consumption can be optimized by reducing the number of non-informative assay components present at various stages of the assay.

Nucleases

Accordingly, the invention provides optional nucleases and assay components that are configured to resist degradation to enable more efficient use of resources and more sensitive detection. As a further advantage, the invention enables a simpler assay workflow that can be performed in a single reaction container or entirely in liquid phase.

The nuclease can be an enzyme that digests or degrades single strands of nucleic acids. Preferably the nuclease does not digest (or has significantly less activity on) double strands, including DNA:RNA hybrids. For example, the nuclease can have less than 10%, 5%, 2%, 1%, 0.5%, 0.2%, or 0.1% the activity on double strands compared to single-strands on a molar substrate ratio under the same conditions. Similarly, the nuclease can be selected so it does not appreciably digest at single-stranded nicks in a double-strand. The nuclease can be an endonuclease that degrades single strands, such as mung bean nuclease under certain conditions. The nuclease can also be an exonuclease that degrades single strands, which can be single strands of DNA. For example, a nuclease having single-stranded 3'-to-5' exonuclease (3' exo) activity includes Exonuclease I from *E. coli* (exo I) and T3 exonuclease. Enzymes such as exonuclease T (RNase T), which has 3' exo activity on DNA and RNA single strands, can be used as long as the detectors have been ligated and the RNA strands are no longer needed in the assay. Nucleases having single-stranded 5'-to-3' exonuclease activity include exonuclease VIII and RecJ$_f$. The nuclease can be an enzyme that digests 5' overhangs or flaps, such as Flap endonuclease 1. Nucleases can be used singly or in a cocktail of nucleases, such as a pair of 3' and 5' exonucleases. A nuclease treatment step can use a double-stranded DNase (dsDNase) with relatively lower or no activity toward DNA:RNA hybrids, to remove dsDNA from RNA samples.

The nucleases can be used at various stages of the assay. For example, a nuclease can be provided (b2) after the ligation step (b1) to remove unligated or excess detectors, as in FIG. 2*e*. The nuclease can also degrade detectors that are only partially or nonspecifically hybridized to target sequences, as in FIG. 2*f*. If compatible with the ligation conditions used, the nuclease can also be provided during the ligation step (b1 and b2 together), or even before the ligation step (b2, then b1) as long as it does not interfere with the intended detection of target sequences. Depending on the assay design, the nuclease can be provided before, during, or after the optional (b0) extension and (d) amplification steps, or at multiple steps to effect the desired purpose of removing undesired target, detectors, other oligos, or any products.

When the nuclease activity is no longer desired, the nucleases can be removed or inactivated, such as after the ligation step. Nucleases can be inactivated by methods selected for a particular nuclease but will not substantially interfere with the rest of the assay. For some nucleases, a nuclease inhibitor (as in FIG. 4, lower right) or chelating agent, such as EDTA, can be added as long as it does not interfere with (or can be removed prior to) a subsequent step that may require Mg$^{++}$ for example. Other nucleases can be inactivated by heat, for example single or repeated incubation at 70° C., 75° C., 80° C., 85° C., 90° C., 95° C. or 98° C., for 1, 2, 5, 10, 15, 20, 25, 30, 45 minutes, or 1 hour. If more than one nuclease is used, either or both may be inactivated individually or by the same means. To resist the activity of nucleases provided at one or more steps of the invention, components of the assay are provided by the invention in various configurations that permit detection of target sequences. Selection of the configuration method will depend, of course, on the particular nuclease being used.

Circularizable Detectors

In a circularizable configuration with one detector, the upstream complementary region (UR') and downstream complementary region (DR') are on a single, circularizable detector oligo (DO), as shown in FIG. 3*a*. The DO can have in the 5'-to-3' direction: (B) an upstream complementary region (UR'); (C) an optional amplification region (P2'); (D) a noncomplementary region (CP2) having a sequence that is not complementary to the target sequence; (F) a downstream complementary region (DR'); and (E) an optional amplification region (P1). The DO can be at least 50, 60, 70, 80, 90, 100, 110, 120, 130, 140, 150, 200 bases in length to allow the molecule flexibility to circularize.

An alternate circularizable configuration with two detectors has a DD with a CS portion at the 5' end, and an UD with a reverse complementary CS' portion at the 3' end, so that the DD and UD are partially hybridized to each other via the CS and CS' portions. Optionally there are blocking groups at the 5' end of the CS portion or the 3' end of the CS' portion. Another circularizable configuration has three oligos: two detectors and a bridge oligo: the DD has a CS1 portion at the 5' end; the bridge oligo has a CS1' portion and a CS2' portion; and the UD has a CS2 portion at the 3' end. The bridge oligo optionally has blocking groups at the 5' end and/or the 3' end.

In the presence of a target sequence DR-UR, the circularizable detector(s) can (a) circularize on the target, forming a hybridization complex (HC) that is resistant to single-stranded exonucleases and that can be (b2) ligated.

If the amplification regions are provided in the appropriate orientation, the ligation product (LP) can be (c) amplified with P1 and P2 primers to form amplification product (AP) that contains the joined DR' and UR' regions.

The DOs that are not specifically hybridized to the target or are bound incompletely to the target are susceptible to degradation by nucleases (FIG. 3*d*) or the P1 and P2' amplification regions will not be in the correct orientations for primer amplification, as illustrated in FIG. 3*b* or 3*c*. In some instances, the detector may be amplified, but it will be amplified linearly, rather than exponentially. In such cases, the minor sequences can be detected and discounted or removed from the detection results computationally.

Second Single-Strand (2S)

Still another configuration provides a single-stranded DNA oligonucleotide (2S) to hybridize to the single-stranded portion of the detector to form a double-stranded hybridization complex, as illustrated in FIG. 4. The 2S oligo can be complementary to the CP1 so that the entire structure becomes double-stranded. Where the assay is intended to detect multiple target sequences, the same 2S can be used generically to form the circular structure since it does not rely on hybridization to target sequences. The structure can then be ligated, completing the circular, double-stranded structure and resistant to exonucleases, ss-endonucleases, and nick-endonucleases.

Optionally, the circular structure can be deliberately nicked or cut, for example by a nicking endonuclease. The DO can have a restriction endonuclease recognition site so the circular structure can be linearized if desired. To avoid digesting target sequences or detectors, the recognition site selected for CP1 can be a relatively rare site such as for AscI, FseI, AsiSI. If desired, linearized structures can be separated from circular structures by conventional methods.

Flaps

Figure 5E:
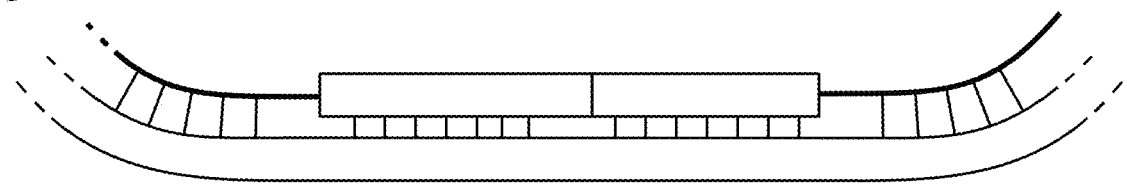

The circularizable DO can be configured so that it has a (A) a noncomplementary region (CP5) in the 5' direction of the UR' and (G) an optional noncomplementary region (CP3) in the 3' direction of the DR', as shown in FIG. 5*a* and discussed in Example 4. A second strand can be provided that has, in the 5'-to-3' direction: P2, CP2', P1' so that, together, the target nucleic acid, a detector oligo, and the second strand form a hybridization complex having a 5' flap. A nuclease, such as Fen-1 can be used to remove the 5' flap (FIG. 5b). The 5' end of the circularizable detector can be phosphorylated (FIG. 5c). If desired, the optional CP3 region can then hybridize to the target sequence, forming a 3' terminus that can be ligated (FIG. 5d) to the adjacent UR' to form a ligated product (FIG. 5e).

Steps in Solid, Liquid Phases

In other embodiments, one or more of the steps can be performed in liquid phase, such as in a microfluidic system, so that one or more of the steps does not involve capture to a solid phase, such as to a bead or a plate surface. For example, any one or combination of the hybridization, extension, ligation, nuclease digestion, amplification, or detection steps can be performed in liquid phase.

In some embodiments, the sample is provided in a solid phase, such as an FFPE, so that it remains in solid phase for one or more steps of the detection process. When in solid phase, the sample can be washed between steps to remove unused assay components or to reduce background, for example after hybridization or after ligation.

In a mixed phase assay, a solid phase can be used to immobilize one or more of the sample, the detector oligos, the hybridization complex, the extension product, the ligation product, or the amplification product. For example, a capture oligo can have a sequence complementary to a portion of the target sequence. In addition to capture oligos, other nucleic acids that can be immobilized onto a solid phase include horseshoe oligos, linker oligos, splint oligos, barcoded oligos, primers. For example, a nucleic acid can be attached to one member of a binding pair, such as the pairs biotin-streptavidin, antibody-antigen, or sugar-lectin, such as Concanavalin A. The capture oligo can also have a sequence that is complementary to a splint sequence of a barcoded oligo, which can have a barcode sequence and a splint sequence.

In particular, the target nucleic acid can be attached to a solid surface during the hybridization step, the ligation step, or both. The solid surface can be a bead, such as a magnetic, nonmagnetic, polymeric, reversible immobilization, or latex bead, or compound beads thereof, or a relatively flat surface such as a plate or flowcell surface, optionally with coatings of similar materials. The mixed phase format allows the components to be transferred from one reaction environment to another, or the conditions to be changed as the components remain in one container.

Adding Successively to the Same Reaction Container

Alternatively, the reactions can be optimized so that at least one of steps is performed by adding reagent, such as an enzyme or buffer component, successively, so that a reaction takes place in the same container as the preceding step, optionally without requiring an intervening wash or transfer step. Preferably, the sequence of additions does not require significant additions of liquid volumes to dilute the components for the next reaction, for example no more than 1-, 1.5-, 2-, 2.5-, 3-, 5-, 10-, 15-, or 20-fold dilution between the initial sample and preparation for detection. The components to be added can be provided in a kit, as described below.

Steps In Situ; Cross-Linking, Photocleavage, Elution

In some embodiments, the hybridization, ligation, or extension steps can be performed while the target sequence is in situ, as with FFPE samples. This can be particularly useful, for example, when the sample is on a histological slide, so that the ligation is known to occur at a recordable location and can be compared to similar reactions at other locations on the slide. It useful for any sample where the target sequence is part of a nucleic acid is fixed to the tissue. The ligated probes can remain at the location while other steps are performed, such as imaging or detection of other analytes at or near the location. These other analytes can be any of the nucleic acids described herein, including modified nucleotides, carbohydrates or lectins, proteins and other antigens, and any other stainable molecule or feature that can be visualized. These other analytes in situ can be present on the surface of the sample, treated to expose them on the surface, or be made accessible to reagents such as stains to aid their visualization, such as by permeabilization.

If desired, the ligated probes can remain in situ more securely by a variety of chemical or enzymatic methods for cross-linking to the site, which can be permanent or reversible, such as by a photocleavable link as with using a cyanovinylcarbazole nucleoside analog ($^{CNV}K$). The area to be photocleaved can be any shape or size, and can be focused on one or a few selected cells of interest, or can focus on a histological or pathological feature. The photocleavage steps may also be performed whether the sample is wet or dry.

In a particular embodiment, the ligation products can be eluted from the sample in situ for collection and further processing, preferably eluting from small areas to preserve the location information and morphological context of the ligation reaction products. Elution can simply be by heat in low salt, effected by the PCR process, or by addition of base. The eluted area can be smaller than 2 mm$^2$, 1, 0.5, 0.2, 0.1, 0.05, 0.02, 0.01, 0.005, 0.002, 0.001 mm$^2$ (1000 μm$^2$), 500 μm$^2$, which covers the range of single human cells of many types.

Photocleavage and elution steps can be coordinated so a first area is photocleaved, followed by elution of a second area. The first and second areas can be coextensive, overlap, or be larger or smaller relative to each other. In other combinations, an area may first be nonspecifically washed or selectively eluted for some components, then photocleaved, followed by elution and collection of other components.

In a particular embodiment, samples are dried, fixed, optionally permeabilized, and optionally processed prior to or during the assay. In yet another embodiment, samples are simply preserved by fixation before the assay.

TempO-Seq™ Assays

Standard Version

A "standard" version of the TempO-Seq™ assay provides a method for detecting target nucleic acid sequences in a sample, wherein a target sequence has a downstream region (DR) and an upstream region (UR). The steps include (a) contacting the sample with a pair of detector oligos. The detector pair comprises a downstream detector oligo (DD) having a complementary downstream region (DR') and a separate upstream detector oligo (UD) having a complementary upstream region (UR'). At least one of the DD or UD can have a second complementary region (DR2' or UR2') separated from the DR' or UR' by a noncomplementary region (CP1) that does not hybridize to the target nucleic acid. Thus, a DR2' or UR2' can specifically hybridize to a DR2 or UR2 of the target nucleic acid. This allows the pair of detectors to hybridize specifically to the target nucleic acids. The method continues by (b1) ligating the DR' and UR' if both are specifically hybridized to the DR and UR of a target sequence. The hybridization complexes can be exposed to at least one nuclease that degrades single strands but does not significantly degrade double strands. Thus, nonspecifically hybridized DDs and UDs can be degraded by the nuclease. The ligation product serves as an analytical product that indicates the presence of the target sequence in the sample.

In a particular embodiment, the assay targets 50 nucleotide regions in RNAs with pairs of detector oligos (DOs), which share universal PCR primer landing sites. After annealing, the adjacent DOs are ligated together and amplified by PCR (which can also add sample tag sequences and sequencing adapters). A single PCR can primer pair amplify all ligated probes in a single sample. Attaching unique tag sequences that are sample-specific can allow sample pooling into a sequencing library of 384 or more samples per flow cell.

As disclosed above, the sample can be a tissue sample, can be mounted on a slide, or can be an FFPE. The target nucleic acid can be from an FFPE sample, or can be in situ. The standard version can have a step of eluting the ligation product.

The standard assay can be performed with FFPE samples, as discussed in Example 7 and illustrated in FIG. 8.

The TempO-Seq™ assay is commercially available as a kit in a Whole Transcriptome version (BioSpyder Technologies, Inc., Carlsbad, Calif.).

Modified Version of TempO-Seq™ Assay

A "modified" version of the assay is described in Example 5 and illustrated in FIG. 7.

In Situ Version of TempO-Seq™ Assay

An in situ version of the assay is described in Example 7 and illustrated in FIG. 8. In this version, probes that are not bound to the sample can be washed away, reducing assay background, and increasing specificity and overall sensitivity. The method can detect a nucleic acid sequence from a selected area of a sample in situ, by performing in any order: imaging the sample for the presence or absence of an analyte; selecting an area of the sample based on the imaging; detecting a target nucleic acid sequence by any of the detection methods for nucleic acid sequences herein; and collecting the ligation products from the selected area for analysis.

The selected area can be a morphological feature, which can be visualized by one or more stains. Any histologic stain can be used to image the sample. Useful stains include fluorescent dyes, enzymes (such as peroxidase or alkaline phosphatase), as well as radioactive labels. Immunostaining or other antibody-based staining methods can be used, including immunohistochemical staining of tissue sections.

The analytes can be any of the nucleic acids or modified versions described herein. More generally, the analytes can be any detectable molecule such as proteins, carbohydrates, or their binding partners or stain components.

The detection of many antigens can be improved by antigen retrieval methods that break some of the protein cross-links that may have form during fixation, thereby uncovering previously hidden antigenic sites. Retrieval methods include heating, such as heat-induced epitope retrieval (HIER) and using enzyme digestion, such as proteolytic induced epitope retrieval (PIER).

Individual steps in this version can be automated or performed manually, or using any slide-staining apparatus where temperature can be controlled during incubations.

Attenuators

In cases where there is more than one target sequence in a given sample, it is likely that they will be present in different amounts. Moreover, the amount of a target sequence can vary among similar samples. Ideally, a detection assay will have sufficient dynamic range to measure the presence of the different target sequences quantitatively in a single experiment. For some types of samples, however, the range of abundance for various target sequences can span several orders of magnitude. For example, when profiling the RNA expression products of a cell, individual sequences of particular interest may be present in very few copies, while others are highly abundant target sequences (HATs). The HATs can be present in a sample in such large numbers that they may diminish the ability of a method to detect the presence of less abundant target sequences.

Depending on the cell or tissue type, such highly abundant HATs can include sequences encoding what are generally referred to as housekeeping genes. Examples of HATs include sequences that encode all or a portion of myoglobins, actins, tubulins, ubiquitins, heat-shock proteins (HSPs), histone proteins, ribosomal proteins, ribosomal RNAs (rRNAs), micro-RNAs (miRNAs), or small nuclear RNAs (snRNAs). Other examples of HATs can encode all or a portion of cytochrome c, glyceraldehyde 3-phosphate dehydrogenase (GAPDH), ribosomal protein L7 (RPL7), ribosomal protein S6 (rpS6), snRNA RNUs, phosphoglycerokinase (PGK), tyrosine 3-monooxygenase/tryptophan 5-moonoxygenase activation protein zeta (YWHAZ), β-actin, or β-tubulin. Further examples include sequences encoding all or a portion of α-2-microglobulin, vimentin, and fibronectins. Yet other examples of HATs encode all or part of a cytochrome such as mitochondrially encoded cytochrome b (MT-CYB), outer mitochondrial membrane cytochrome b5 type B, microsomal cytochrome b5 type A (ACYB5A), and ascorbate-dependent cytochrome b3 (CYBASC3). HAT sequences can include host sequences when the target sequence is from a microorganism, bacterium, or virus that infects host cells.

Because which sequences are highly abundant can differ from one sample type to another, such as between different tissues or cell types, certain target sequences can be designated as a predetermined set of potential HATs based on a search of the literature for that type of sample, or can be determined by performing preliminary assays to determine the more abundant sequences in the sample type. Various attenuator oligonucleotides ("attenuators") can be used to attenuate the overall number of HAT-related ligation products to be detected. Some attenuators are provided that can to provide positive detection of the HAT in the sample, but at a lower level of signal.

An attenuator useful in the invention is shown in FIG. 2g, where a UR2' oligo is provided to hybridize to UR2 targets in competition with detectors. Similarly, UR2, DR2', and DR2 oligos can be provided to compete with the binding of portions of anchored detectors to HATs, thereby attenuating the total number of detectors that form HAT-related ligation products. Particularly useful attenuators can have a portion of DR2 and a portion of DR; or have a portion of UR and a portion of UR2, thereby competing for two portions of the same anchored detector.

For circularizable detector designs, an attenuator can be an oligonucleotide that has a portion that is identical or complementary to UR or DR, or both. Attenuators can also take the form of oligos that fill a gap, such as shown in FIG. 5b, but are blocked from yielding a ligatable product.

Kits

The invention provides kits for performing the methods described above, comprising detector oligos, and optionally a nuclease, a ligase, and/or a polymerase (for extension or for amplification). The kits can further provide reaction buffers for the enzymes in the kit or buffer components to be added to reactions suitable for the enzymes. The component can be suitable for addition to a container for an enzyme reaction to prepare a suitable reaction buffer for the enzyme. The component can also be selected to be compatible with the reaction buffer for the preceding step of the method so that the component can be added to the same container to form a reaction buffer for the next enzyme to be used. Thus, the components can be selected to enable an "add-add-add" strategy for multiple steps of the assay to minimize transfers of sample, oligos, enzymes and/or solutions between separate containers, thereby reducing the risk of aerosolization of potentially infectious or otherwise hazardous nucleic acid samples.

The kits can also have eluent solutions suitable for removing oligonucleotides, such as ligated oligonucleotides, from a tissue sample for further analysis. The kits can further have amplification primers suitable for use with the detectors of the kit.

As disclosed above, the kit can have a pair of detector oligos, which pair comprises a downstream detector oligo (DD) having a complementary downstream region (DR') and a separate upstream detector oligo (UD) having a complementary upstream region (UR'). The downstream detector (DD) or the upstream detector (UD) can have a second complementary region (DR2' or UR2') separated from the DR' or UR' by a noncomplementary region (CP1) that does not hybridize to the target nucleic acid and that has an amplification region (P1 or P2'), whereby the DR2' or UR2' can specifically hybridize to a DR2 or UR2 of the target nucleic acid. The detector oligos can themselves be labeled with one or more barcode sequences, such as in FIG. 19a or 21a. Kits can also include one or more eluent solutions to remove oligos, such as unligated detectors, or in a separate step, to elute ligation products from the tissue sample.

The kits can also contain a stain, such as a histological stain, such as hemotoxylin or eosin. The stain can also have an antibody, such as for immunostaining, for detecting an analyte in the sample, as described herein.

Kits for performing TempO-Bar methods can further include sets of barcoded oligos that are capable of being attached to a detector oligo or to another barcoded oligo. A set of barcoded oligos can have a portion complementary to a portion of a detector oligo. For example, the invention provides B1 oligos as in FIG. 15a. The barcoded oligos can also have another portion that is complementary to a portion of other barcoded oligos, such as an L1, L2, L3 etc. sequence. If desired, a set of terminal ("B2") barcoded oligos can be provided where a barcode sequence is incorporated into a set of amplification primers.

The barcoded detectors can be supplied in a container having different subcontainers, such as a multi-well plate with different barcoded oligos in each well. When the kit is to be used with multiple orthogonal rounds barcoding, the kit can contain multiple plates with barcoded oligos for each round.

The TempO-Bar kit can also include a ligation template linker (LTL) that has a portion complementary to P1 and a portion complementary to an L portion. An LTL can also have one or more linker sequences, as illustrated in FIG. 15a.

Other oligos that can be provided in the kit include bridge oligos and horseshoe oligos.

The oligos in the kit can be functionalized with a group to enable click chemistry reactions to attach the oligos to other oligos or molecules. For example, 5'-iodo detector oligos are illustrated in FIG. 17.

Diagnostic and Other Methods

The present invention provides a method for detecting a neoplastic state of a cell by detecting one or more cancer marker sequence in a cell. As shown in Table 3 below, in a selected are, ligation products of a second cancer marker sequence can be detected in significantly fewer numbers, such as less than 0.1%, 0.05%, 0.02%, 0.01% or 0.005% than the first cancer marker sequence.

The invention provides methods for generating a gene expression profile for a selected area for a plurality of target sequences.

The invention also provides methods for detecting a neoplastic state of a cells in a tissue detecting a plurality cancer marker sequences on cells in two separate areas of the tissue.

The invention further provides methods for diagnosing a disease state wherein the target sequences are detected in the area of a morphological feature.

Instruments

The invention provides instruments, which can be automated, for imaging samples such as FFPEs or slides, selecting focal areas, and eluting to recover analytes from those areas. The instrument can have an imaging component, a component for collecting ligation products from the selected area, and a component for transferring the products to an external container.

An example of the instruments of the invention is the CellSensus™ digital molecular pathology platform. This platform combines a digital imager for slides, and a mechanism for automatically recovering probes from selected areas, and transferring them, for example to PCR tubes. The platform also includes software to control some or all of these functions and perform analysis.

EXAMPLES

Example 1: Representative Ligation Assay

A representative method is provided to illustrate ligation assays. Here, over 100 RNA expression products were detected in a sample of cells using a multiplex assay format. For each expression product, the assay was designed to detect one or more target sequences within the full sequence of the product. For example, in human cells, a GAPDH gene of interest encodes the enzyme glyceraldehyde 3-phosphate dehydrogenase; three different portions within the RNA transcript of the GAPDH gene were independently detected as target sequences. One such RNA target sequence, identified here as GAPDH_2, was (SEQ ID NO: 4)
5'-<u>CGACCACUUUGUCAAGCUCAUUUCCUGG</u>UAUGACAACGAAUUUGGCU ACA-3' where a 5' end was designated "upstream" (underlined) and the 3' end was designated "downstream" for the direction of transcription and translation. The same GAPDH_2 target sequence can be shown in the 3'-to-5' direction for later convenience of discussion. A downstream region (DR) was defined as the downstream 25 bases of GAPDH_2, which has a complementary DNA sequence of DR'. The upstream region (UR) was defined as the upstream 25 bases of GAPDH_2, which has a complementary DNA sequence of UR'.

(SEQ ID NO: 5)
3'-ACAUCGGUUUAAGCAACAGUAU<u>GGUCCUUUACUCGAACUGUUUCAC CAGC</u>-5'

A downstream region (DR) was defined as the downstream 25 bases of GAPDH_2:

(SEQ ID NO: 6)
3'-ACAUCGGUUUAAGCAACAGUAUGGU-5' which has a complementary DNA sequence of DR':

(SEQ ID NO: 7)
5'-TGTAGCCAAATTCGTTGTCATACCA-3'

The upstream region (UR) was defined as the upstream 25 bases of GAPDH_2:

(SEQ ID NO: 8)
3'-CCUUUACUCGAACUGUUUCACCAGC-5' which has a complementary DNA sequence of UR':

(SEQ ID NO: 9)
5'-GGAAATGAGCTTGACAAAGTGGTCG-3'

For GAPDH_2, a pair of detectors was designed: a downstream detector (DD) having the DR' sequence, and an upstream detector (UD) having the UR' sequence. Similar pairs were designed for each of the target sequences to provide a pool of detectors for the assay. In this example, all the upstream detectors were phosphorylated at the 5' end.

In this particular example, an amplification step was to be performed later in the experiment using two primers, P1 and P2, so all UDs in the experiment included a primer sequence (P1) and all URs included a complementary primer sequence (P2'). Because amplification is not necessary to the practice of the invention, however, the sequence of the specific primers and primer sequences is a matter of selection to suit the particular amplification method, if used.

At least 10 ng of RNA isolated from human kidney or liver cell lines was placed in a well of a microtiter plate for each assay experiment. To each well was added 20 µL of 2× Binding Cocktail, which contained 5 nM of each detector (providing a final input of 0.1 pmoles per oligo), 100 nM biotinylated oligo(dT)$_{25}$, and 5 µL streptavidin-coated magnetic beads in a Wash Buffer (40 mM Tris-Cl pH 7.6, 1 M NaCl, 2 mM EDTA disodium, 0.2% SDS).

The plate was heated for 10 min at 65° C. to denature the RNA, then the temperature was ramped down over 40 min to 45° C. to allow the detectors to anneal to the target sequences in the RNA sample. The plate was then transferred to a magnetic base to immobilize the beads, allowing the supernatant, containing unbound and excess detectors, to be aspirated from the wells. The beads were washed at least three times with 50 µL Wash Buffer.

To each well was added 5 Weiss units of T4 DNA ligase in 20 µL of 1× ligation buffer, as provided by the supplier. After the beads were resuspended by pipette, the plates were incubated for 60 min at 37° C. to allow target-dependent ligation of DDs to UDs as appropriate. After the ligation reaction, the beads were immobilized and washed twice with 50 µL Wash Buffer. To release the ligated detectors from their RNA targets, the beads were resuspended in 30 µL and incubated for 5 min at 65° C. After incubation, the beads were immobilized, and the supernatant was removed and transferred to a storage plate.

For the optional amplification step, 5 µL of the supernatant, containing the ligation products, was transferred to a well of a PCR plate. Then 10 µL of a PCR cocktail was added, containing 0.45 U Taq polymerase, 0.6 µM P1 primer, 0.6 µM P2 primer, 1.5 mM MgCl$_2$, and 200 µM dNTPs. The thermocycler used the following program: 10 min at 94° C., followed by 20 to 25 cycles of 30 sec at 94° C., 30 sec at 58° C., and 30 sec at 72° C. The amplification products were then sequenced according to manufacturer's instructions.

This representative ligation assay can be modified as in the following examples.

Example 2: Anchored Detector Designs

Upstream and downstream detector probe oligonucleotides were prepared as in FIGS. 2a and 3a for 24 target sequences identified as breast cancer targets: ACTB_1, TFF1_1, GATA3_3, GAPDH_3, CDH1_1, KRT19_2, TIMP1_2, NFKBIA_1, ESR1_1, VEGFA_3, LAMP1_2, MUC1_3, BAD_3, PTEN_1, BRCA2_1, BCAT2_3, ICAM1_2, IGF2_3, BRCA1_2, EGFR_1, BMP4_1, KIT_3, WNT1_1, and EGF_3 (in descending order of expected counts). The targets were selected for a range of expression covering 6 orders of magnitude from ACTB_1 to EGF_3. The target sequences used for the DRs and URs are shown in FIG. 6a.

The assay was performed in triplicate with 100, 10, 1, and 0.1 and 0 (control) nanograms of MCF7 total RNA as sample. The detectors were added to the sample in a volume of 1 or 2 µL and allowed to hybridize by incubating at 65° C. for 10 minutes, ramping down over 20 minutes from 65° to 45° C., then held for 20 minutes at 45° C. Exonuclease I (E. coli) was added to the hybridization mixture in 6 µL of 0.5 Units and incubated for 1 hour at 37° C. T4 ligase was added to the mixture in 6 µL of 5 Units and incubated for 1 hour at 37° C. A heat step was performed for 30 minutes at 80° C. The mixture was amplified by adding 2×PCR master mix. The amplification products corresponding to the target sequences were detected and quantificated by qPCR and sequencing. The results are provided in FIGS. 6b-6g.

Example 3a: Circularizable Detector Design for microRNAs

Circularizable DO detectors were designed for the Let-7 family of miRNAs. These miRNAs are initially transcribed as relatively long transcripts (pri-miRNAs), but are processed into pre-miRNAs, and subsequently processed into a relatively short mature form. In mature form, the highly homologous Let-7 family is shown 5'-to-3', with variants from the let-7a sequence bolded).

| Hsa let-7a | ugagguaguagguuguauaguu | SEQ ID NO: 10 |
| Hsa let-7b | ugagguaguagguugugugguu | SEQ ID NO: 11 |
| Hsa let-7c | ugagguaguagguuguaugguu | SEQ ID NO: 12 |
| Hsa let-7d | agagguaguagguugcauaguu | SEQ ID NO: 13 |
| Hsa let-7e | ugagguaggagguuguauaguu | SEQ ID NO: 14 |
| Hsa let-7f | ugagguaguagauuguauaguu | SEQ ID NO: 15 |
| Hsa let-7g | ugagguaguaguuuguacaguu | SEQ ID NO: 16 |
| Hsa let-7h | ugagguaguaguuugugcuguu | SEQ ID NO: 17 |

Using Hsa let-7a as an example, the DR' was 5'-AACTATA-CAAC-3' (SEQ ID NO:18) and the UR' was 5'-CTAC-TACCTCA-3' (SEQ ID NO:19). A single-stranded DNA oligonucleotide (2S), about 80 nucleotides, is provided to hybridize to the single-stranded portion of the DO to form a double-stranded hybridization complex, as illustrated in FIG. 4.

After hybridization, the region of the DR and UR can be represented as

```
5'-...TAAGAG-AACTATACAAC CTACTACCTCA-CGGAAC...-3'   SEQ ID NO: 20
        ||||||||| ||||||||||| ||||||||||| ||||||||
3'-...ATTCTC uugauauguug-gaugauggagu GCCTTG...-5'   SEQ ID NO: 21
``` where the target miRNA is in lowercase. Part of the DO is shown as the upper sequence, with the DR' in roman and the UR' underlined roman, flanked by sequence, partially shown, in italics, such as P1 or P2'. The bases in bolded italics represent the 3' end (on the left) and the 5' end (on the right) of the same 2S oligonucleotide.

After ligation, the portion shown forms a double-stranded structure without any nicks

```
5'-...TAAGAG-AACTATACAAC-CTACTACCTCA-CGGAAC...-3'   SEQ ID NO: 22
        ||||||||| ||||||||||| ||||||||||| ||||||||
3'-...ATTCTC-uugauauguug-gaugauggagu-GCCTTG...-5'   SEQ ID NO: 23
``` which is resistant to attack by exonucleases.

If the DO for let-7a becomes hybridized to similar let-7c, the following structure is formed:

```
5'-...TAAGAG-AACTATACAAC-CTACTACCTCA-CGGAAC...-3'   SEQ ID NO: 24
        ||||||||| ||||||||||| ||||||||||| ||||||||
3'-...ATTCTC-uugguauguug-gaugauggagu-GCCTTG...-5'   SEQ ID NO: 25
```

The complex, which contains a mismatch, can be nicked with a variety of enzymes, such as T4 endonuclease VII, T7 endonuclease I, or in combinations of exonuclease I and *E. coli* exonuclease III, Si nuclease, or nuclease BAL-31. The nicked complex can then be degraded by treatment with a nuclease in step (b1) so that no ligation product is formed.

As illustrated, the covalently circularized, double-stranded structure can be linearized by treatment with a restriction endonuclease, if desired, where the 2S contains an appropriate restriction site. The linearized product can be amplified with primers.

Example 3b: Extended Detector Design for microRNAs

Extended detectors were designed for Let-7 family microRNAs that have been polyadenylated. The microRNAs are extended using polynucleotide adenylyltransferase to add a 3' polyadenine tail. For a Hsa let-7a microRNA (SEQ ID NO:10), a polyadenylated sequence is shown below (SEQ ID NO:28) in italics. An upstream detector is provided having SEQ ID NO:27 and an extended downstream detector is provided having SEQ ID NO:26, which has an italicized poly-T region (usually poly-dT if the detector is DNA).

```
5'-...TTTTTTTTAACTATAC AACCTACTACCTCA...-3'   SEQ ID NO: 26, 27
       |||||||||||||||| ||||||||||||||
        3'-aaaaauugauaug-uuggaugauggagu-5'   SEQ ID NO: 28
```

The combination of the supplemental 3' polyadenine tail and the extended poly-T region provides a longer complementary region for hybridization of the target to the detector, and allows greater freedom of designing DRs and URs for the target. For instance, the lengths of the complementary regions for the DD and UD can be more similar in length. When a family of related target sequences is being detected, a DD or UD can be used to detect more than one family member (a "generic detector"). Thus for Hsa let-7b,

```
5'-...TTTTTTTTAACCACAC AACCTACTACCTCA...-3'   SEQ ID NO: 29, 27
        |||||||||||||| ||||||||||||||
     3'-aaaaauuggugug-uuggaugauggagu-5'        SEQ ID NO: 30
``` the same upstream detector can be used to detect let-7a and let-7b (and let-7c), since the 14 bases in the 5' direction are identical. Skilled artisans will be able to design various combinations of specific and generic detectors for related sequences, such as the let-7 family, depending on the number of detectors and hybridization properties desired.

After the extended detectors are allowed to hybridize to the polyadenylated microRNAs, the detectors are ligated to form the ligation product for detection or optional amplification. If the number of supplemental adenosines added is fewer than the number of dTs in the DD, this does not interfere with the ligation and subsequent steps. If the number of supplemental As is greater, then excess portion of the 3' tail need not hybridize entirely to the remaining 5' portion of the DD for specific and target-valid ligation to occur.

Example 4: Flap Design

Circularizable detector oligos were designed as in Example 3a, but where the UD has an additional poly-A CP5 sequence at the 5' end:

```
                                    SEQ ID NO: 31
     5'-AAA-CTACTACCTCA-CGGAAC...-3'
            ||||||||||| ||||||||
```

After hybridization of the DO to the target sequence, the UR' (underlined above) of the DO is hybridized to the target UR, but the poly-A sequence remains an unhybridized flap, as shown in FIG. 5a. The complex can be treated with a flap endonuclease, such as Fen-1, to remove the poly-A and the adjacent hybridized base. A DR' hybridized to an adjacent DR can be extended as in step (b0) of FIG. 1 and then ligated to the UR' region.

Alternatively, the DR' can have a noncomplementary portion (CP3), such as the single C underlined below:

```
                                    SEQ ID NO: 32
     5'-...TAAGAG-AACTATACAAC-C-3'
           |||||||| |||||||||||||
``` that can hybridize and fill the gap left by the endonuclease, as shown in FIG. 5d. After ligation, a nickless double-stranded complex is formed as in FIG. 5e. The circularized structure can be linearized, if desired, and amplified, as illustrated earlier in FIG. 4.

Example 5: Modified TempO-Seq™ Assay

Defining the nature of stochastic gene expression is important for understanding the regulation of transcription/translation and cell population dynamics. Jurkat cells and human blood lymphocytes (activated ex vivo, fixed, permeabilized, antibody-stained for surface CD4 and CD8, and for intracellular transcription factors FoxP3 and EOMES) were prepared. A modified version of whole transcriptome TempO-Seq™ gene expression assay was performed in situ, and the cells were FACS-sorted into bulk subpopulations or into single cells. In this modified version, the probes were eluted and gene expression was profiled by sequencing. The modified assay (based on the NIEHS S1500 gene-set) measured 2977 genes ("surrogate whole transcriptome" or "surrogate" assay, compared to the more comprehensive TempO-Seq™ "whole transcriptome" assay), identifying every known signaling pathway. Bulk cell measurements correlated with the summed single cell measurements ($R^2=0.89$ for a bulk preparation of 1000 CD4-/FoxP3-cells versus single cells). The no-sample control background was <0.06 counts, showing that true "off" could be measured. The "abundance" of genes measured in bulk samples correlated to the number of cells in which expression was "on", a measure of the percentage of time that the gene is on. Only 48 genes were expressed all the time in every single cell, while the rest exhibited no expression in one or more cells. It was observed that most genes were either on or off with very little "ramp up" or "ramp down" of expression over the time required to fix the cells and stop RNA synthesis/degradation.

If a simple average is used to compare the single-cell population to the bulk population, the expression behavior of individual cells over time may be masked behind a single average value for the expression of the bulk population as a whole. When the bulk measurement was 10 counts, 247 cells had 0 expression, 6 had a median expression of 500 (average 583), ranging from 149 to 1206 counts, compared to the highest expressed gene, average counts 12,541, range 7,519 to 18,970; only ~16-fold higher. Thus, the concept of single copy gene expression is more complex than previously understood. Rather, low-expressed genes are "off" most of the time, but when "on" they are at relatively high levels in a cell. This in turn drives up "average" expression levels if measured in larger populations of nonactive cells.

FIG. 7 shows a modified version of the TempO-Seq™ assay that can be performed after antibody-staining, before flow cytometry sorting (FACS). A reagent was used to permeabilize the cells, which provided highly sensitive antibody-staining of intracellular antigens. The protocol was carried out by adding a cocktail of detector oligos (DOs) so that there was a pair of DOs that hybridized to each targeted RNA, and when properly hybridized, the two detector oligos butt up against one another, permitting ligation. Wash steps were used to remove excess nonhybridized DOs, and subsequently, unligated DOs. The FACS sorting was performed, capturing each cell into 10 ml of PCR buffer, and then universal PCR was carried out to amplify the products and at the same time to add a sample-specific barcode to the product from each cell.

Example 6: Detection of Methylated Targets

A full-length mRNA for GAPDH has three target sequences GAPDH_1, GAPDH_2, and GAPDH_3, each target 50 bases in length. GAPDH_1 is upstream of a splice site, and has a position suspected of having an m'A modification at position 26, near a start codon. Pairs of detectors for each of the three target sequences are provided, where performing the assay as disclosed herein can generate countable amplicons corresponding to GAPDH_1, _2, and _3 respectively, indicating those target sequences are present in the mRNA sample. The count numbers may be adjusted quantitatively for minor count variations observed when detecting the three targets, when the GAPDH targets are known to be present in equimolar amounts. However, the detectors for GAPDH_1 generate no (or substantially fewer) countable amplicons when the m'A modification is present at position 26, compared to the expected counts with no modification at position 26. The detectors for GAPDH_2 and _3 can thus serve as positive controls for the presence of the full-length mRNA, regardless of m'A modification at position 26. Thus, the invention provides a method for detecting the presence of modifications, such as methylation, at positions of interest in the nucleic acids of a sample.

Example 7: Processing FFPE Tissues Using the Standard TempO-Seq™ FFPE Protocol and Performance Profiling of H&E-Stained FFPEs FFPE samples can be used in the standard TempO-Seq™ assay. In the FFPE preparation protocol, the FFPE was unstained, antibody stained, or H&E stained. A 1-2 $mm^2$ area of a 5 µm thick section of FFPE was sufficient, making TMAs, core biopsies, FNAs suitable for assay. The sample can be slide mounted or a curl.

FFPEs from five prostate cancer patients were H&E stained. Then 1 $mm^2$ areas were identified for prostate: normal, adjacent high grade prostatic intraepithelial neoplasia (PIN) or cancer epithelium. The areas were scraped and processed through the standard TempO-Seq™ assay for whole transcriptome. In FIG. 9, differential expression between normal and PIN versus normal and cancer was determined and plotted ($log_2$-fold change) for statistically significant genes (adjusted p-value <0.05). Most genes that were differentially expressed in cancer were also differentially expressed in high grade PIN, indicating that at the molecular level, high grad PIN adjacent to cancer is in fact cancer in situ.

Example 8: Automated In Situ CellSensus™ Assay Process

The in situ TempO-Seq™ protocol was performed directly on slide-mounted FFPE tissue using an automated stainer (Bond RX, Leica BioSystems Inc., Buffalo Grove, Ill.). As illustrated in FIG. 6, the FFPE sample was deparaffinized and processed by the automated stainer through the point of detector oligo ligation. The automated stainer then stained the slides with antibodies (such as an anti-CD3 antibody) or optionally H&E (hematoxylin and eosin), performing (as desired) some of the staining steps manually, such as staining with eosine. The staining step includes immunostaining. The CellSensus™ imaging platform was used to perform pathological analysis and to image, and identify, select and/or mark areas for profiling.

The imager then automatically recovered probes from those areas and transferred them into PCR tubes that were processed through the remaining steps of the assay protocol described herein, including amplification, qPCR, and sequencing. The data was analyzed by TempO-SeqR™ software to generate a report. Any number of imaging platforms could have been used with appropriate hardware for elution, such as a capillary with fluidic control for applying the elution buffer to the surface of the sample.

Example 9: Single Cell Sensitivity

MCF-7 cells were processed through the in situ TempO-Seq™ Whole Transcriptome assay, then separated either by fluorescence-activated cell sorting (FACS) or Cytospin™ cytocentrifuge (Thermo Fisher Scientific, Waltham, Mass.). The Cytospin-separated cells were then picked by the CellSensus™ system. In FIG. 11, panel (A) shows correlation of an assay of bulk 200 cells versus a single FACS-sorted cell. Panel (B) shows the correlation of the same 200-cell bulk and a single cell profiled using the CellSensus™ instrument. Panel (C) shows correlation of one single cell isolated by FACS versus a single cell isolated by the CellSensus™ instrument. Stochastic gene expression was observed in single cells, with genes measured as expressed in bulk but not expressed in some of the individual single cells. Panel C shows genes that were expressed by one single cell but not another, and vice versa. Low-expressed genes were nevertheless measurable from single cells regardless of how they were picked, whether by FACS or by the CellSensus™ instrument.

Example 10: Focal Elution from FFPE Samples

Breast FFPE was processed through the in situ assay on the Bond RX, then H&E stained. Areas of interest for profiling were digitally marked while performing IHC. The CellSensus™ instrument then carried out automated elution. A reagent in the eluent destained the exposed area, providing a positive record of the area profiled. This is evident from the pre-elution and post elution images in FIG. 12. The intensity of the blue staining was scanned in the pre- and post-elution images, clearly demonstrating the destaining and the ability of the CellSensus™ imager to assess and quantify the area from which the profiling data was obtained.

The CellSensus™ assay of H&E-stained breast cancer epithelium was compared to a 1 $mm^2$ area of scraped tissue (cancer and non-cancer), both after being processed on the Bond RX platform using the In Situ assay with a targeted breast cancer panel of 486 genes. Table 1 below compares the counts for genes with greater than 5000 counts (1st column), demonstrating that the assays correlate for some genes, but that the non-cancer tissue made a significant contribution, which the spatial resolution of the CellSensus™ assay addresses, reflected in the ratio (4th column) of CellSensus (2nd column) to scraped counts (3rd column).

TABLE 1

|        | CellSensus | Scraped | Ratio |
|--------|------------|---------|-------|
| MLPH   | 47728      | 129773  | 0.4   |
| ESR1   | 20216      | 2740    | 7.4   |
| TGFB3  | 13275      | 2417    | 5.5   |
| RPLP0  | 12566      | 10820   | 1.2   |
| MDM4   | 11102      | 11494   | 1.0   |
| UCHL5  | 10990      | 2781    | 4.0   |
| PGR    | 10980      | 4797    | 2.3   |
| YWHAB  | 10626      | 1323    | 8.0   |
| SCUBE2 | 10131      | 1090    | 9.3   |
| TRFC   | 10029      | 1716    | 5.8   |
| CDH1   | 9404       | 7482    | 1.3   |
| CDK4   | 8275       | 8623    | 1.0   |
| WNT5A  | 8247       | 3591    | 2.3   |
| GRB7   | 7585       | 1207    | 6.3   |
| VEGFA  | 7361       | 1192    | 6.2   |
| ERBB2  | 4403       | 3007    | 1.5   |

Example 11: Differentially Expressed Genes Between Cell Lines and Histologic Transitions A cell pellet mixture of MCF7 and Jurkat cells was fixed, embedded, and sectioned. Slides were processed through the in situ assay and then stained with an anti-CD3 antibody and hematoxylin. This staining was used to direct the selection of cells for gene expression profiling, for example a cluster of CD3 negative cells. Table 2 provides counts for the highest overexpressed genes in Jurkat (top set) and MCF7 (bottom set) for cell-type specific profiling directed by the antibody staining and IHC analysis.

TABLE 2

| gene name | MCF7 counts | Jurkat counts |
|---|---|---|
| Jurkat set: | | |
| TSLP | 0 | 170 |
| GDF15 | 52 | 154 |
| SUPV3L1 | 2 | 183 |
| BLMH | 26 | 106 |
| ASAH1 | 0 | 145 |
| ICMT | 1 | 300 |
| RRS1 | 0 | 76 |
| FGR | 0 | 316 |
| PDHX | 0 | 119 |
| MCF7 set: | | |
| ESR1 | 305 | 1 |
| TFF1 | 392 | 2 |
| SLC6A14 | 166 | 2 |
| SPDEF | 104 | 0 |
| PPIC | 102 | 0 |

Profiling of 130 mm diameter areas of cancer and normal epithelium and stroma of prostate (Table 3) was carried out, as depicted FIG. 9, where the spatial resolution provided molecular specificity of biomarkers.

The ratio of detection between different cells, which can be spatially separated by imaging or histologically distinguished, can be 1:10, 1:100, 1:1000 or greater. Where a marker is detected in a cancer cell and there is no (or negligible) detection in a normal or stromal cell, or vice versa, the methods of the invention can be said to provide absolute specificity.

TABLE 3

| biomarker | cancer | normal | stroma |
|---|---|---|---|
| MALAT1* | 768539 | 255266 | 110984 |
| DDX5* | 10190 | 13909 | 5560 |
| HNRNPA1* | 8272 | 319 | 0 |
| MT-ND6* | 6209 | 8050 | 5363 |
| EIF3E* | 4650 | 0 | 1256 |
| MLPH* | 4293 | 2 | 0 |
| RPS7* | 4037 | 0 | 0 |
| ELK4 | 3982 | 3728 | 0 |
| PTP4A1* | 3953 | 0 | 0 |
| MALT1* | 3480 | 0 | 0 |
| ABCC4 † | 3317 | 0 | 0 |
| CDH1 | 3253 | 3349 | 0 |
| HPN* | 3227 | 0 | 0 |
| SPDEF* | 3135 | 0 | 0 |
| RNF167* | 3050 | 0 | 0 |
| TSC22D1 | 2905 | 0 | 0 |
| AKT2* | 2885 | 0 | 0 |
| CALR* | 2807 | 0 | 2 |
| KLK2 ‡ | 2793 | 0 | 0 |
| CAMP* | 2715 | 0 | 0 |
| FAM213A* | 2515 | 0 | 0 |
| RNF4* | 2463 | 0 | 0 |
| EBNA1BP2* | 2332 | 0 | 0 |
| APH1A* | 2238 | 0 | 0 |
| IER2* | 2216 | 0 | 0 |
| SUZ12* | 2179 | 0 | 0 |
| USO1* | 2086 | 0 | 0 |
| MAX* | 2052 | 0 | 0 |
| EPHB6* | 2043 | 0 | 0 |
| SAT1 | 0 | 3544 | 0 |

TABLE 3-continued

| biomarker | cancer | normal | stroma |
|---|---|---|---|
| SOCS4 | 0 | 3506 | 0 |
| NOP56 | 0 | 3130 | 0 |

Biomarkers with an asterisk (*) have previously been associated with prostate cancer. ABCC4 (†), also known as MRP4, is a multidrug resistance gene associated with androgen signaling that pumps drugs out of cells. KLK2 (‡) is the gene for Kallikrein 2, secreted by the prostate in cancer (together with PSA produced by KLK3), and is an important diagnostic marker.

Example 12: Single-Cell TempO-Seq Assay

An in situ TempO-Seq' assay was performed using flow cytometry. The assay sorted single cells directly into PCR plates and incorporated sample barcoding during PCR to uniquely barcode the products from each cell. FIG. 14 shows a correlation of data from a bulk sample of 1000 MCF-7 cells to data from a single cell. The correlation demonstrated that low-expressed genes that were measured from a bulk sample were also measured in the single cells. Biological stochastic expression (genes measured from the bulk sample that were not detected in the single cell) was also observed. In view of the stochastic expression, performance was further assessed using a sum of 11 cells, which provided correlation data with an $R^2=0.89$. Summing 100 cells gave an $R^2=0.99$, which further demonstrated the reproducibility the single-cell data.

Example 13: Split-Mix Barcoding of an In Situ Sample

Cell suspensions of trypsinized, cultured MCF-7 human, MDS-MB-231 human, and 3T3 mouse cells are prepared. These are profiled at 2000 cells per sample using surrogate whole transcriptome human S1500v2 and mouse S1500 commercial TempO-Seq™ assays as benchmark assays (illustrated by FIG. 15, part A, followed by amplification). Although the panels of detector oligos are highly species-specific, the benchmark assays can identify detector oligos that are cross-reactive across species (or that are less species-specific) and can identify species-specific gene profiles for human and mouse cells.

A reference in situ TempO-Seq™ protocol (illustrated by FIG. 15, part A, including wash steps and amplification) is used to generate reference data for bulk samples of 2000 cells per sample. Cells are fixed and washed. A cocktail of UDOs and DDOs is added and allowed to hybridize, then washed. A nuclease is added, incubated, and then washed. A ligase is added, incubated, and then washed. The ligation products are amplified by PCR to generate a library of sequenceable DO adducts. The samples are transferred to a PCR plate containing universal forward- and reverse-barcoded primers, with a different barcode sequence in each well. The primers are universal in the sense they contain sequences (such as P1 or L1) that can hybridize to detector oligos for each or any gene. The primers can also have a predetermined S5 or S7 sequence to facilitate use with commercial sequencing workflows. Alignment and analysis are carried out using an automated TempO-SeqR™ package that provides sequencing metrics, count tables, differential expression, and pathway analysis.

Correlation plots of gene expression for bulk samples of each cell line are measured by the benchmark assay compared to the in situ assay, and with each variation tested.

Cross-Linkable Detector Oligos

Different methods of crosslinking in situ are tested using MCF-7 cells to increase the total number of reads detected. In FIG. 16, the UDO is designed with an anchor sequence (UR2') that hybridizes to the target RNA but is not amplified. Accordingly, a set of UDOs for six high expressed genes are synthesized with different crosslinking agents within the anchor sequence or at their 3' end. The optional crosslinking is illustrated by "XX" in the figure.

Serial Barcoding by Ligation of Barcoded Oligos

Sets of ligation template linkers (LTL) are prepared. In FIG. 15, part B, an LTL is an oligo having the structure 3'-L2-L1-5', where L2 is a defined nucleic acid sequence, and L1 is a sequence complementary to P1. As described above, the P1 sequence can appear as the universal sequence at the 5' end of a DDO, and can be phosphorylated. (In other versions, the L1 can be complementary to a defined L1' sequence in the assay design.) The LTL21 shown serves as a splint to link the L2 and L1 sequence.

A series of B1 barcoded oligos is also provided, having a general structure of 5'-L3'-barcode-L2'-3'. A set of 96 selected sequences provides 9-base barcodes for the B1 series. The barcoded oligos are designed so that the barcode sequence is flanked by a sequence complementary to a portion of one LTL and by a sequence complementary to a portion of another LTL. For example, the B1 barcoded oligo 5'-L3'-barcode-L2'-3' contains a 9-base barcode flanked by a sequence complementary to L3 in an LTL23 linker and by a sequence complementary to L2 in an LTL21 linker. In some figures, individual barcodes are notated B1a, B1b, B1c, to B1z to designate different individual 9-base sequences, although this does not limit the numerical range of possible barcodes.

A similar B2 series of barcoded oligos is also prepared where the 5' sequence is a universal primer binding sequence, such as P3. For example, a B2 barcoded oligo can have 5'-P3-barcode-L2-3'. The P3 primer sequence can then facilitate amplification of the serially barcoded construct.

In one experiment, exemplified in part A of FIG. 15, a hybridization complex of a target RNA, DDO and UDO is provided, and then an LTL21 (3'-L2-P1'-5') is allowed to hybridize to the DDO. In part C, a B1 barcoded oligo is added, shown as 3'-L3'-B1a-L2'-5', where the B1 oligo hybridizes to the L2 region of the LTL21. The B1 oligo is ligated to the P1 region of the DDO. An LTL is then added (shown as LTL23) to hybridize to the L3 region of the ligated B1 oligo. The addition of a B1 oligo, hybridization, ligation, addition of an LTL, and hybridization is repeated up to three times (with appropriate washes). Then a B2 oligo is added, allowed to hybridize to an L2' region of an LTL23, followed by ligation, in order to add a universal P3 amplification region. The resulting barcoded products are then amplified and sequenced.

By barcoding human MCF-7 and mouse 3T3 cells separately as bulk samples and then analyzing the human- and mouse-specific S1500 gene sets, the quality of barcoding and potential cross-barcoding error rate is evaluated.

Split-Mix Approach to Serially Barcode Single Cells

Single cells from MCF-7, MDS-MB-231, and 3T3 lines are prepared (and mixtures of those lines). A split-mix protocol is performed, as illustrated in FIG. 15. The sample cells are aliquoted into a prepared 48-well PCR plate, where each well contains a different B1 barcoded oligo. Part C illustrates the components of one well. After ligation and washing, the individual reactions are pooled, mixed, and re-aliquoted into a second 48-well PCR plate. As shown, B1 barcoded oligos are added and ligated in two further iterations. Then a set of B2 barcoded oligos are added and ligated in a final iteration. The resulting barcoded products are then amplified and sequenced.

The results from the split-mix protocol are analyzed for barcoding error rates, percentage of doublets, dynamic range of transcripts/cell, number of genes/single cell, correlation of summed single cells to bulk, and quantification of the sensitivity to measure low- and medium-expressed genes from single cells.

Serial Barcoding Using Click Chemistry

Barcoded oligos can be attached to a pair of ligated detectors using click chemistry techniques. In an experiment, the chemistry uses copper-catalyzed azide-alkyne cycloaddition. This experiment avoids the need for LTL oligos and enzymatic ligation. FIG. 17 illustrates the workflow using a series of B1 barcoded oligos that are synthesized with 5'-iodo functionalization. B2 barcoded oligos are also provided with a two-base spacer at each end of the barcode between a 5'-iodo and a 3'-O-propargyl (alkynyl) functional group. The 5'-iodo is activated prior to each round of barcoding by treating with azide to form a reactive 5'-azido group. The coupling is carried out in the presence of a copper catalyst.

In another experiment, template-mediated Quick Click ligation is performed using LTL and barcode flanking sequences as with the templated ligation method as in FIG. 16, replacing the use of ligase with click chemistry.

In both experiments, the click chemistries are performed in the presence of copper catalyst or with a catalyst-free, strain-promoted azide-alkyne cycloaddition.

Example 14: Crosslinking of Nucleic Acids In Situ

Different methods of crosslinking in situ are tested using MCF-7 cells to increase the total number of reads detected. In FIG. 16, the UDO is designed with an anchor sequence (UR2') that hybridizes to the target RNA but is not amplified. Accordingly, a set of UDOs for six high expressed genes are synthesized with different crosslinking agents within the anchor sequence or at their 3' end. The optional crosslinking is illustrated by "XX" in FIG. 16.

The headings provided above are intended only to facilitate navigation within the document and should not be used to characterize the meaning of one portion of text compared to another. Skilled artisans will appreciate that additional embodiments are within the scope of the invention. The invention is defined only by the following claims; limitations from the specification or its examples should not be imported into the claims.

We claim:

1. A method for detecting target nucleic acid sequences in samples, wherein a target sequence has a downstream region (DR) and an upstream region (UR), comprising
   (a) contacting the samples with a pair of detector oligos (DOs), which pair comprises
       a downstream detector oligo (DD) having a complementary downstream region (DR') and
       a separate upstream detector oligo (UD) having a complementary upstream region (UR'),
       wherein at least one of the DD or UD has a second complementary region (DR2' or UR2') separated from the DR' or UR' by a noncomplementary region (CP1) that does not hybridize to the target nucleic acid, whereby the DR2' or UR2' specifically hybridizes to a DR2 or UR2 of the target nucleic acid,
       thereby allowing the pair of detectors to hybridize specifically to target nucleic acids;
   (b) ligating the DR' and UR' if both are specifically hybridized to the DR and UR of a target sequence;
   (c) labeling the ligated detectors of step (b) with a barcode sequence in a plurality of samples; and
   (d) labeling the product of step (c) with a barcode sequence in a different plurality of samples;
   whereby the barcoded ligation product indicates the presence of the target sequence and identifies the sample.

2. The method of claim 1, further comprising the step of exposing hybridization complexes to at least one nuclease that degrades single strands but does not significantly degrade double strands.

3. The method of claim 1, wherein step (c) or (d) is performed by attaching an oligo having a barcode sequence.

4. The method of claim 1, further comprising the step of mixing the labeled products of step (c) or (d), and dividing the mixed labeled products into sets of different pluralities of samples.

5. The method of claim 1, further comprising repeating step (d) with a different plurality of samples.

6. The method of claim 1, wherein
   step (c) is performed on one end of the ligated product; and
   step (d) is performed on the other end of the ligated product.

7. The method of claim 1, 2, 3, 4, 5, or 6, wherein step (d) is performed by attaching oligos having an amplification sequence.

8. The method of claim 1, 2, 3, 4, 5, or 6, further comprising the step of
   permeabilizing cell walls, cell membranes, or subcellular structures;
   dissociating individual cells;
   cross-linking detectors to target sequence; or
   eluting the ligation product.

9. The method of claim 1, 2, 3, 4, 5, or 6, further comprising the step of capturing the target nucleic acids, the ligation products, or amplification products thereof with a capture oligo.

* * * * *

UNITED STATES PATENT AND TRADEMARK OFFICE
CERTIFICATE OF CORRECTION

| | | |
|---|---|---|
| PATENT NO. | : 11,434,538 B2 | Page 1 of 1 |
| APPLICATION NO. | : 16/865246 | |
| DATED | : September 6, 2022 | |
| INVENTOR(S) | : Milos Babic et al. | |

It is certified that error appears in the above-identified patent and that said Letters Patent is hereby corrected as shown below:

In the Specification

Column 1, Line 41, in the STATEMENT OF GOVERNMENT SUPPORT, the corrected Statement should read as follows:
STATEMENT OF GOVERNMENT SUPPORT
This invention was made with government support under grants R43 & R44 ES024107, R43 & R44 HG007339, R43 & R44 HG008917, R43 & R44 HG007815, awarded by the National Institutes of Health (NIH). The government has certain rights in the invention.

Signed and Sealed this
Second Day of September, 2025

Coke Morgan Stewart
*Acting Director of the United States Patent and Trademark Office*